(12) United States Patent
Gross et al.

(10) Patent No.: US 12,343,526 B1
(45) Date of Patent: Jul. 1, 2025

(54) BLOOD FLOW ENHANCEMENT THERAPY SYSTEMS

(71) Applicant: BRAINFLOW MEDICAL, INC., Sunnyvale, CA (US)

(72) Inventors: Yossi Gross, Moshav Mazor (IL); Ofri Vaisman, Sunnyvale, CA (US); Ivan Tzvetanov, Kailua Kona, HI (US); Steve Herbowy, San Francisco, CA (US); Apratim Dixit, Round Rock, TX (US)

(73) Assignee: BRAINFLOW MEDICAL, INC., Sunnyvale, CA (US)

( * ) Notice: Subject to any disclaimer, the term of this patent is extended or adjusted under 35 U.S.C. 154(b) by 0 days.

(21) Appl. No.: 19/011,088

(22) Filed: Jan. 6, 2025

Related U.S. Application Data

(63) Continuation-in-part of application No. 18/640,726, filed on Apr. 19, 2024, now Pat. No. 12,208,267.

(51) Int. Cl.
*A61N 1/05* (2006.01)

(52) U.S. Cl.
CPC ......... *A61N 1/0558* (2013.01); *A61N 1/0546* (2013.01); *A61N 1/0553* (2013.01)

(58) Field of Classification Search
CPC . A61N 1/36114; A61N 1/3603; A61N 1/0456
USPC .......................................................... 607/7
See application file for complete search history.

(56) References Cited

U.S. PATENT DOCUMENTS

| | | | |
|---|---|---|---|
| 6,526,318 B1 | 2/2003 | Ansarinia | |
| 7,117,003 B2 | 10/2006 | Shalev et al. | |
| 7,120,489 B2 | 10/2006 | Shalev et al. | |
| 7,561,919 B2 | 7/2009 | Shalev et al. | |
| 7,636,597 B2 | 12/2009 | Gross et al. | |
| 8,954,149 B2 | 2/2015 | Shalev | |
| 9,233,245 B2 | 1/2016 | Lamensdorf et al. | |
| 11,576,719 B2 | 2/2023 | Townley et al. | |
| 12,208,267 B1 | 1/2025 | Gross et al. | |
| 2004/0253304 A1 | 12/2004 | Gross et al. | |

(Continued)

FOREIGN PATENT DOCUMENTS

| | | |
|---|---|---|
| WO | 0185094 A2 | 11/2001 |
| WO | 2022056310 A1 | 3/2022 |
| WO | 2023225265 A1 | 11/2023 |

OTHER PUBLICATIONS

Communication dated Jun. 27, 2024 issued by the United States Patent and Trademark Office in U.S. Appl. No. 18/351,247.

(Continued)

*Primary Examiner* — Nadia A Mahmood
(74) *Attorney, Agent, or Firm* — Sughrue Mion, PLLC

(57) ABSTRACT

A method is provided for stimulating a sphenopalatine ganglion (SPG) of a patient, the method including inserting a tube and an electrode mount into a nasal cavity of the patient and advancing the tube along a floor of the nasal cavity to near a posterior end of an inferior turbinate. One or more electrodes of the electrode mount are deployed superiorly away from the tube while the tube is disposed along the floor of the nasal cavity and the electrode mount is disposed within the nasal cavity, so as to bring at least one of the one or more electrodes into contact with a wall of the nasal cavity. A current configured to stimulate the SPG via the wall is applied to the one or more electrodes. Other embodiments are also described.

22 Claims, 45 Drawing Sheets

(56) References Cited

U.S. PATENT DOCUMENTS

| | | |
|---|---|---|
| 2005/0159790 A1 | 7/2005 | Shalev |
| 2006/0095066 A1 | 5/2006 | Chang et al. |
| 2008/0269716 A1 | 10/2008 | Bonde et al. |
| 2012/0323214 A1 | 12/2012 | Shantha |
| 2019/0290908 A1 | 9/2019 | Hsu et al. |
| 2020/0100838 A1 | 4/2020 | Townley et al. |
| 2020/0179697 A1* | 6/2020 | Schepis ............... A61N 1/3614 |
| 2025/0018187 A1 | 1/2025 | Gross et al. |
| 2025/0018193 A1 | 1/2025 | Gross et al. |

OTHER PUBLICATIONS

Communication dated Jul. 11, 2024 issued by the United States Patent and Trademark Office in U.S. Appl. No. 18/640,726.
"The Comfortable Alternative for Nasal Tube Securement", The AMT™ Bridle: Nasal Tubing Retaining System, Nov. 8, 2024, 14 pages.

* cited by examiner

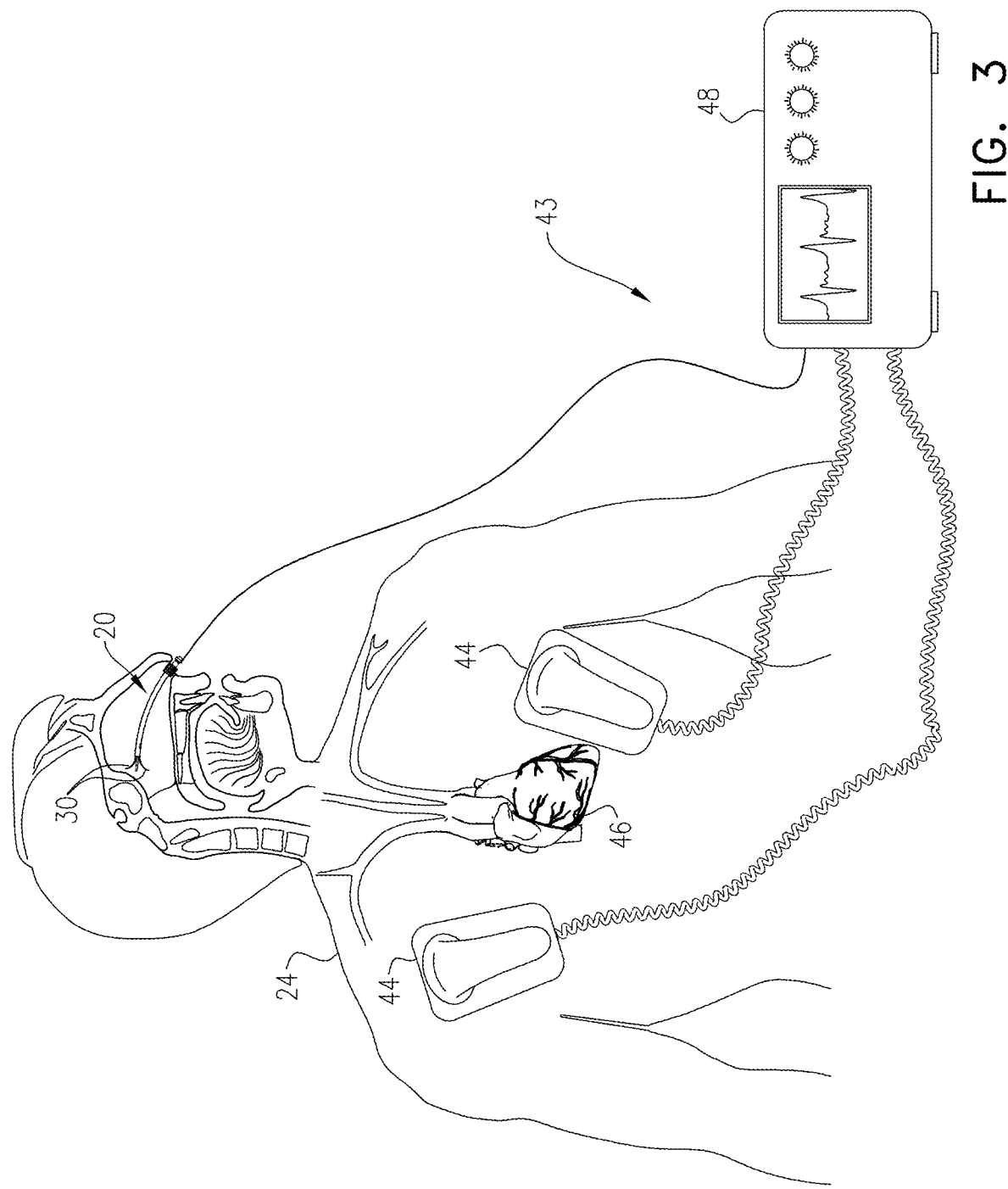

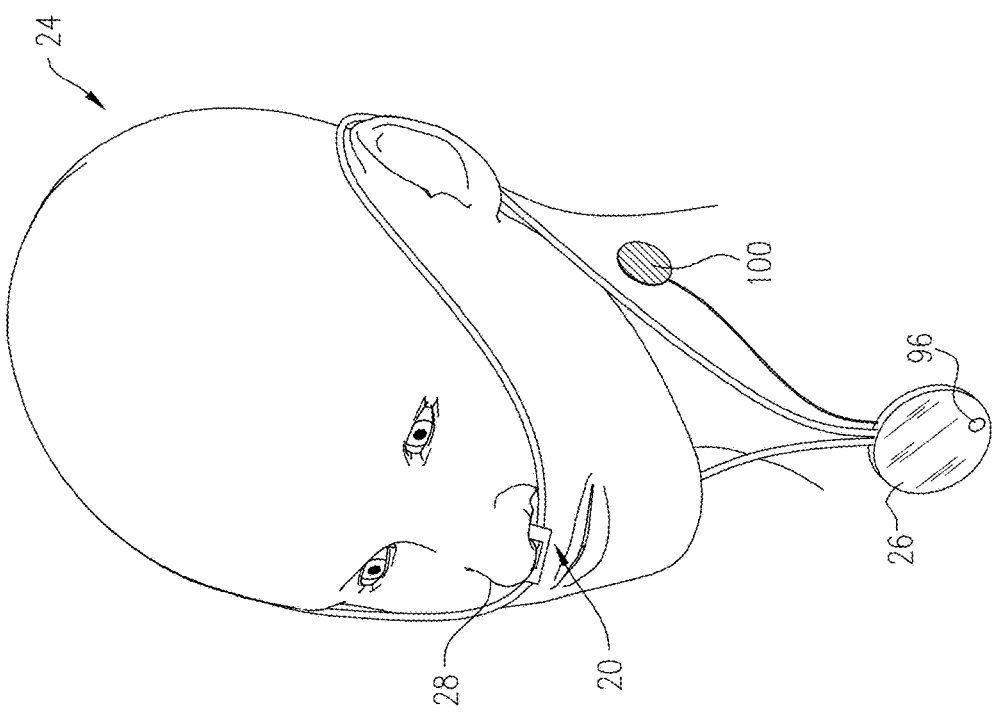
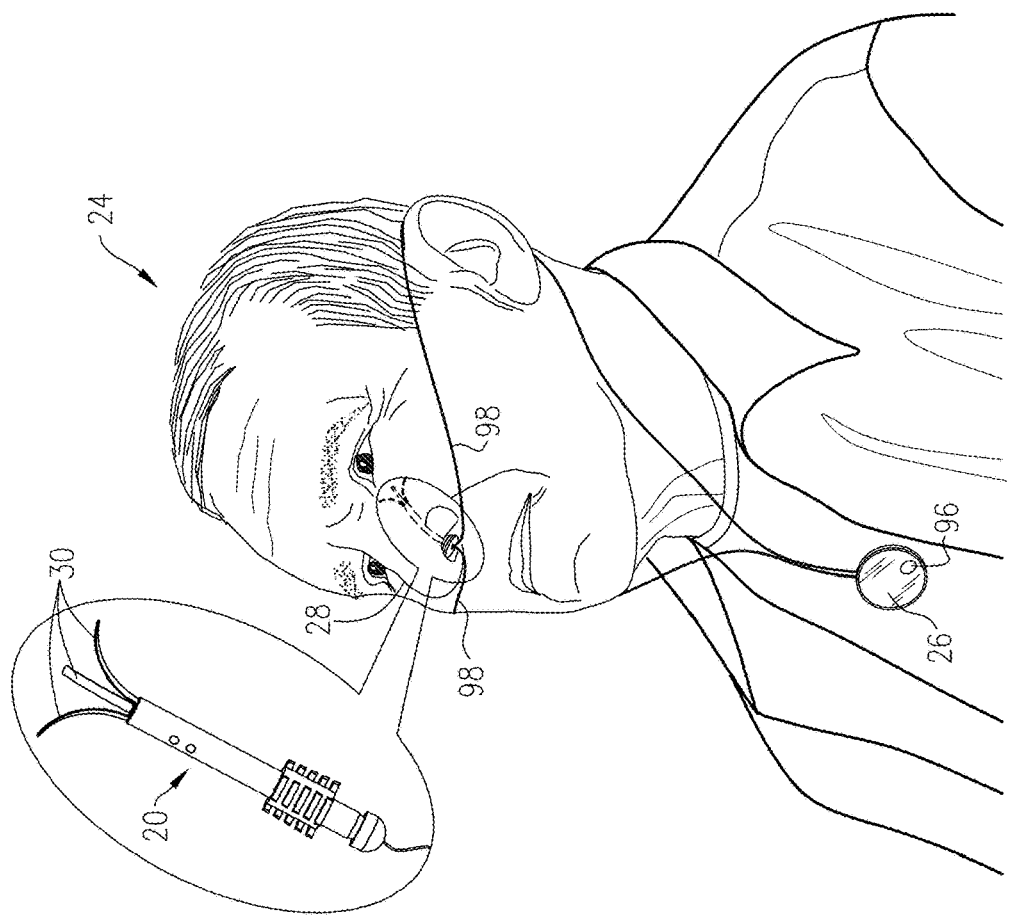
FIG. 4A
FIG. 4B

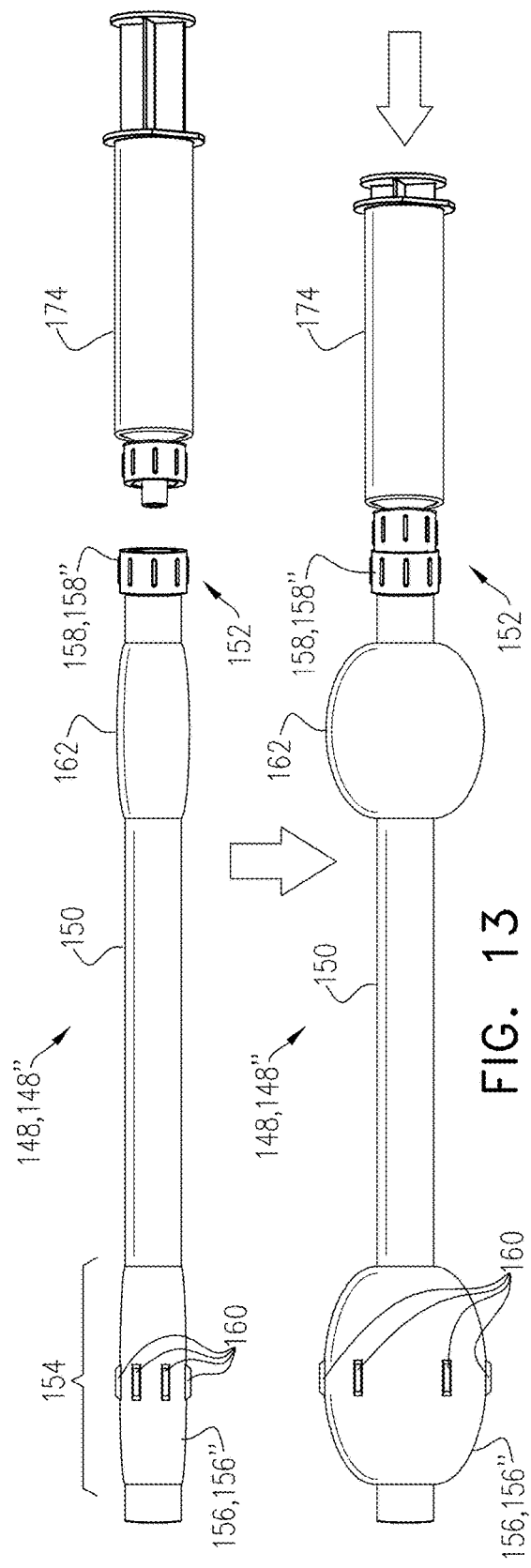
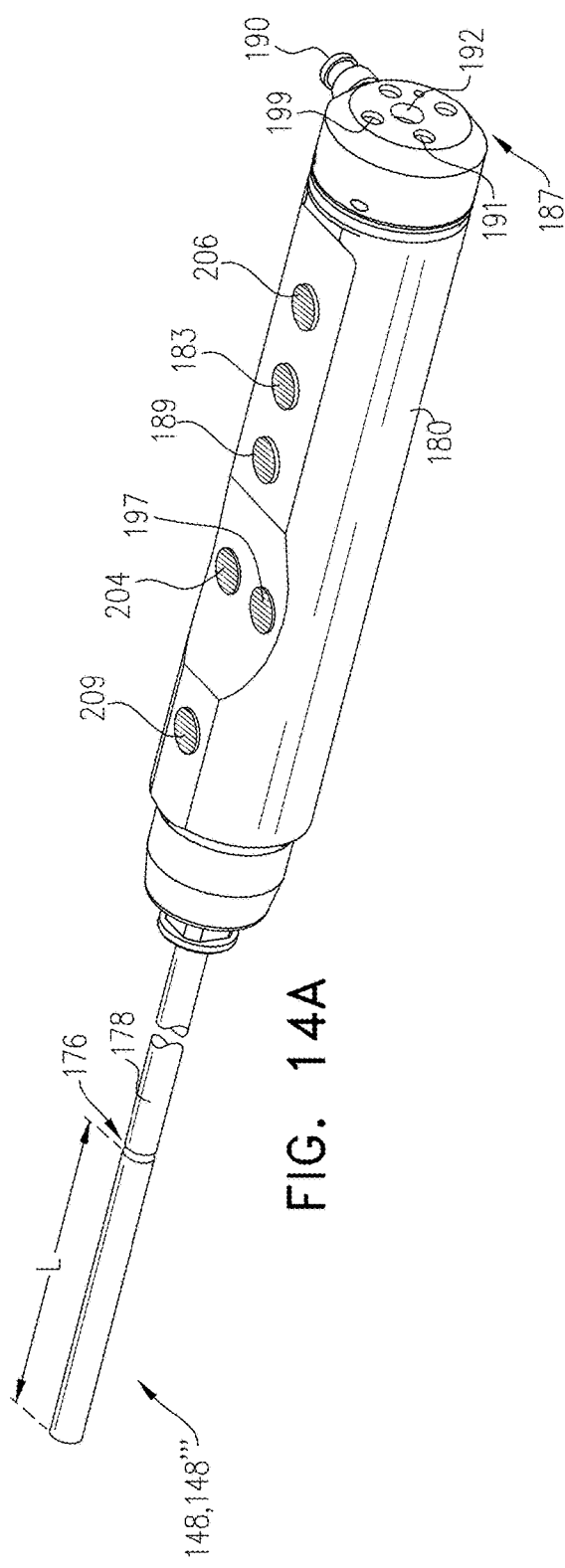
FIG. 13
FIG. 14A

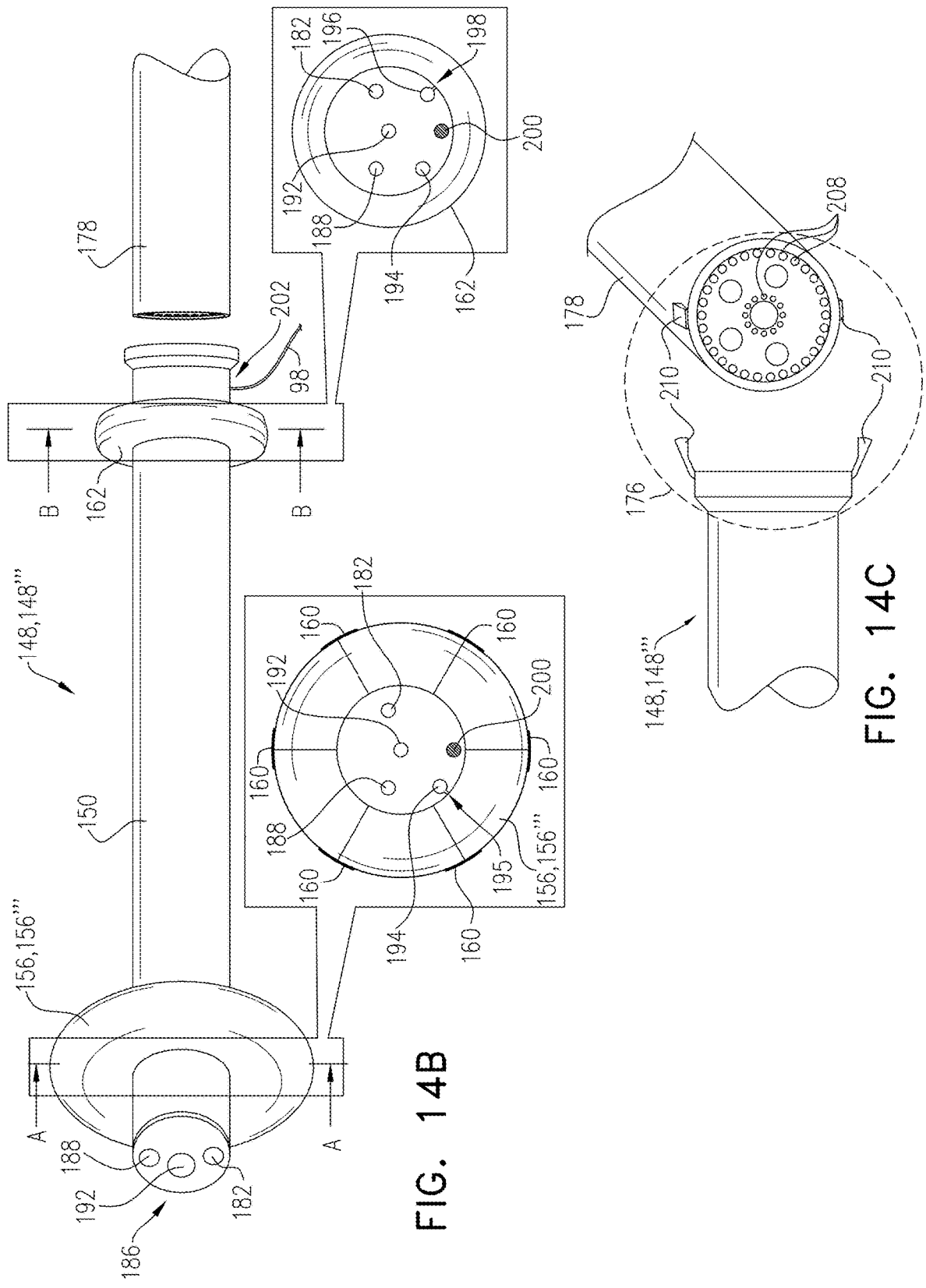

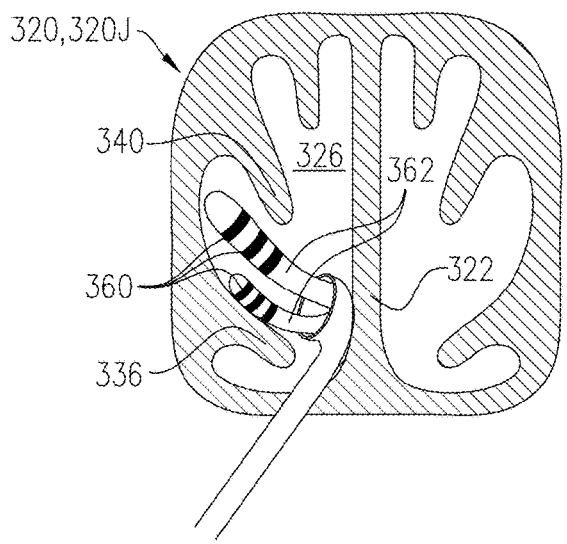
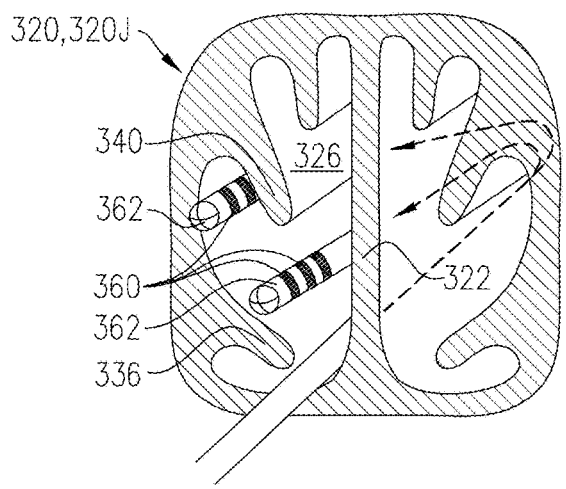
FIG. 29A  FIG. 29B
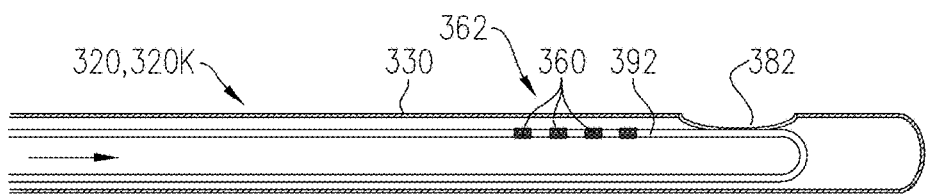
FIG. 30A
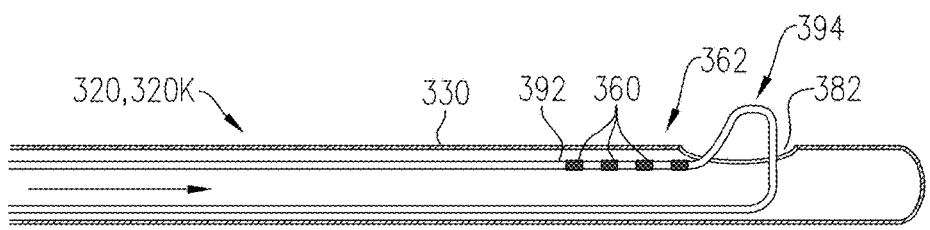
FIG. 30B
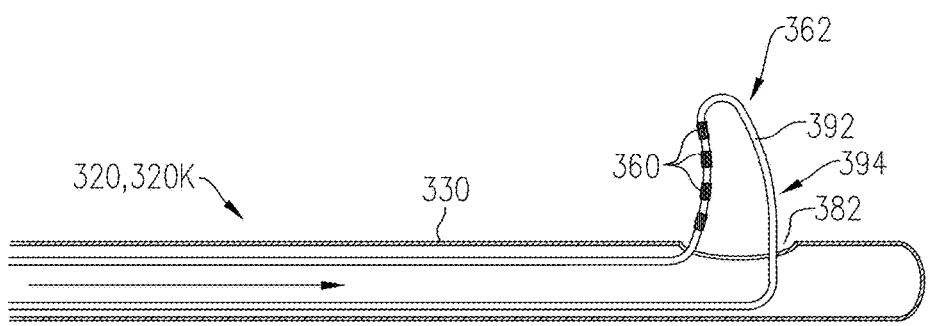
FIG. 30C

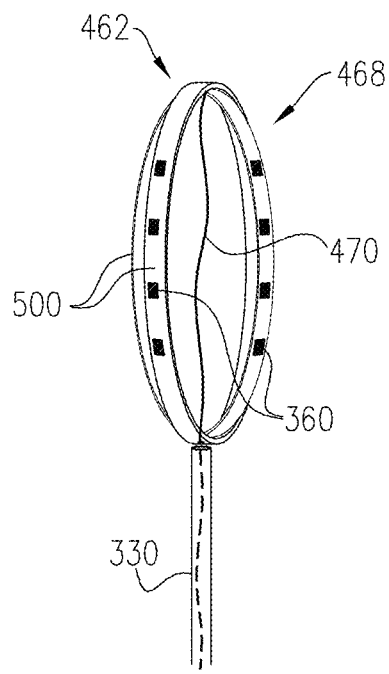 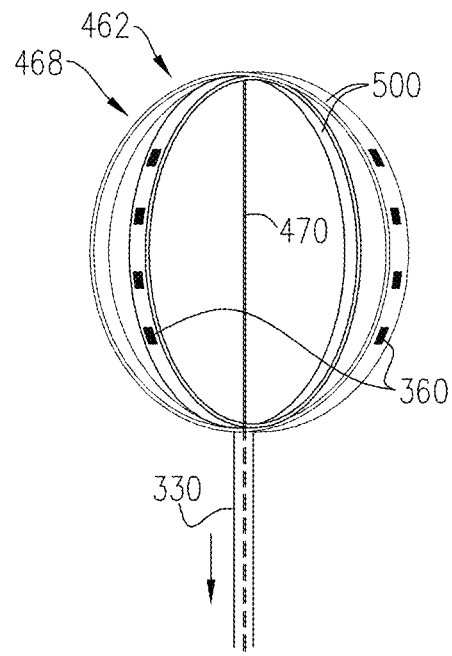
FIG. 45A  FIG. 45B
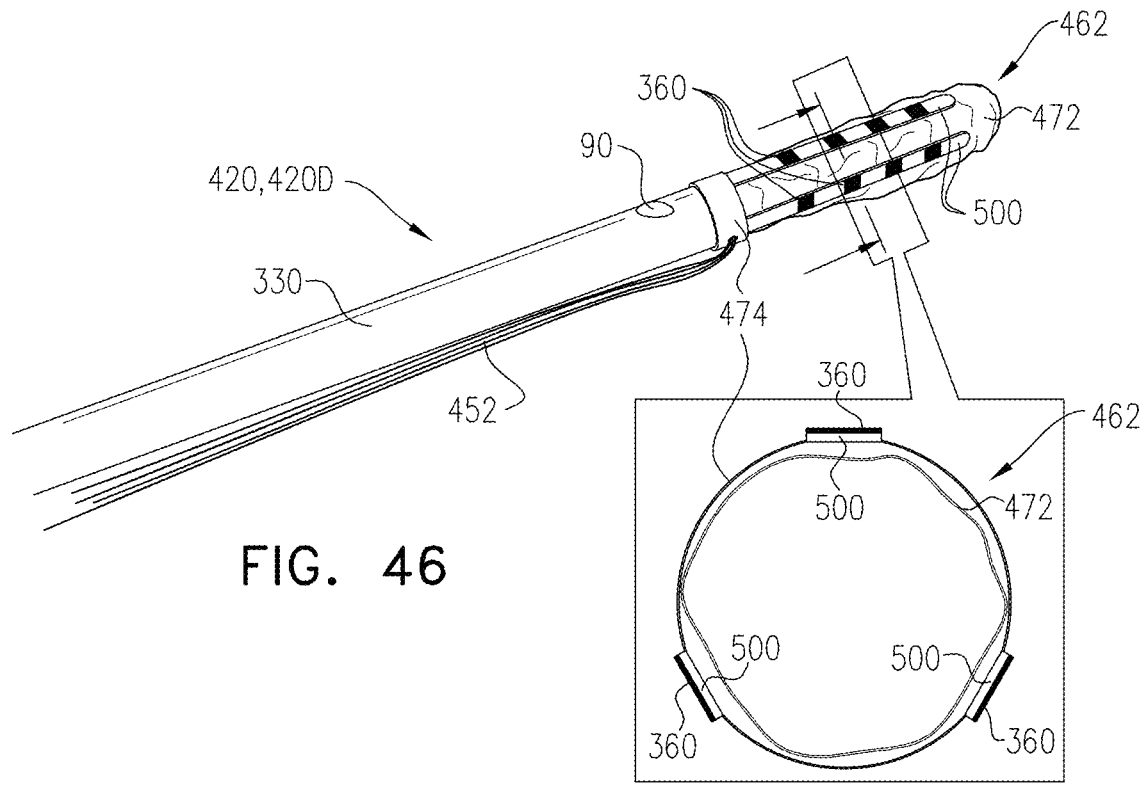
FIG. 46

BLOOD FLOW ENHANCEMENT THERAPY SYSTEMS

CROSS-REFERENCE TO RELATED APPLICATIONS

The present application claims priority from and is a continuation-in-part of U.S. application Ser. No. 18/640,726, filed Apr. 19, 2024, now U.S. Pat. No. 12,208,267, which is incorporated herein by reference.

FIELD OF THE INVENTION

The present application relates generally to enhancing cerebral blood flow, and specifically to stimulation of the sphenopalatine ganglion (SPG).

BACKGROUND OF THE APPLICATION

International Patent Application WO 2001/085094 to Shalev et al. describes apparatus for modifying a property of a brain of a patient, including one or more electrodes, adapted to be applied to a site selected from a group of sites consisting of: a sphenopalatine ganglion (SPG) of the patient and a neural tract originating in or leading to the SPG. A control unit is adapted to drive the one or more electrodes to apply a current to the site capable of inducing an increase in permeability of a blood-brain barrier (BBB) of the patient, (b) a change in cerebral blood flow of the patient, and/or (c) an inhibition of parasympathetic activity of the SPG. Other embodiments are also described.

U.S. Pat. No. 9,233,245 to Lamensdorf et al. describes a method for treating a subject, including applying electrical stimulation to a site of the subject selected from the group consisting of: a sphenopalatine ganglion (SPG), a greater palatine nerve, a lesser palatine nerve, a sphenopalatine nerve, a communicating branch between a maxillary nerve and an SPG, an otic ganglion, an afferent fiber going into the otic ganglion, an efferent fiber going out of the otic ganglion, an infraorbital nerve, a vidian nerve, a greater superficial petrosal nerve, and a lesser deep petrosal nerve. The stimulation is configured to excite nervous tissue of the site at a strength sufficient to induce at least one neuroprotective occurrence selected from the group consisting of: an increase in cerebral blood flow (CBF) of the subject, and a release of one or more neuroprotective substances, and insufficient to induce a significant increase in permeability of a blood-brain barrier (BBB) of the subject. Other embodiments are also described.

SUMMARY OF THE APPLICATION

In accordance with some applications of the present invention, systems and methods are provided for increasing cerebral blood flow (CBF) of a patient, such as for treatment of ischemic stroke or for treatment and prevention of dementia, such as vascular dementia or Alzheimer's disease. For some applications, two or more electrodes are coupled to tissue of a patient and CBF of the patient is increased by activating a power source to drive the electrodes to apply current to a sphenopalatine ganglion (SPG) of the patient.

For some applications, an SPG stimulating device is placed in a nose of the patient for nasal-only stimulation of the SPG. The SPG stimulating device typically has a sheath, a nasal stabilizer disposed around the sheath for stabilizing the device with respect to a nostril of the patient, an electrode mount slidably disposed within the sheath, and at least one electrode coupled to the mount and deployable out of the sheath (e.g., by pushing the electrode mount distally or by pulling the sheath proximally) in order to position the electrode to stimulate the SPG. The SPG stimulating device may include a camera configured to facilitate navigation of the sheath toward the SPG, and/or a sensor configured to sense a physiological response of the patient to stimulation of the SPG.

Alternatively, for some applications, the electrodes of the SPG stimulating device are not deployed from within a sheath, but rather a distal end portion of a housing of the SPG stimulating device is shaped to define a plurality of electrode arms that are configured to open outward away from a central longitudinal axis of the housing during deployment of the electrode arms. At least one electrode is coupled to each electrode arm such that when the distal end portion is placed within the nose and the electrode arm is deployed, the at least one electrode is positioned to stimulate the SPG.

Alternatively, for some applications, an inflatable SPG stimulating device is a flexible tube configured for placement within the nose and has at least one inflatable electrode mount at a distal end portion of the tube with at least one electrode coupled to the inflatable mount, and an inflation actuator at a proximal end portion of the tube. When the inflatable SPG stimulating device is placed within the nose and the at least one inflatable electrode mount is inflated, the at least one electrode is positioned to stimulate the SPG. Typically, the inflatable SPG stimulating device also includes an inflatable nasal stabilizer configured to stabilize the flexible tube with respect to a nostril of the nose when the flexible tube is disposed within the nose and the inflatable nasal stabilizer is inflated.

In some applications of the present invention, an SPG stimulating device comprises a tube, which is dimensioned to be insertable along a floor of a nasal cavity to near a posterior end of an inferior turbinate; and an electrode mount, which comprises one or more electrodes. Typically, the SPG stimulating device is configured to deploy the one or more electrodes superiorly away from the tube while the tube is disposed along the floor of the nasal cavity, so as to position the one or more electrodes against a wall of the nasal cavity for stimulating the SPG.

For some applications, the wall is a lateral wall of the nasal cavity, and the SPG stimulating device is configured to deploy the one or more electrodes superiorly and laterally away from the tube, so as to position the one or more electrodes against the lateral wall of the nasal cavity for stimulating the SPG. For some of these applications, the SPG stimulating device is configured to deploy the one or more electrodes superiorly and laterally away from the tube to an area of a middle meatus, near the posterior end of the inferior turbinate and a posterior end of a middle turbinate and an area of a sphenopalatine foramen, while the tube is disposed along the floor of the nasal cavity, so as to position the one or more electrodes against the wall of the nasal cavity for stimulating the SPG.

For some applications, the electrode mount is configured to secure the one or more electrodes in place after deployment. For example, the electrode mount may contact sufficient points within the nasal cavity to prevent unwanted motion of the one or more electrodes.

In accordance with some applications of the present invention, systems and methods are provided for increasing CBF of a patient in cardiac arrest or in an acute post-cardiac arrest phase. For some applications, two or more electrodes are coupled to tissue of a patient in cardiac arrest or in an acute post-cardiac arrest phase and CBF of the patient is increased by activating a power source to drive the electrodes to apply current to an SPG of the patient. For some applications, the SPG stimulation is applied after a defibrillator is used to apply an electric charge to a heart of the patient. Any of the techniques described herein for stimulating the SPG may be used for increasing CBF of a patient in cardiac arrest or in an acute post-cardiac arrest phase.

There is therefore provided, in accordance with an application of the present invention, a method for stimulating a sphenopalatine ganglion (SPG) of a patient, the method including:

inserting a tube and an electrode mount into a nasal cavity of the patient and advancing the tube along a floor of the nasal cavity to near a posterior end of an inferior turbinate;

deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and applying, to the one or more electrodes, a current configured to stimulate the SPG via the wall.

For some applications, the wall is a lateral wall of the nasal cavity, and deploying the one or more electrodes includes deploying the one or more electrodes superiorly and laterally away from the tube while the tube is disposed along the floor of the nasal cavity, so as to bring at the least one of the one or more electrodes into the contact with the lateral wall of the nasal cavity.

For some applications, deploying the one or more electrodes includes deploying the one or more electrodes superiorly and laterally away from the tube to an area of a middle meatus and an area of a sphenopalatine foramen while the tube is disposed along the floor of the nasal cavity.

For some applications, the wall is a lateral wall of the nasal cavity, and deploying the one or more electrodes includes deploying the one or more electrodes superiorly and laterally away from the tube to the area of the middle meatus and the sphenopalatine foramen, so as to position the one or more electrodes against the lateral wall of the nasal cavity.

For some applications, the tube is shaped so as to define a distal end opening, and deploying the one or more electrodes away from the tube includes deploying the one or more electrodes away from the tube via the distal end opening.

For some applications, the tube is shaped so as to define a side opening, and deploying the one or more electrodes away from the tube includes deploying the one or more electrodes away from the tube via the side opening.

For some applications, deploying the one or more electrodes includes, after deploying the one or more electrodes superiorly away from the tube, disengaging the tube from the electrode mount.

For some applications, an outer diameter of the tube is 2-6 mm.

For some applications, a length of the tube is 5-8.5 cm.

For some applications, the tube is steerable, and deploying the one or more electrodes superiorly away from the tube while the tube is disposed along the floor of the nasal cavity includes activating a deflecting mechanism to bend a distal end portion of the tube in at least one direction with respect to an axis of the tube, in order to facilitate superior deployment of the one or more electrodes away from the tube.

For some applications, the tube is shaped so as to define a distal end opening, and deploying the one or more electrodes away from the tube includes deploying the one or more electrodes away from the tube via the distal end opening.

For some applications, the tube is unidirectionally steerable.

For some applications, the tube is deflectable at a deflection region of the tube that is 0.5-2.5 cm from a distal end of the tube.

For some applications, the tube is deflectable at a deflection region of the tube that is less than 6 cm from a proximal end of the tube.

For some applications, a distal end portion of the tube is configured to be curved when in an unconstrained resting state, in order to facilitate superior deployment of the one or more electrodes away from the tube.

For some applications, inserting the tube includes inserting the tube into the nasal cavity while at least the distal end portion is removably disposed in a sheath so as to constrain the distal end portion of the tube in a straightened state.

For some applications, the electrode mount is coupled to a distal end portion of the tube.

For some applications, the electrode mount is removably disposed within the tube, and is configured, upon deployment from the tube, to superiorly deploy the one or more electrodes and position the one or more electrodes against a wall of the nasal cavity for stimulating the SPG.

For some applications, the electrode mount is removably constrained within the tube in a constrained state, and is configured to expand to an expanded state after the deployment from the tube, so as to superiorly deploy the one or more electrodes and position the one or more electrodes against a wall of the nasal cavity for stimulating the SPG.

For some applications:
  the electrode mount includes an inflatable electrode mount,
  the one or more electrodes are coupled to an external surface of the inflatable electrode mount, and
  deploying the one or more electrodes includes inflating the inflatable electrode mount, to superiorly deploy the one or more electrodes and position the one or more electrodes against the wall of the nasal cavity.

For some applications:
  the inflatable electrode mount is removably disposed in the tube while the inflatable electrode mount is in an uninflated state, and
  deploying the one or more electrodes includes deploying the electrode mount from the tube and inflating the inflatable electrode mount, to superiorly deploy the one or more electrodes and position the one or more electrodes against the wall of the nasal cavity.

For some applications, the inflatable electrode mount, when inflated and unconstrained, has a long axis that is generally L-shaped.

For some applications, the inflatable electrode mount, when inflated and unconstrained, has a long axis that is arcuate.

For some applications, the inflatable electrode mount, when inflated and unconstrained, has a long axis that has a distal segment and a proximal segment that define an angle of 30-150 degrees therebetween.

For some applications, the electrode mount is coupled to a distal end portion of the tube.

For some applications, the electrode mount is elongate and is removably constrained coiled around a distal end portion of the tube, and is configured, upon being released from being constrained, to at least partially uncoil, so as to superiorly deploy the one or more electrodes and position the one or more electrodes against a wall of the nasal cavity for stimulating the SPG.

For some applications, the electrode mount includes a flexible wire, to which the one or more electrodes are fixed.

For some applications, deploying the one or more electrodes includes shaping the flexible wire as a loop.

For some applications, deploying the one or more electrodes includes shaping the flexible wire as a curve.

For some applications, the flexible wire is removably disposed within the tube, and deploying the one or more electrodes includes deploying the flexible wire from the tube via first and second side openings defined by the tube.

For some applications, the electrode mount includes one or more struts, to which the one or more electrodes are fixed.

For some applications, the one or more struts include a plurality of struts arranged as spokes radiating from a hub.

For some applications, the one or more struts include a plurality of struts arranged as a frame.

For some applications, deploying the one or more electrodes includes inflating a balloon, which is not fixed to the one or more struts, so as to press the one or more struts into the wall of the nasal cavity.

For some applications, the one or more struts include a plurality of struts arranged on only one side of the balloon.

For some applications, the one or more struts include a plastically deformable material.

For some applications, the plastically deformable material includes a malleable material.

For some applications, deploying the one or more electrodes includes, after deploying the one or more electrodes superiorly away from the tube, disengaging the tube and the balloon from the electrode mount.

For some applications, the electrode mount includes the balloon.

For some applications, deploying the one or more electrodes includes, after deploying the one or more electrodes superiorly away from the tube, disengaging the tube from the electrode mount, including from the balloon.

For some applications, the electrode mount includes a spring, to which the one or more electrodes are coupled.

For some applications, the spring is shaped so as to define undulations having proximal and distal peaks.

For some applications, the undulations surround an axis.

There is further provided, in accordance with an application of the present invention, a sphenopalatine ganglion (SPG) stimulating device for stimulating an SPG of a patient from within a nasal cavity, the device including:
- a tube, which is dimensioned to be insertable along a floor of the nasal cavity to near a posterior end of an inferior turbinate; and
- an electrode mount, which includes one or more electrodes,
- wherein the device is configured to deploy the one or more electrodes superiorly away from the tube while the tube is disposed along the floor of the nasal cavity and the electrode amount is disposed within the nasal cavity, so as to position the one or more electrodes against a wall of the nasal cavity for stimulating the SPG.

For some applications, the wall is a lateral wall of the nasal cavity, and the device is configured to deploy the one or more electrodes superiorly and laterally away from the tube, so as to position the one or more electrodes against the lateral wall of the nasal cavity for stimulating the SPG.

For some applications, the device is configured to deploy the one or more electrodes superiorly and laterally away from the tube to an area of a middle meatus and an area of a sphenopalatine foramen while the tube is disposed along the floor of the nasal cavity, so as to position the one or more electrodes against the wall of the nasal cavity for stimulating the SPG.

For some applications, the wall is a lateral wall of the nasal cavity, and the device is configured to deploy the one or more electrodes superiorly and laterally away from the tube to the area of the middle meatus and the sphenopalatine foramen, so as to position the one or more electrodes against the lateral wall of the nasal cavity for stimulating the SPG.

For some applications, the tube is shaped so as to define a distal end opening, and the one or more electrodes are deployable away from the tube via the distal end opening.

For some applications, the tube is shaped so as to define a side opening, and the one or more electrodes are deployable away from the tube via the side opening.

For some applications, the tube is configured to be disengaged from the electrode mount after the device deploys the one or more electrodes superiorly away from the tube.

For some applications, an outer diameter of the tube is 2-6 mm.

For some applications, a length of the tube is 5-8.5 cm.

For some applications, the tube is steerable, and includes a deflecting mechanism configured to bend a distal end portion of the tube in at least one direction with respect to an axis of the tube, in order to facilitate superior deployment of the one or more electrodes away from the tube.

For some applications, the tube is shaped so as to define a distal end opening, and the one or more electrodes are deployable away from the tube via the distal end opening.

For some applications, the tube is unidirectionally steerable.

For some applications, the tube is deflectable at a deflection region of the tube that is 0.5-2.5 cm from a distal end of the tube.

For some applications, the tube is deflectable at a deflection region of the tube that is less than 6 cm from a proximal end of the tube.

For some applications, a distal end portion of the tube is configured to be curved when in an unconstrained resting state, in order to facilitate superior deployment of the one or more electrodes away from the tube.

For some applications, the device further includes a sheath, in which at least the distal end portion is removably disposed so as to constrain the distal end portion of the tube in a straightened state.

For some applications, the electrode mount is coupled to a distal end portion of the tube.

For some applications, the electrode mount is removably disposed within the tube, and is configured, upon deployment from the tube, to superiorly deploy the one or more electrodes and position the one or more electrodes against a wall of the nasal cavity for stimulating the SPG.

For some applications, the electrode mount is removably constrained within the tube in a constrained state, and is configured to expand to an expanded state after the deployment from the tube, so as to superiorly deploy the one or more electrodes and position the one or more electrodes against a wall of the nasal cavity for stimulating the SPG.

For some applications:
- the electrode mount includes an inflatable electrode mount,
- the one or more electrodes are coupled to an external surface of the inflatable electrode mount, and the electrode mount is configured, upon inflation of the inflatable electrode mount, to superiorly deploy the one or more electrodes and position the one or more electrodes against the wall of the nasal cavity for stimulating the SPG.

For some applications:
the inflatable electrode mount is removably disposed in the tube while the inflatable electrode mount is in an uninflated state, and
the inflatable electrode mount is configured, upon the deployment from the tube and the inflation of the inflatable electrode mount, to superiorly deploy the one or more electrodes and position the one or more electrodes against the wall of the nasal cavity for stimulating the SPG.

For some applications, the inflatable electrode mount, when inflated and unconstrained, has a long axis that is generally L-shaped.

For some applications, the inflatable electrode mount, when inflated and unconstrained, has a long axis that is arcuate.

For some applications, the inflatable electrode mount, when inflated and unconstrained, has a long axis that has a distal segment and a proximal segment that define an angle of 30-150 degrees therebetween.

For some applications, the electrode mount is coupled to a distal end portion of the tube.

For some applications, the electrode mount is elongate and is removably constrained coiled around a distal end portion of the tube, and is configured, upon being released from being constrained, to at least partially uncoil, so as to superiorly deploy the one or more electrodes and position the one or more electrodes against a wall of the nasal cavity for stimulating the SPG.

For some applications, the electrode mount includes a flexible wire, to which the one or more electrodes are fixed.

For some applications, the flexible wire is configured to be shaped as a loop upon deployment.

For some applications, the flexible wire is configured to be shaped as a curve upon deployment.

For some applications, the flexible wire is removably disposed within the tube, and is configured to be deployed from the tube via first and second side openings defined by the tube.

For some applications, the electrode mount includes one or more struts, to which the one or more electrodes are fixed.

For some applications, the one or more struts include a plurality of struts arranged as spokes radiating from a hub.

For some applications, the one or more struts include a plurality of struts arranged as a frame.

For some applications, the apparatus further includes a balloon, which is not fixed to the one or more struts, the balloon is arranged, so as to press the one or more struts into the wall of the nasal cavity upon inflation of the balloon.

For some applications, the one or more struts include a plurality of struts arranged on only one side of the balloon.

For some applications, the one or more struts include a plastically deformable material.

For some applications, the plastically deformable material includes a malleable material.

For some applications, the tube and the balloon are configured to be disengaged from the electrode mount after the device deploys the one or more electrodes superiorly away from the tube.

For some applications, the electrode mount includes the balloon.

For some applications, the tube is configured to be disengaged from the electrode mount, including from the balloon, after the device deploys the one or more electrodes superiorly away from the tube.

For some applications, the electrode mount includes a spring, to which the one or more electrodes are coupled.

For some applications, the spring is shaped so as to define undulations having proximal and distal peaks.

For some applications, the undulations surround an axis.

For some applications, the apparatus further includes a control unit including circuitry configured to drive the one or more electrodes to stimulate the SPG.

There is still further provided, in accordance with some applications of the present invention, a method for treating a patient in cardiac arrest or in an acute post-cardiac arrest phase, the method including:
coupling two or more electrodes to tissue of the patient in cardiac arrest or in an acute post-cardiac arrest phase; and
increasing cerebral blood flow (CBF) of the patient in cardiac arrest or in an acute post-cardiac arrest phase by activating a power source to drive the electrodes to apply current to a sphenopalatine ganglion (SPG) of the patient.

For some applications, coupling the electrodes to the tissue includes positioning the electrodes within a nose of the patient such that the electrodes are in position to stimulate the SPG.

For some applications, coupling the electrodes to the tissue includes positioning the electrodes on skin over a mandibular notch of the patient such that the electrodes are in position to stimulate the SPG.

For some applications, coupling the electrodes to the tissue includes positioning the electrodes against gingiva of the patient such that the electrodes are in position to stimulate the SPG.

For some applications, coupling the electrodes to the tissue includes positioning the electrodes against the hard palate of a mouth of the patient such that the electrodes are in position to stimulate the SPG.

For some applications, coupling the electrodes to the tissue includes coupling the electrodes to the tissue within 24 hours of an onset of the cardiac arrest.

For some applications, coupling the electrodes to the tissue includes coupling the electrodes to the tissue within 6 hours of an onset of the cardiac arrest.

For some applications:
the method further includes activating a defibrillator to apply an electric charge to a heart of the patient,
and activating the power source to drive the electrodes to apply current to the SPG of the patient includes activating the power source to drive the electrodes to apply current to the SPG after the activation of the defibrillator.

For some applications, activating the power source to drive the electrodes to apply current to the SPG after the activation of the defibrillator includes activating the power source to drive the electrodes to apply current to the SPG within 1 hour after the activation of the defibrillator.

There is further provided, in accordance with some applications of the present invention, a medical device including:
a defibrillator configured to apply an electric charge to a heart of a patient;
a sphenopalatine ganglion (SPG) stimulating device for stimulating an SPG of the patient via two or more electrodes configured to be coupled to tissue of the patient; and circuitry configured to drive the defibrillator and the SPG stimulating device such that when the circuitry is activated, the circuitry drives the defibrillator to apply an electric charge to the heart and thereafter drives the electrodes to apply current to the SPG of the patient.

There is further provided, in accordance with some applications of the present invention, a sphenopalatine ganglion (SPG) stimulating device for stimulating an SPG of a patient, the device including:

a sheath having a proximal end portion and a distal end portion, the distal end portion shaped to define at least one electrode opening;

a nasal stabilizer disposed around the sheath and configured to stabilize the sheath with respect to a nostril of a nose of the patient when the sheath is disposed within the nose;

an electrode mount, slidably disposed within the sheath; and at least one electrode coupled to the electrode mount and deployable out of the sheath through the at least one electrode opening to position the at least one electrode to stimulate the SPG.

For some applications, the sheath is flexible.

For some applications, the sheath includes silicone.

For some applications, a distance between the nasal stabilizer and the at least one electrode opening is 4-8 cm.

For some applications, an outer diameter of the nasal stabilizer is 3-15 mm greater than an outer diameter of the sheath.

For some applications, an outer diameter of the sheath is 3-8 mm.

For some applications, the device further includes a releasable pre-deployment lock, configured to prevent sliding of the electrode mount within the sheath.

For some applications, the at least one electrode is configured to curve away from a central longitudinal axis of the sheath during deployment of the at least one electrode.

For some applications, the nasal stabilizer is connected to the sheath.

For some applications, the nasal stabilizer is inseparable from the sheath without breaking a portion of the device.

For some applications, the at least one electrode includes a plurality of electrodes.

For some applications, the plurality of electrodes includes exactly three independently-addressable electrodes.

For some applications, the electrode mount further includes a plurality of flexible prongs, and each of the plurality of electrodes is coupled to a respective one of the flexible prongs.

For some applications, the at least one electrode is arranged such that distal motion of the electrode mount with respect to the sheath deploys the at least one electrode out of the sheath through the at least one electrode opening.

For some applications, the nasal stabilizer is arranged to remain in a same location with respect to the sheath during the distal motion of the electrode mount with respect to the sheath.

For some applications, the device further includes a releasable post-deployment lock, configured to prevent sliding of the electrode mount within the sheath following the distal motion of the electrode mount with respect to the sheath.

For some applications, the at least one electrode is arranged such that proximal motion of the sheath with respect to the electrode mount deploys the at least one electrode out of the sheath through the at least one electrode opening.

For some applications, the sheath is arranged to slide proximally with respect to the nasal stabilizer during the proximal motion of the sheath with respect to the electrode mount.

For some applications, the sheath is shaped to define a longitudinal slit on a lateral side of the sheath, and the nasal stabilizer is connected to the electrode mount through the longitudinal slit.

For some applications, the longitudinal slit extends from a distal end of the sheath to a location along the sheath that is proximal to the nasal stabilizer.

For some applications, the longitudinal slit extends from the distal end of the sheath to a proximal end of the sheath.

For some applications, the device further includes an implant handle for stabilizing the electrode mount during the proximal motion of the sheath, the implant handle protruding from the electrode mount through the longitudinal slit at a location along the electrode mount that is proximal to the nasal stabilizer.

For some applications, the device further includes an insulating coating that coats the at least one electrode, the insulating coating leaving at least one exposed region of the at least one electrode configured for driving current into tissue of the patient.

For some applications, the insulating coating leaves a plurality of exposed regions of the at least one electrode for driving current into tissue of the patient.

For some applications, the device further includes a sensor coupled to the sheath and configured to sense a physiological response of the patient to stimulation of the SPG.

For some applications, the sensor is a Doppler flowmetry sensor.

For some applications, the sensor is fixed to the sheath.

For some applications, the device further includes a sensor coupled to the electrode mount and configured to sense a physiological response of the patient to stimulation of the SPG.

For some applications, the sensor is fixed to a lateral side of the electrode mount.

For some applications, the sheath is shaped to define at least one sensor hole, and the sensor fixed to the electrode mount is configured to sense the physiological response of the patient through the sensor hole.

For some applications, the sensor is a Doppler flowmetry sensor.

For some applications, the device further includes a camera coupled to the sheath and configured to facilitate navigation of the sheath toward the SPG.

For some applications, the camera is fixed to the sheath.

For some applications, the device further includes a camera fixed to a distal end of the electrode mount, configured to facilitate navigation of the distal end of the electrode mount toward the SPG.

For some applications, the device further includes a control unit including a battery and circuitry and configured to drive the at least one electrode to stimulate the SPG.

For some applications, the control unit is wearable.

For some applications, the device further includes a mandibular notch electrode coupled to the control unit and couplable to skin over a mandibular notch of the patient, and the control unit is configured to drive the at least one electrode to stimulate the SPG by driving a current between the at least one electrode and the mandibular notch electrode.

For some applications, the device further includes a gingival electrode frame and a gingival electrode mounted on the gingival frame, the gingival electrode coupled to the control unit and couplable, using the gingival electrode frame, to gingiva of the patient, and the control unit is configured to drive the at least one electrode to stimulate the SPG by driving a current between the at least one electrode and the gingival electrode.

For some applications, the device further includes a dental arch electrode frame configured to be mounted to a dental arch of the patient and at least one greater palatine foramen (GPF) electrode coupled to the dental arch electrode frame, the at least one GPF electrode coupled to the control unit and couplable, using the dental arch electrode frame, to a hard palate of the patient over a GPF of the patient, and the control unit is configured to drive the at least one electrode to stimulate the SPG by driving a current between the at least one electrode and the at least one GPF electrode.

For some applications, the device further includes a greater palatine foramen electrode frame and a greater palatine foramen electrode mounted on the greater palatine foramen electrode frame, the greater palatine foramen electrode coupled to the control unit and couplable, using the greater palatine foramen electrode frame, to tissue over a greater palatine foramen of the patient, and the control unit is configured to drive the at least one electrode to stimulate the SPG by driving a current between the at least one electrode and the greater palatine foramen electrode.

For some applications, the device further includes a sensor configured to sense a physiological response of the patient to stimulation of the SPG and to send to the control unit a signal indicative of the physiological response.

For some applications, the at least one electrode includes a plurality of electrodes, and the control unit is configured to designate at least one of the plurality of electrodes to exclude from use for stimulating the SPG in response to the signal.

For some applications, the sensor is a Doppler flowmetry sensor.

For some applications, the Doppler flowmetry sensor is configured to be coupled to skin of the patient over a carotid artery of the patient.

There is further provided, in accordance with some applications of the present invention, a sphenopalatine ganglion (SPG) stimulating device for stimulating an SPG of a patient, the device including:
  a flexible housing having a proximal end portion and a distal end portion, wherein the distal end portion is (a) shaped to define a plurality of electrode arms configured to open outward away from a central longitudinal axis of the housing during deployment of the electrode arms, each electrode arm coupled to the flexible housing at a proximal end of the electrode arm, and (b) configured to be placed within a nose of a patient;
  a deployment actuator configured to actuate the deployment of the electrode arms;
  a camera (a) disposed at the distal end portion of the housing prior to the deployment of the electrode arms, wherein proximal motion of the camera toward the proximal end portion of the housing is associated with the deployment of the electrode arms, and (b) configured to facilitate navigation of the housing toward the SPG; and
  for each electrode arm, at least one electrode coupled to the electrode arm such that when the distal end portion is placed within the nose and the electrode arm is deployed, the at least one electrode is positioned to stimulate the SPG.

For some applications, the plurality of electrode arms includes exactly three electrode arms.

There is further provided, in accordance with some applications of the present invention, a sphenopalatine ganglion (SPG) stimulating device for stimulating an SPG of a patient, the device including:
  a flexible tube configured for placement within a nose of a patient and having a proximal end portion and a distal end portion, (a) the distal end portion including at least one inflatable electrode mount, and (b) the proximal end portion including an inflation actuator via which the at least one inflatable electrode mount is inflatable; and
  at least one electrode coupled to the at least one inflatable electrode mount such that when the device is placed within the nose and the at least one inflatable electrode mount is inflated, the at least one electrode is positioned to stimulate the SPG.

For some applications, the device further includes an inflatable nasal stabilizer disposed around the flexible tube and configured to stabilize the flexible tube with respect to a nostril of the nose when the flexible tube is disposed within the nose and the inflatable nasal stabilizer is inflated.

For some applications, the at least one inflatable electrode mount includes a plurality of inflatable electrode mounts positioned circumferentially around the distal end portion of the flexible tube, and the at least one electrode includes a respective at least one electrode coupled to each of the plurality of inflatable electrode mounts.

For some applications, the plurality of inflatable electrode mounts includes exactly three inflatable electrode mounts.

For some applications, the at least one inflatable electrode mount includes an inflatable electrode balloon, and the at least one electrode includes a plurality of electrodes positioned circumferentially around the inflatable balloon such that when the device is placed within the nose and the inflatable electrode balloon is inflated, at least one of the plurality of electrodes is positioned to stimulate the SPG.

For some applications, the at least one inflatable electrode mount is circular or elliptical in cross-section perpendicular to an axis of the flexible tube, and the at least one electrode comprises a plurality of electrodes positioned circumferentially around the at least one inflatable electrode mount such that when the device is placed within the nose and the at least one inflatable electrode mount is inflated, at least one of the plurality of electrodes is positioned to stimulate the SPG.

For some applications, the at least one electrode comprises a single inflatable electrode mount.

For some applications, the inflatable electrode mount, when inflated and unconstrained, has a long axis that is generally L-shaped.

For some applications, the inflatable electrode mount, when inflated and unconstrained, has a long axis that is arcuate.

For some applications, the inflatable electrode mount, when inflated and unconstrained, has a long axis that has a distal segment and a proximal segment that define an angle of 30-150 degrees therebetween.

The present invention will be more fully understood from the following detailed description of applications thereof, taken together with the drawings, in which:

BRIEF DESCRIPTION OF THE DRAWINGS

FIG. 3 is a schematic illustration of a combination of a defibrillator and an SPG stimulating device, in accordance with some applications of the present invention;

FIGS. 4A-B show the SPG stimulating device placed within a nose of a patient and connected to a control unit, in accordance with some applications of the present invention;

FIGS. 12A-B and 13 are schematic illustrations of different variations of a nasal SPG stimulating device, in accordance with some applications of the present invention;

FIGS. 14A-C are schematic illustrations of a particular variation of a nasal SPG stimulating device, in accordance with some applications of the present invention;

FIGS. 29A-B are schematic illustrations of the SPG stimulating device of FIGS. 28A-B, in accordance with an application of the present invention;

FIGS. 30A-C are schematic illustrations of another SPG stimulating device for stimulating the SPG from within the nasal cavity, in accordance with an application of the present invention;

FIGS. 45A and 45B are schematic illustrations of a configuration of an electrode mount, in accordance with an application of the present invention;

FIG. 46 is a schematic illustration of an SPG stimulating device for stimulating the SPG from within the nasal cavity, in accordance with an application of the present invention;

DETAILED DESCRIPTION

Figure 1:
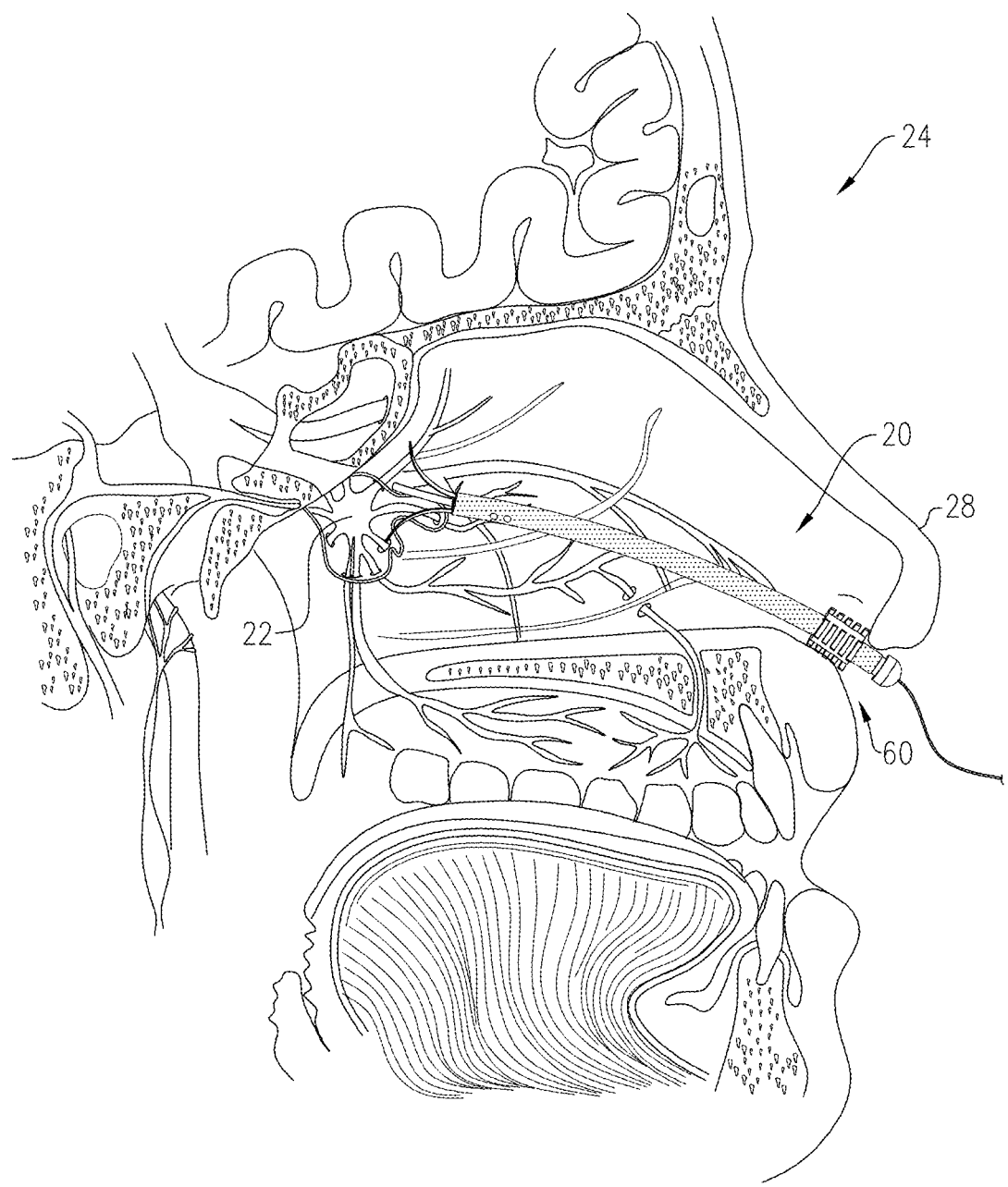
FIG. 1 is a schematic illustration of an SPG stimulating device for stimulating an SPG of a patient, in accordance with some applications of the present invention.

Reference is now made to FIG. 1, which is a schematic illustration of an SPG stimulating device 20 for stimulating an SPG 22 of a patient 24, in accordance with some applications of the present invention. For some applications, stimulating SPG 22 may be used as a method for treating a patient in cardiac arrest or in an acute post-cardiac arrest phase. The method for treatment typically includes coupling two or more electrodes to tissue of patient 24 in cardiac arrest or in an acute post-cardiac arrest phase, and increasing cerebral blood flow (CBF) of patient 24 by activating a power source (such as battery 96 inside control unit 26 shown in FIGS. 4A-B) to drive the electrodes to apply current to SPG 22 of patient 24. It is noted that the two or more electrodes may be, for example, any of the electrode embodiments described herein, as well as any electrodes described with respect to other stimulating devices configured to stimulate the SPG of a patient (e.g., as described in U.S. Ser. No. 18/229,379 to Gross et al., now abandoned, which is incorporated herein by reference). For some applications, the electrodes are coupled to the tissue of patient 24 within 24 hours, e.g., within 6 hours, of an onset of the cardiac arrest.

For clarity of illustration, SPG stimulation is generally shown and described with respect to a single SPG 22. In any of the configurations described herein, the SPG stimulation may be applied to either a single SPG (the left or the right SPG) or both SPGs, in which case many of the elements of the system are duplicated for the left and right sides of the head.

For some applications, such as is shown for example in FIGS. 1, 3, and 4, the tissue is within a nose 28 of patient 24, and coupling the electrodes to the tissue is done by positioning the electrodes within nose 28 of patient 24 such that the electrodes are in position to stimulate SPG 22 of patient 24. It is noted that positioning the electrodes within nose 28 may be done using electrodes 30 of any of the nasal SPG stimulating devices 20 described herein.

Figure 2:
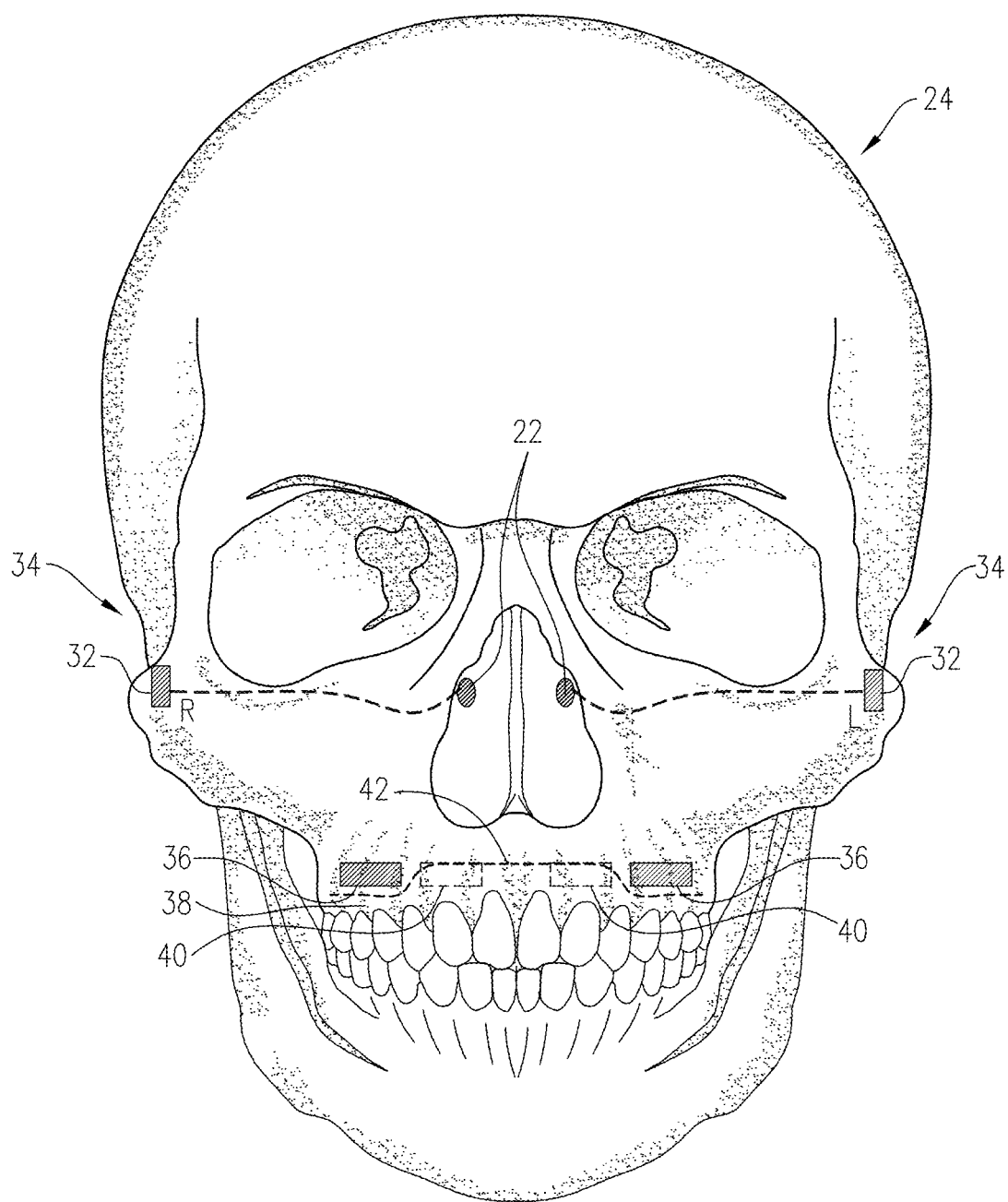
FIG. 2 illustrates non-nasal sites for stimulating the SPG of the patient, in accordance with some applications of the present invention.

Reference is now made to FIG. 2, which illustrates non-nasal sites for stimulating SPG 22 of patient 24, in accordance with some applications of the present invention. For some applications, coupling the electrodes to the tissue comprises positioning mandibular notch electrodes 32 on skin over a mandibular notch 34 of patient 24 (such as is shown in FIG. 8B) such that electrodes 32 are in position to stimulate SPG 22. Alternatively or additionally, coupling the electrodes to the tissue comprises positioning gingival electrodes 36 against gingiva 38 of patient 24 (such as is shown in FIGS. 9B-C) such that electrodes 36 are in position to stimulate SPG 22. Alternatively or additionally, coupling the electrodes to the tissue comprises positioning greater palatine foramen (GPF) electrodes 40 against a hard palate 42 (such as is shown in FIG. 10B) of a mouth of patient 24 such that electrodes 40 are in position to stimulate SPG 22.

Reference is now made to FIG. 3, which is a schematic illustration of a combination of a defibrillator and SPG stimulating device, in accordance with some applications of the present invention. For some applications, the method of treatment of patient 24 in cardiac arrest or in an acute post-cardiac arrest phase further includes activating a defibrillator 44 to apply an electric charge to a heart 46 of patient 24. Typically, defibrillator 44 is activated to apply the electric charge to heart 46 and the power source (e.g., circuitry 48 as shown in FIG. 3, or battery 96 in control unit 26 as shown in FIGS. 4A-B) is activated to drive the electrodes (e.g., electrodes 30, electrodes 32, electrodes 36, electrodes 40, and/or electrodes 160) to apply current to SPG 22 after the activation of defibrillator 44, e.g., within 1 hour after the activation of defibrillator 44. (For some applications, the current is applied to SPG 22 shortly before activation of defibrillator 44.)

For some applications, a medical device 43 may be used that comprises a defibrillator and an SPG stimulator, for example as shown in FIG. 3. Medical device 43 includes defibrillator 44 configured to apply an electric charge to heart 46 of patient 24, SPG stimulating device 20 for stimulating an SPG of patient 24 via two or more electrodes 30, and circuitry 48 configured to drive defibrillator 44 and SPG stimulating device 20 such that when circuitry 48 is activated, circuitry 48 drives defibrillator 44 to apply an electric charge to heart 46 and thereafter drives the electrodes to apply current to SPG 22 of patient 24. It is noted that circuitry 48 for driving defibrillator 44 and SPG stimulating device 20 may be all in one housing (such as is shown in FIG. 3), or respective parts of circuitry 48 for driving defibrillator 44 and SPG stimulating device 20, respectively, may be in separate housings. It is noted that SPG stimulating device is shown as a nasal SPG stimulating device in FIG. 3 by way of example only (any of the embodiments described herein for an SPG stimulating device may be used, as well as any other electrodes or stimulating device configured to stimulate the SPG of a patient). It is also noted that while FIG. 3 shows medical device 43 comprising a defibrillator and SPG stimulating device, the method of first activating a defibrillator to apply an electric charge to the heart of the patient and thereafter applying stimulation to the SPG of the patient may be performed using separate defibrillator and SPG stimulating devices.

For some applications, alternatively or additionally to increasing CBF to treat a patient in cardiac arrest or in an acute post-cardiac arrest phase, SPG stimulating device may be used for any of the following:
- patients who have had an ischemic stroke-either pre/during/post a thrombectomy or for patients who are not eligible for thrombectomy,
- patients who have vasospasm, e.g., post subarachnoid hemorrhage,
- stroke rehabilitation,
- prevention and treatment of post-surgery cognitive decline,
- treatment of dementia, such as vascular dementia,
- treatment post transient ischemic attack (TIA),
- treatment of Alzheimer's disease,
- stroke prevention post transcatheter aortic valve implantation (TAVI), or
- increasing permeability of the Blood Brain Barrier (BBB).

Reference is now made to FIGS. 4A-B, which show SPG stimulating device 20 placed within nose 28 of patient 24 and connected to a control unit 26 (further described hereinbelow), in accordance with some applications of the present invention. It is noted that SPG stimulating device 20 shown in FIGS. 4A-B may be any of the variations of SPG stimulating device 20 described hereinbelow.

Reference is now made to FIGS. 5A-C and 6A-B, which are schematic illustrations of different variations of a nasal SPG stimulating device 20, in accordance with some applications of the present invention. For some applications, SPG stimulating device 20 includes the following:
- a sheath 50 having a proximal end portion 52 and a distal end portion 54, distal end portion 54 shaped to define at least one electrode opening 56 (shown in FIG. 5B and FIG. 6B);
- a nasal stabilizer 58 disposed around sheath 50 and configured to stabilize sheath 50 with respect to a nostril 60 (shown in FIG. 1) of nose 28 of patient 24 when sheath 50 is disposed within nose 28 (such as is shown in FIGS. 4A-B);
- an electrode mount 62, slidably disposed within sheath 50; and
- at least one electrode 30 coupled to electrode mount 62 and deployable out of sheath 50 through at least one electrode opening 56 to position at least one electrode 30 to stimulate SPG 22.

Typically, sheath 50 is flexible. For example, sheath 50 may be made of a flexible polymer, e.g., silicone. For some applications, dimensions of SPG stimulating device 20 may include one or more of the following:
- a distance D1 (shown in FIGS. 5A and 6A) between nasal stabilizer 58 and at least one electrode opening 56 is at least 4 cm and/or less than 8 cm,
- an outer diameter D2 (shown in FIGS. 5A and 6A) of sheath 50 is at least 3 mm and/or less than 8 mm, and
- an outer diameter D3 (shown in FIGS. 5A and 7B) of nasal stabilizer 58 is at least 3 mm and/or less than 15 mm.

Figure 5A:
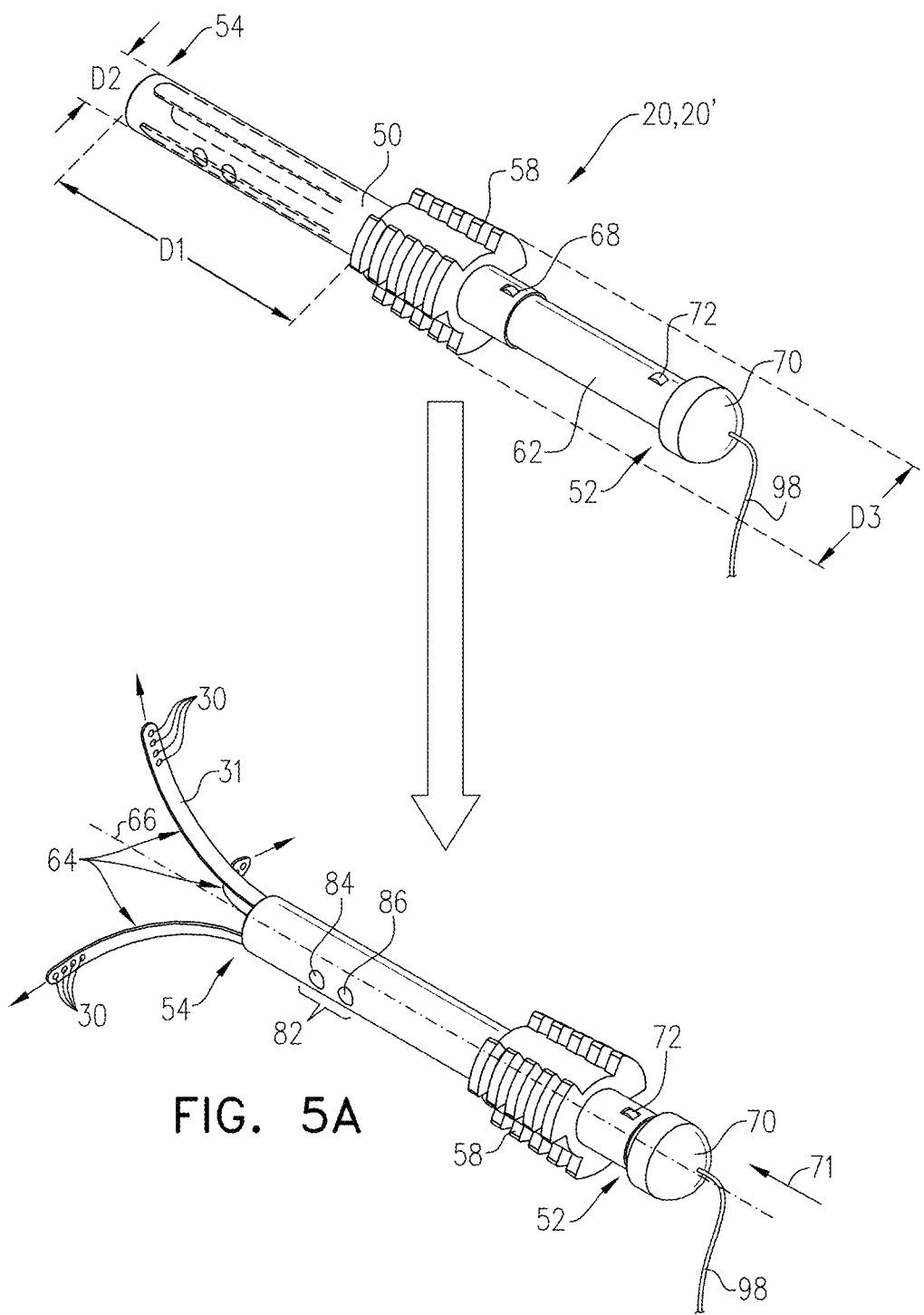
FIGS. 5A-C and 6A-B are schematic illustrations of different variations of a nasal SPG stimulating device, in accordance with some applications of the present invention.

For some applications, SPG stimulating device 20 has a plurality of electrodes 30, e.g., exactly three independently-addressable electrodes 30. For some applications, electrode mount 62 has a plurality of flexible prongs 64, with each of the plurality of electrodes 30 coupled to a respective one of flexible prongs 64. During deployment of electrode(s) 30, electrode(s) 30 may curve away from a central longitudinal axis 66 of sheath 50, e.g., flexible prong(s) 64 to which electrode(s) 30 are coupled may curve away from central longitudinal axis 66 during deployment of electrode(s) 30 out of sheath 50 (such as is shown in FIG. 5A). For some applications, such as is shown in FIG. 5A, a plurality of electrodes 30, e.g., gold plated nitinol electrodes, are coupled to each flexible prong 64. Alternatively, for some applications, such as is shown in FIG. 6B, a single electrode 30, e.g., gold plated nitinol electrode, is coupled to each flexible prong 64.

For some applications, an insulating coating 31 coats electrode(s) 30, the insulating coating leaving at least one exposed region, e.g., a plurality of exposed regions, of electrode(s) 30 configured for driving current into tissue of patient 24. For example, a traditional electrode lead may be used comprising platinum-iridium electrodes that are placed along an insulating lead and are all connected to an inner conductive wire of the lead.

For some applications, SPG stimulating device 20 includes a releasable pre-deployment lock 68 that prevents electrode mount 62 from sliding within sheath 50. This allows SPG stimulating device 20 to be positioned within nose 28 of patient 24 without the medical practitioner needing to worry about electrode mount 62 sliding within sheath 50. Once SPG stimulating device 20 is correctly positioned within nose 28, the medical practitioner can unlock releasable pre-deployment lock 68 and slidably deploy electrode(s) 30, as further described hereinbelow. Releasable pre-deployment lock 68 may be any of kind of lock that holds electrode mount 62 stationary with respect to sheath 50 and can be released to enable electrode mount 62 to slide with respect to sheath 50. For example, releasable pre-deployment lock 68 may include a small hole in sheath 50 and a depressible protrusion on electrode mount 62 configured to protrude from electrode mount 62 in the absence of an external force pushing the protrusion down; in a locked state the protrusion protrudes through the hole in sheath 50 and can be depressed so as to enable electrode mount 62 to slide.

Figure 5B:
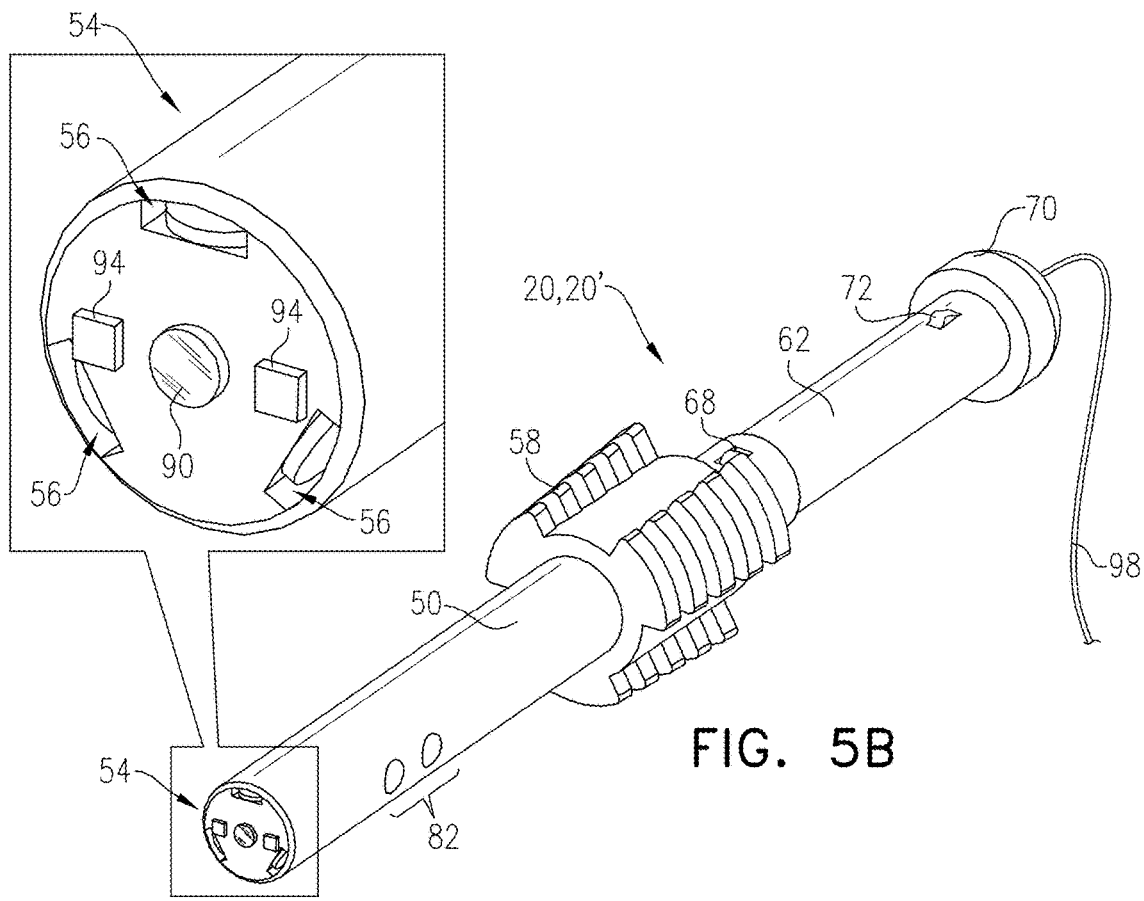
Figure 5C:
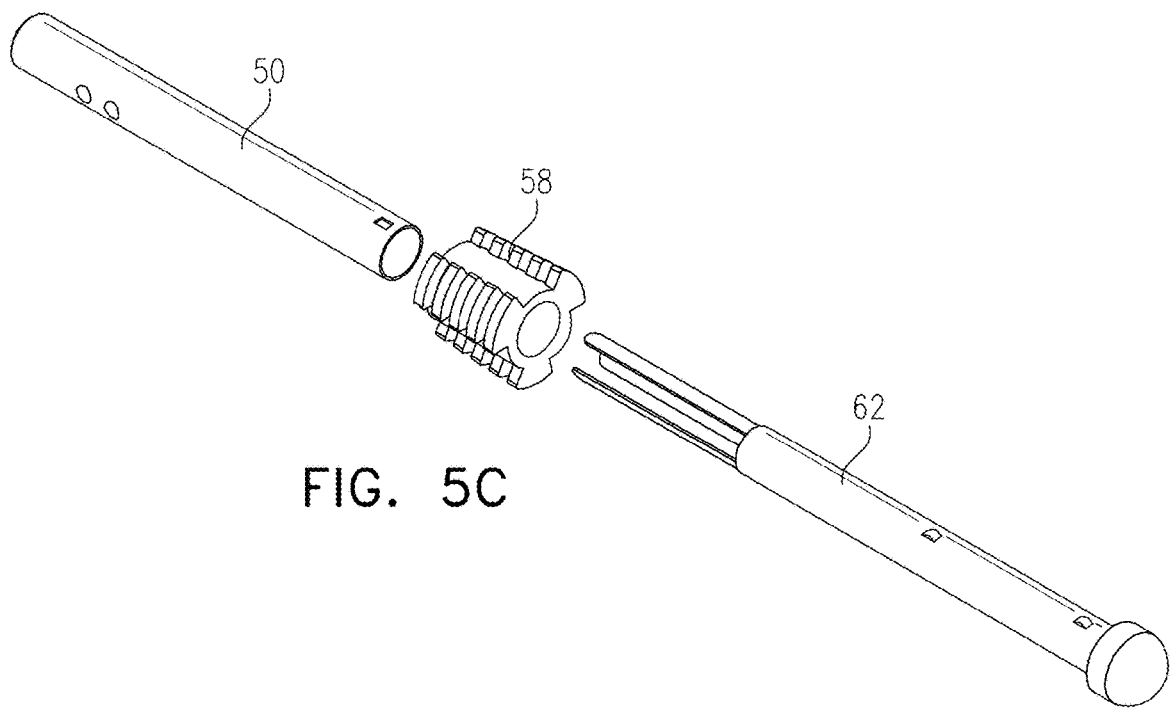

Reference is now made specifically to FIGS. 5A-C, which depict a SPG stimulating device 20', which is an implementation of SPG stimulating device 20. Electrode(s) 30 of SPG stimulating device 20' are arranged such that distal motion of electrode mount 62 with respect to sheath 50 deploys electrode(s) 30 out of sheath 50 through electrode opening(s) 56. After the medical practitioner has positioned SPG stimulating device 20' within nose 28 of patient 24, the medical practitioner pushes on a proximal end 70 of electrode mount 62 in order to slide electrode mount 62 distally with respect to sheath 50. FIG. 5A depicts the distal motion (represented by arrow 71) of electrode mount 62 with respect to sheath 50. Nasal stabilizer 58 is arranged to remain in a same location with respect to sheath 50 during the distal motion of electrode mount 62 with respect to sheath 50. For some applications, nasal stabilizer 58 is connected to sheath 50, e.g., nasal stabilizer 58 may be inseparable from sheath 50 without breaking a portion of the device or is otherwise not intended to be separated from sheath 50 during a medical procedure. For illustrative purposes, FIG. 5C shows an exploded view of sheath 50, nasal stabilizer 58, and electrode mount 62.

For some applications, SPG stimulating device 20' further includes a releasable post-deployment lock 72 configured to prevent sliding of electrode mount 62 within sheath 50 following the distal motion of electrode mount 62 with respect to sheath 50. This prevents electrode(s) 30 from moving within nose 28 of patient 24 once they have been deployed and are in position to stimulate SPG 22 of patient 24. Releasable post-deployment lock 72 may be the same type of lock as releasable pre-deployment lock 68 or may be a different type of lock. In order to remove SPG stimulating device 20' from within nose 28 of patient 24, releasable post-deployment lock 72 is released and electrode mount 62 is pulled proximally by proximal end 70 of electrode mount 62 in order to pull electrode(s) 30 back into sheath 50. Releasable pre-deployment lock 68 is then optionally locked again and SPG stimulating device 20' can be pulled out of nose 28 of patient 24.

Figure 6A:
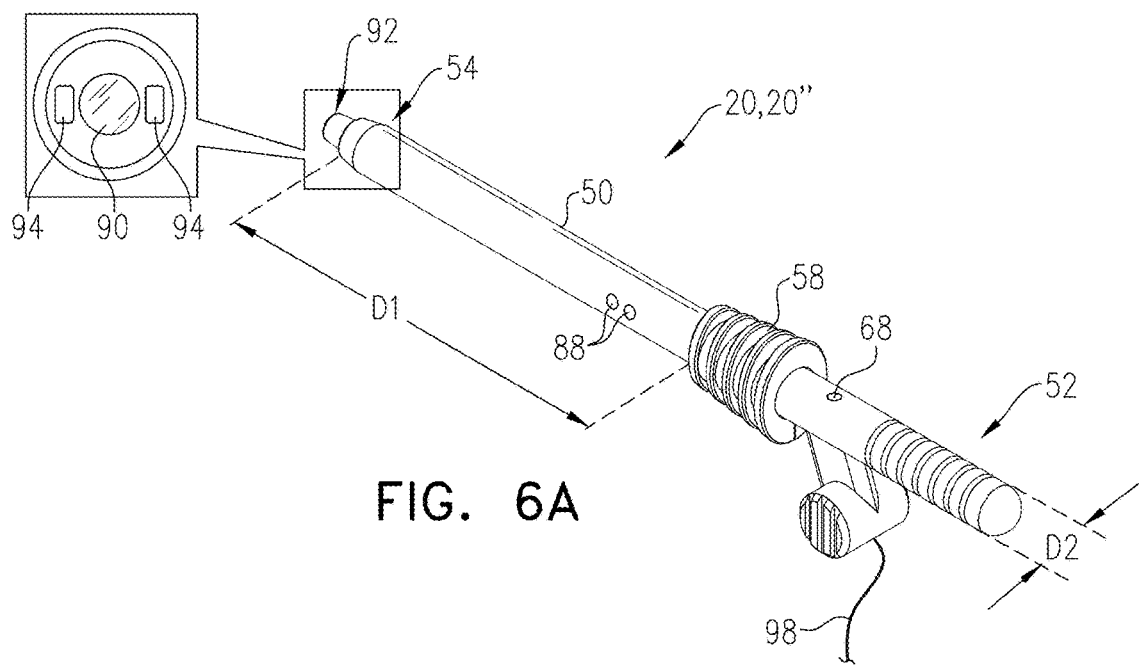
Figure 6B:
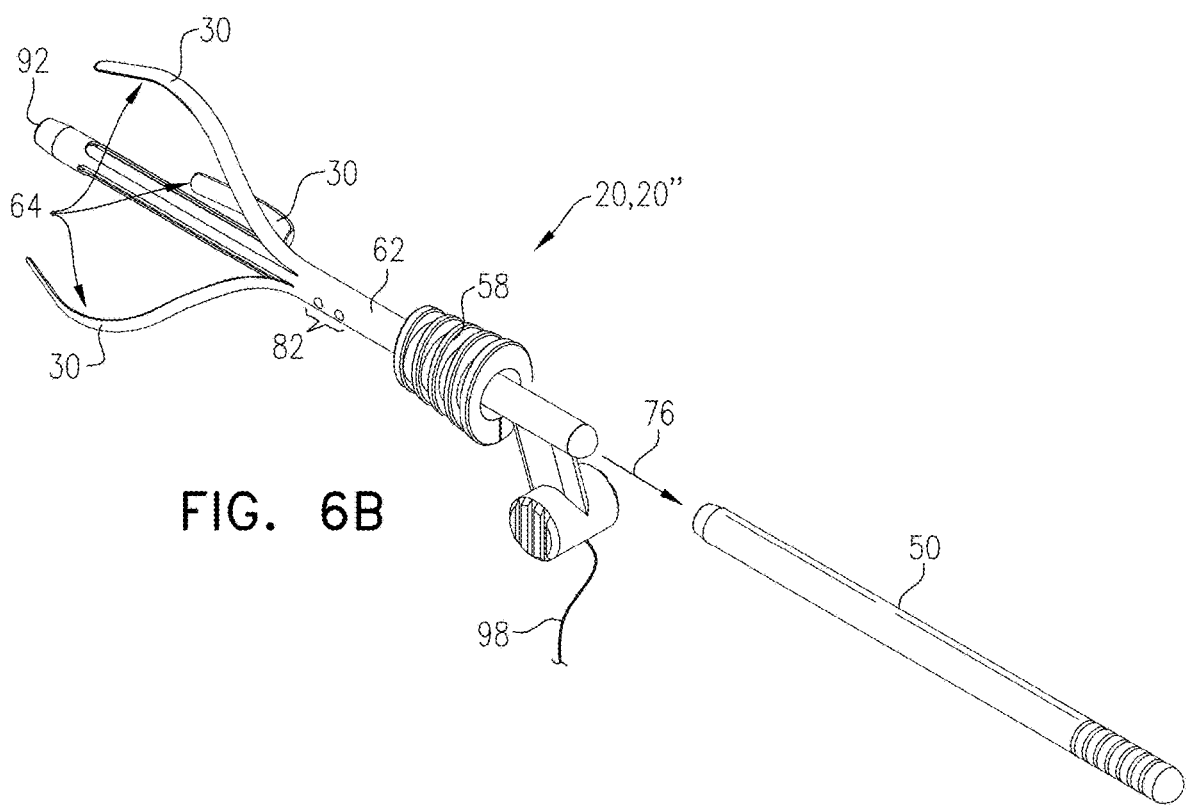

Reference is now made specifically to FIGS. 6A-B, which depict an SPG stimulating device 20'', which is an implementation of SPG stimulating device 20, in accordance with some applications of the present invention. Electrode(s) 30 are arranged such that proximal motion of sheath 50 with respect to electrode mount 62 deploys electrode(s) 30 out of sheath 50 through electrode opening 56. After the medical practitioner has positioned SPG stimulating device 20'' within nose 28 of patient 24, the medical practitioner releases releasable pre-deployment lock 68 and pulls on proximal end portion 52 of sheath 50 in order to slide sheath 50 proximally off electrode mount 62, as illustrated by arrow 76.

Figure 7A:
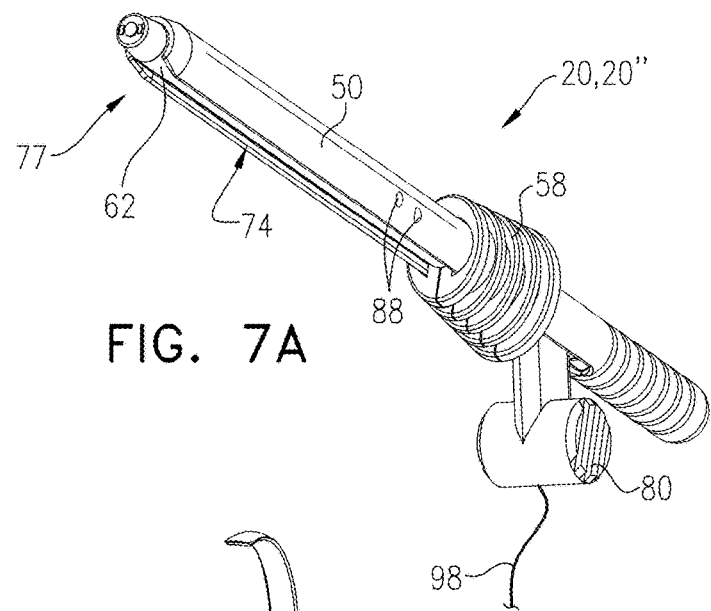
FIGS. 7A-C show various views of the SPG stimulating device of FIGS. 6A-B, in accordance with some applications of the present invention.
Figure 7B:
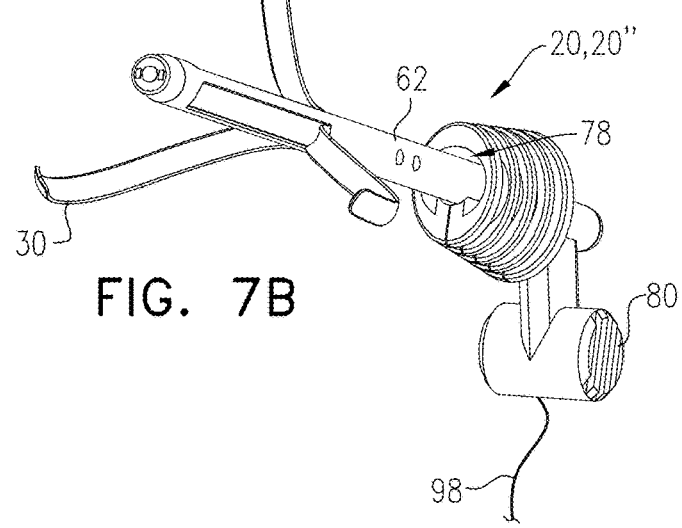
Figure 7C:
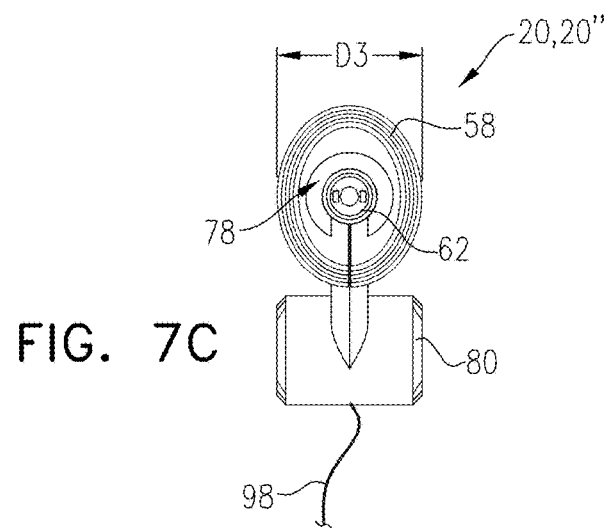

Reference is now made to FIGS. 7A-C, which show various views of SPG stimulating device 20'', in accordance with some applications of the present invention. Sheath 50 is arranged to slide proximally with respect to nasal stabilizer 58 during the proximal motion of sheath 50 with respect to electrode mount 62. As illustrated in FIG. 6B, nasal stabilizer 58 remains in place to stabilize SPG stimulating device 20'' within nose 28 of patient 24 after sheath 50 has been removed in order to deploy electrode(s) 30. This is achieved by sheath 50 having a longitudinal slit 74 on a lateral side of sheath 50 and nasal stabilizer 58 being connected to electrode mount 62 through the longitudinal slit. As sheath 50 is pulled proximally, the portion of nasal stabilizer 58 that is connected to electrode mount 62 slides through longitudinal slit 74, allowing sheath 50 to be removed. Typically, longitudinal slit 74 extends from a distal end 77 of sheath 50 to a location along sheath 50 that is proximal to nasal stabilizer 58 (such as is shown in FIG. 7A). For some applications, longitudinal slit 74 extends from distal end 77 of sheath 50 to a proximal end of sheath 50 (configuration not shown). For some applications, SPG stimulating device 20'' further includes an implant handle 80 for stabilizing electrode mount 62 during the proximal motion of sheath 50. Implant handle 80 protrudes from electrode mount 62 through longitudinal slit 74 at a location along electrode mount 62 that is proximal to nasal stabilizer 58.

FIGS. 7B-C show different perspective views of the connection between nasal stabilizer 58 and electrode mount 62 of SPG stimulating device 20''. As further illustrated by FIGS. 7B-C, except at the circumferential location at which nasal stabilizer 58 is connected to electrode mount 62, there is a radial gap 78 between nasal stabilizer 58 and electrode mount 62 that allows the medical practitioner to slide sheath 50 back onto electrode mount 62 in a distal direction in order to reposition electrode(s) 30 within sheath 50. Releasable pre-deployment lock 68 is then optionally locked again, and SPG stimulating device 20'' can be pulled out of nose 28 of patient 24.

Reference is again made to FIGS. 5A-C and 6A-B. For some applications, SPG stimulating device 20 includes a sensor 82 configured to sense a physiological response of patient 24 to stimulation of SPG 22. For some applications, sensor 82 is a Doppler flowmetry sensor including a laser light source 84, e.g., fiber-optic laser, and a photodetector 86, e.g., an optical fiber that collects and guides light to a photodetector, to measure light that was emitted by laser light source 84 and reflected back from tissue of patient 24. For some applications, such as for SPG stimulating device 20' shown in FIGS. 5A-C, sensor 82 is coupled to sheath 50, e.g., fixed to sheath 50. Alternatively, for some applications, such as for SPG stimulating device 20'' shown in FIGS. 6A-B, sensor 82 is coupled to electrode mount 62, e.g., fixed to a lateral side of electrode mount 62, and sheath 50 is shaped to define at least one sensor hole 88 through which sensor 82 senses the physiological response of patient 24.

Typically, SPG stimulating device 20 includes a camera 90, e.g., a micro camera, or a fiber-optic camera, to facilitate navigation of the device toward SPG 22. For some applications, such as for SPG stimulating device 20' shown in FIGS. 5A-C, camera 90 is coupled to sheath 50, e.g., fixed to sheath 50, at a distal end of sheath 50 (shown in FIG. 5B) and is configured to facilitate navigation of sheath 50 toward SPG 22. Alternatively, for some applications, such as for SPG stimulating device 20'' shown in FIGS. 6A-B, camera 90 is fixed to a distal end 92 of electrode mount 62 (shown in FIG. 6A) in order to facilitate navigation of distal end 92 of electrode mount 62 toward SPG 22. Typically, one or more light sources 94 (e.g., LED light sources) are positioned near camera 90 in order to provide illumination for camera 90.

Reference is again made to FIGS. 4A-B. Typically, SPG stimulating device 20 has a control unit 26. Control unit 26 typically has a battery 96 and is configured to drive electrode(s) 30 to stimulate SPG 22. For some applications, control unit 26 is wearable, e.g., coupled to a body of patient 24 using an adhesive, or worn around the patient's neck on a strap. Electrode(s) 30 of SPG stimulating device 20 are connected to control unit 26 via electrode leads 98 (shown in FIGS. 5A-C, 6A-B, and 7A-C). For some applications, control unit 26 has Bluetooth capabilities allowing control unit 26 to be controlled by a wireless device, such as a tablet or a smart phone, and for data from control unit 26 to be stored in a cloud-based database. Similarly to sensor 82 described hereinabove, for some applications, SPG stimulating device 20 further includes a sensor 100 that is not disposed on SPG stimulating device itself and is configured to sense a physiological response of patient 24 to stimulation of SPG 22 and to send to control unit 26 a signal indicative of the physiological response. For example, sensor 100 may be a Doppler flowmetry sensor, e.g., a Doppler flowmetry sensor coupled to skin of patient 24 over a carotid artery of patient 24 (such as is shown in FIG. 4B). For some applications, SPG stimulating device 20 has a plurality of electrodes 30 and control unit 26 is configured to designate at least one of the plurality of electrodes to exclude from use for stimulating SPG 22 in response to the signal from sensor 100, e.g., in response to determining that the excluded has no desired effect or less of a desired effect on the patient.

Figure 8A:
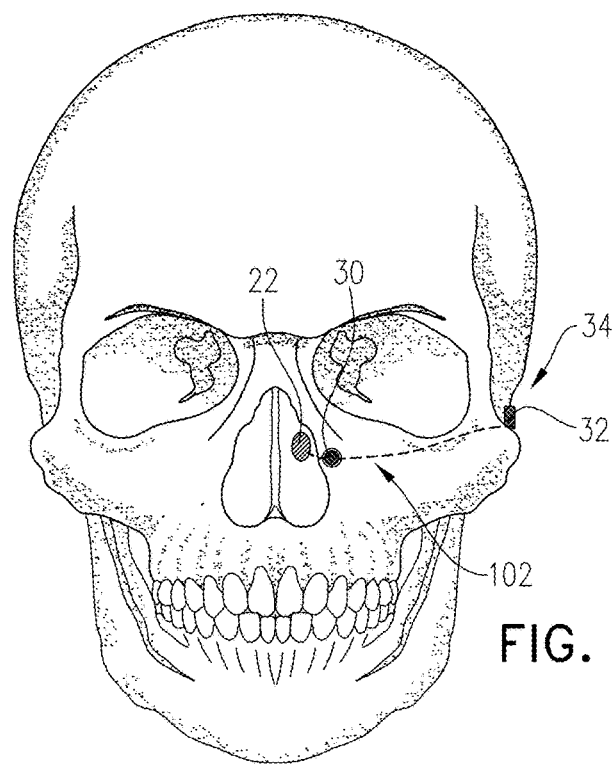
FIGS. 8A-B, 9A-C, and 10A-B show a SPG stimulating device comprising electrodes placed at non-nasal locations, in accordance with some applications of the present invention.
Figure 8B:
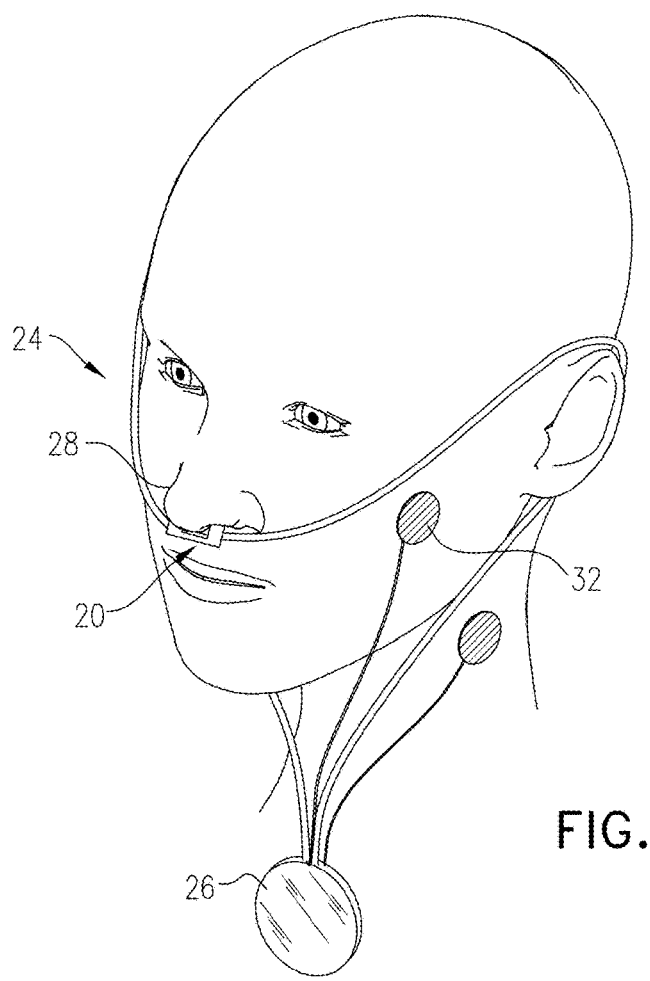
Figure 9C:
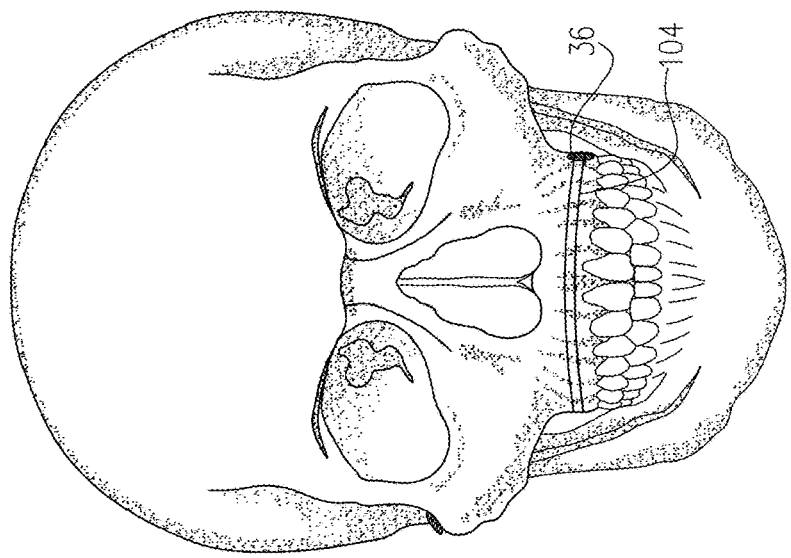
Figure 9B:
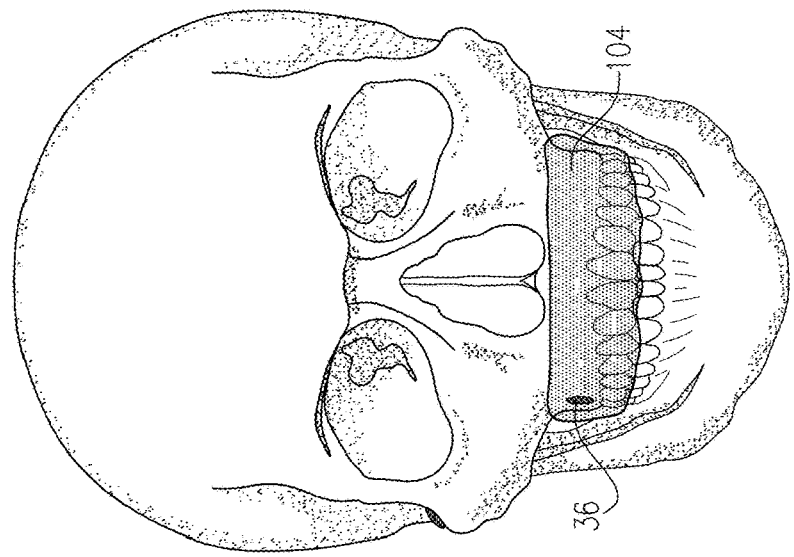

Reference is now made to FIGS. 8A-B, which show SPG stimulating device 20 in combination with at least one mandibular notch electrode 32 coupled to control unit 26 and coupled to skin over mandibular notch 34 of patient 24, in accordance with some applications of the present invention. Control unit 26 drives electrode(s) 30 to stimulate SPG 22 by driving a current between electrode(s) 30 and mandibular notch electrode 32 (as illustrated by dashed current path 102).

Figure 9A:
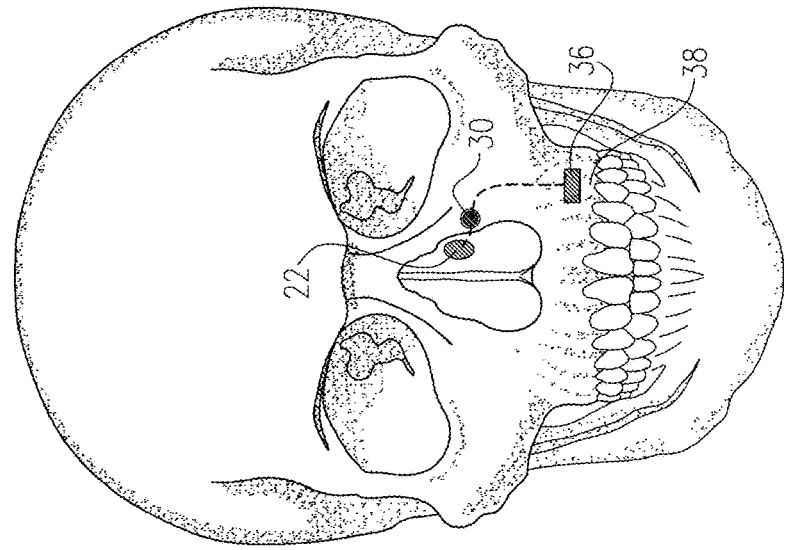

Reference is now made to FIGS. 9A-C, which show SPG stimulating device 20 in combination with at least one gingival electrode 36 mounted on a gingival electrode frame 104, in accordance with some applications of the present invention. Gingival electrode 36 is coupled to control unit 26 and is couplable, using gingival electrode frame 104, to gingiva 38 of patient 24. Control unit 26 drives electrode(s) 30 to stimulate SPG 22 by driving a current between electrode(s) 30 and gingival electrode 36 (as illustrated by dashed current path 106). FIGS. 9B-9C show different examples of gingival electrode frame 104.

Figure 10A:
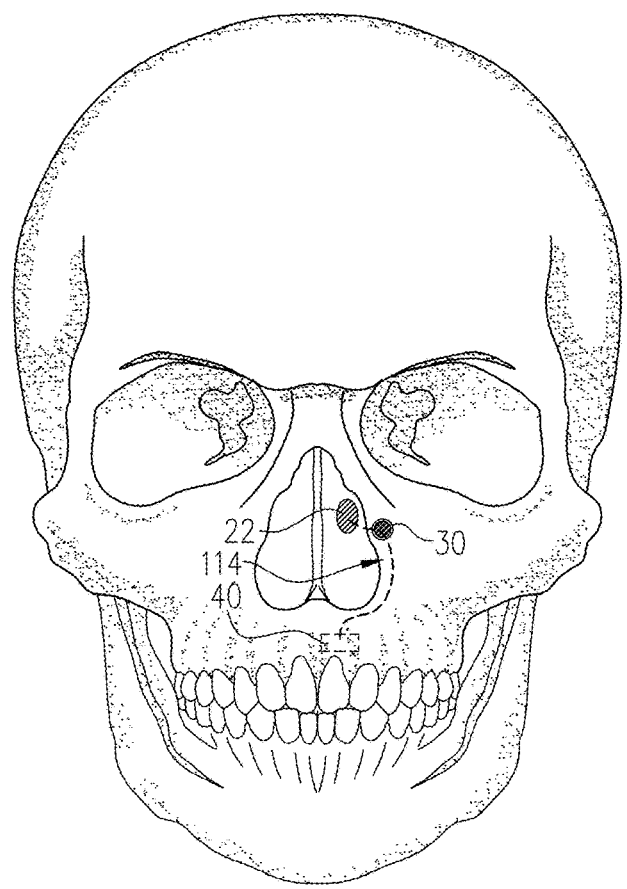
Figure 10B:
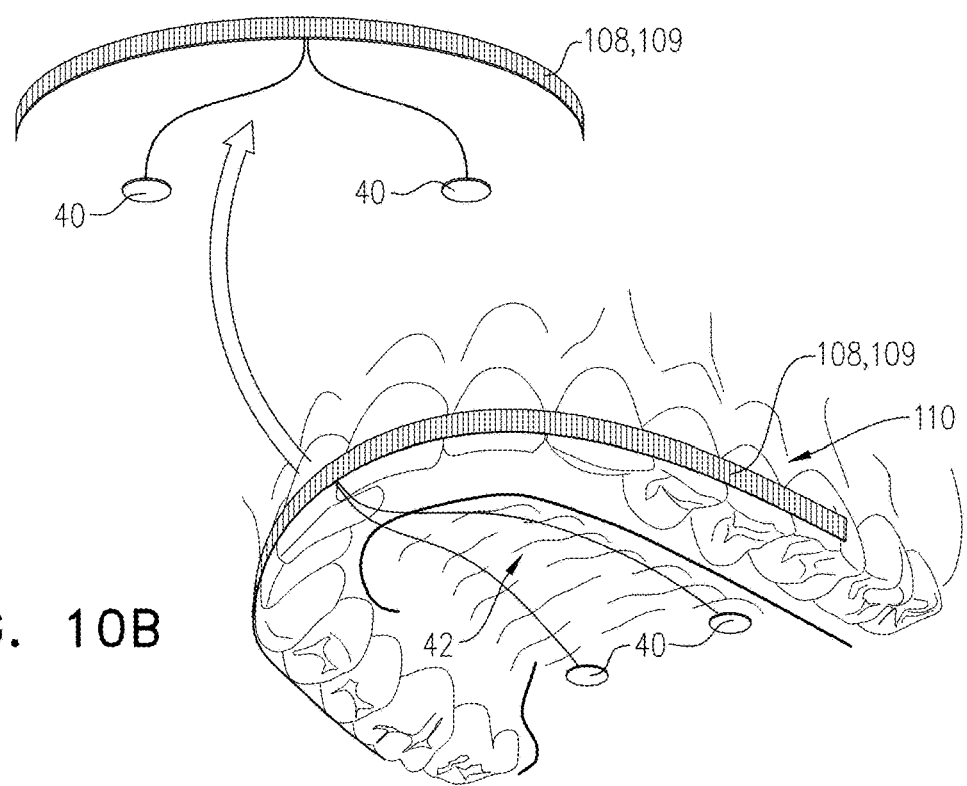

Reference is now made to FIGS. 10A-B, which show SPG stimulating device 20 in combination with at least one greater palatine foramen (GPF) electrode 40 coupled to a GPF electrode frame 108, e.g., a dental arch electrode frame 109 configured to be mounted to a dental arch 110 of patient 24, in accordance with some applications of the present invention. GPF electrode(s) 40 are coupled to control unit 26 and are couplable, using GPF electrode frame 108 (e.g., dental arch electrode frame 109) to hard palate 42 of patient 24 over a GPF 112 of patient 24. Control unit 26 drives electrode(s) 30 to stimulate SPG 22 by driving a current between electrode(s) 30 and at least one GPF electrode 40 (as illustrated by dashed current path 114).

Figure 11A:
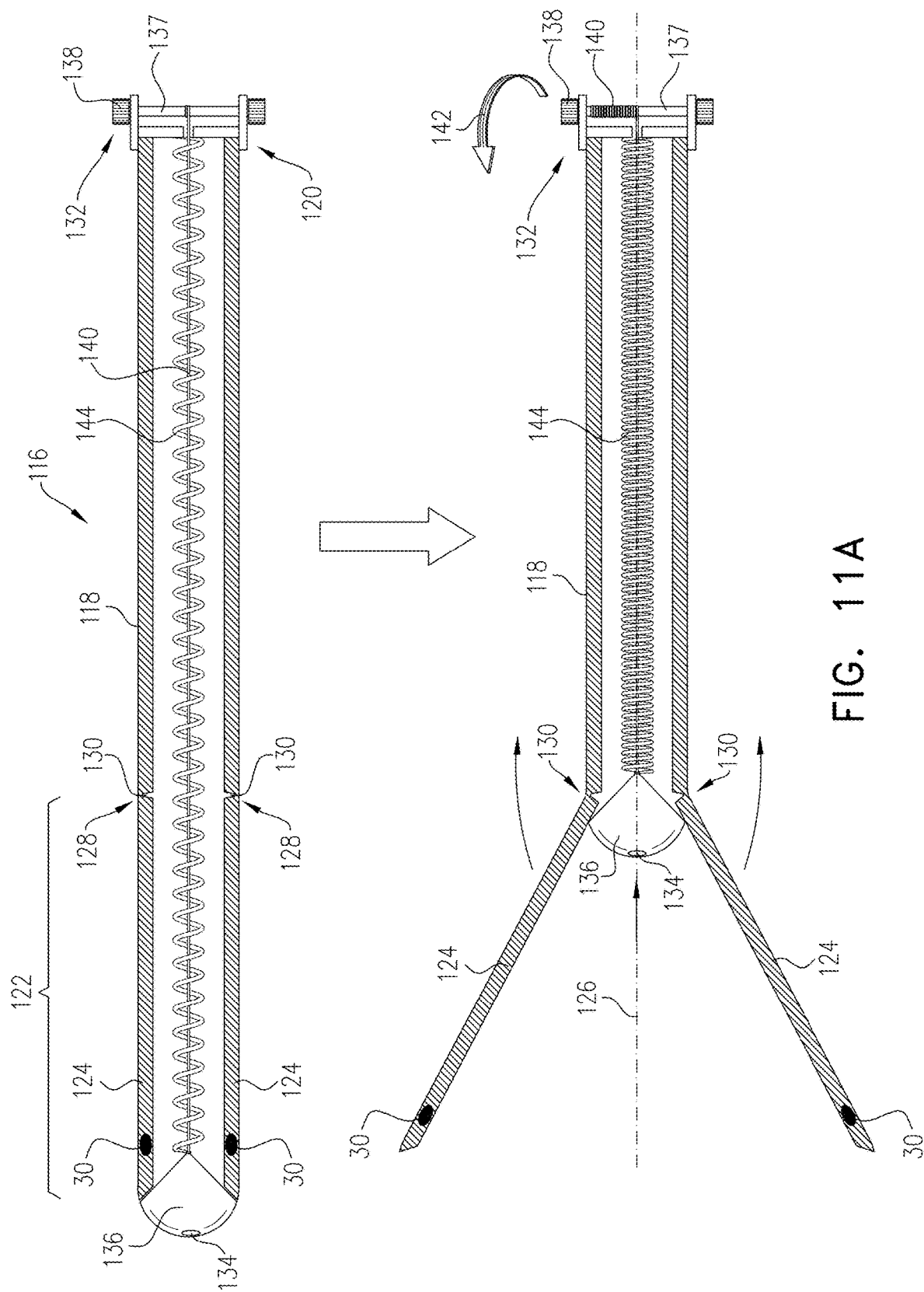
FIGS. 11A-B are schematic illustrations of a nasal SPG stimulating device, in accordance with some applications of the present invention.
Figure 11B:
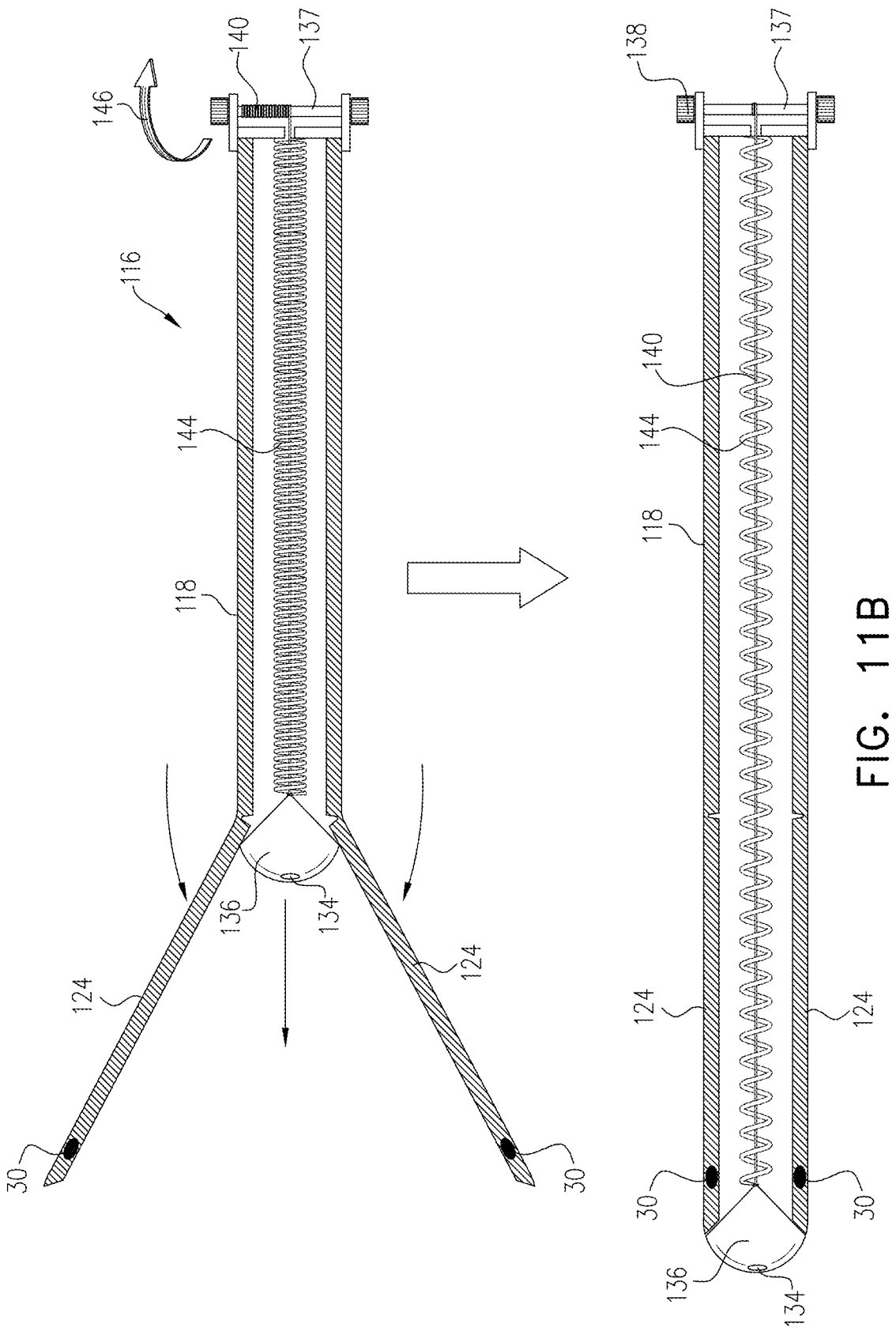

Reference is now made to FIGS. 11A-B, which are schematic illustrations of a nasal SPG stimulating device 116, in accordance with some applications of the present invention. SPG stimulating device 116 has a flexible housing 118, e.g., made from a flexible polymer, having a proximal end portion 120 and a distal end portion 122. Distal end portion 122 is configured to be placed within nose 28 of patient 24 and is shaped to define a plurality of electrode arms 124, e.g., exactly three electrode arms 124, configured to open outward away from a central longitudinal axis 126 of housing 118 during deployment of electrode arms 124. Each electrode arm 124 is coupled to flexible housing 118 at a proximal end 128 of electrode arm 124. For some applications, each electrode arm 124 is coupled to flexible housing 118 using a hinge 130, e.g., an integral hinge (such as is shown in FIGS. 11A-B), or a pivot hinge. For some applications, each electrode arm 124 is a flexible part of housing 118 that is configured to flex outwardly away from central longitudinal axis 126 during deployment of electrode arms 124.

A deployment actuator 132 is configured to actuate the deployment of electrode arms 124, further described hereinbelow. A camera 134, typically housed in a cone-shaped camera housing 136, is (a) disposed at distal end portion 122 of housing 118 prior to the deployment of electrode arms 124 and (b) configured to facilitate navigation of housing 118 toward SPG 22. As further described hereinbelow, proximal motion of camera 134 toward proximal end portion 120 of housing 118 is associated with, e.g., causes, the deployment of electrode arms 124. Coupled to each electrode arm 124 is at least one electrode 30 such that when distal end portion 122 is placed within nose 28 and electrode arm 124 is deployed, at least one electrode 30 is positioned to stimulate SPG 22. It is noted that the same reference number is used for the electrodes coupled to SPG stimulating device 116 as for electrodes coupled to SPG stimulating device 20 to indicate that the same type of electrodes may be used.

For some applications, deployment actuator 132 is a rotatable spool 137 disposed at a longitudinal location along housing 118, e.g., at proximal end portion 120 of housing 118, configured to be rotated using a knob 138. Camera housing 136 is attached to a string 140 that runs longitudinally through housing 118 and is configured to be wrapped around spool 137 when knob 138 is turned in a first direction, indicated by arrow 142. A spring 144 is disposed within housing 118 between camera housing 136 and proximal end portion 120 of housing such that proximal motion of camera housing 136 causes spring 144 to compress. SPG stimulating device 116 is positioned within nose 28 of patient 24 and then the medical practitioner rotates knob 138 so as to wind string 140 around spool 137, illustrated by arrow 142. As string 140 is wound around spool 137, camera housing 136 is pulled proximally, thereby causing spring 144 to compress. Due to the conical shape of camera housing 136, as camera housing 136 moves proximally, camera housing 136 forces electrode arms 124 to deploy outward.

FIG. 11B illustrates how electrode arms 124 of SPG stimulating device 116 are closed prior to removal of SPG stimulating device 116 from nose 28 of patient 24. In order to close electrode arms 124, the medical practitioner turns knob 138 in the opposite direction, illustrated by arrow 146, thus unwinding string 140 from spool 137. Due to the compressed state of spring 144, as string 140 is unwound from around spool 137, spring 144 pushes camera housing 136 distally thus allowing electrode arms 124 to close back to their initial starting position.

Figure 12A:
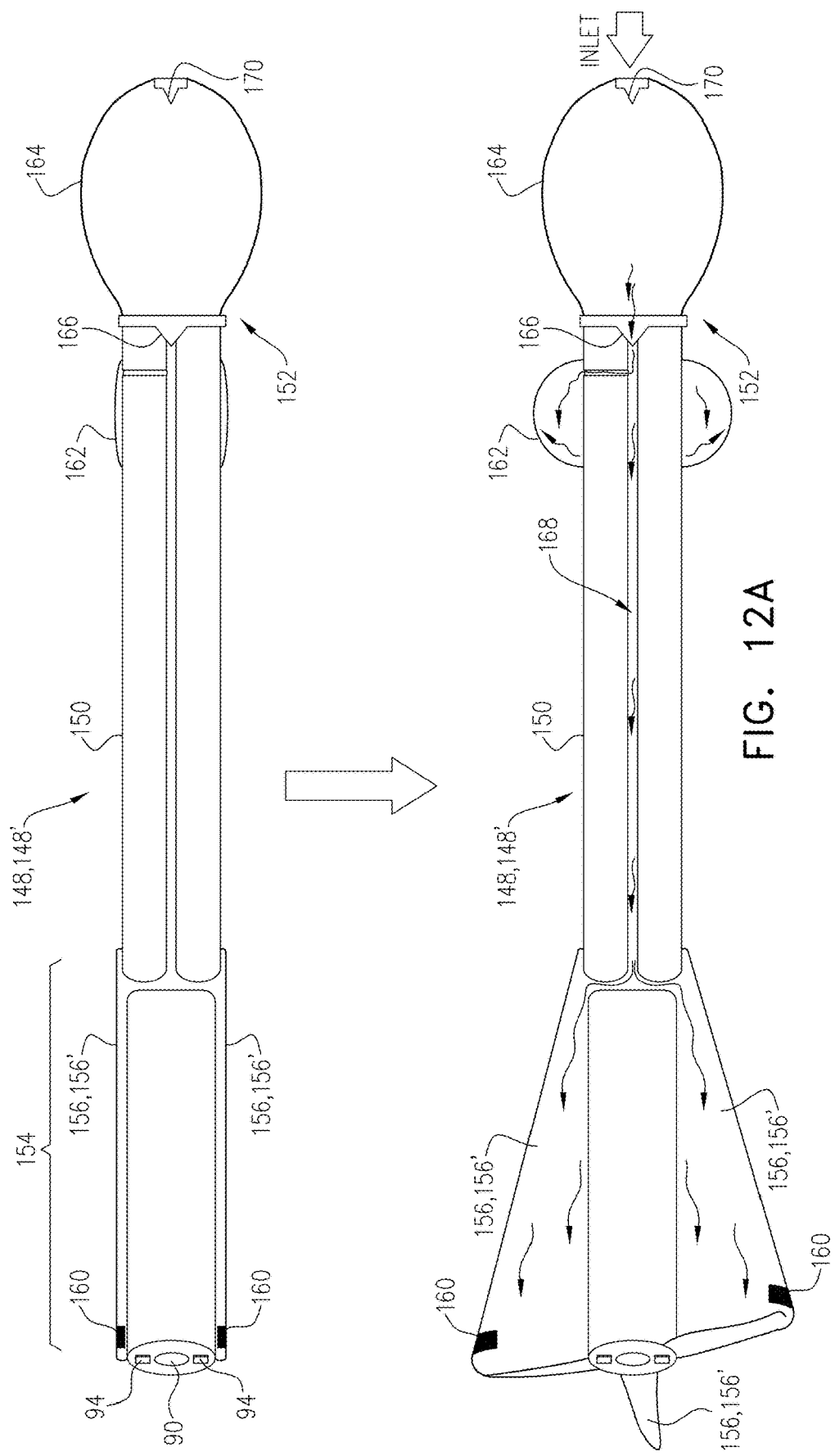
Figure 12B:
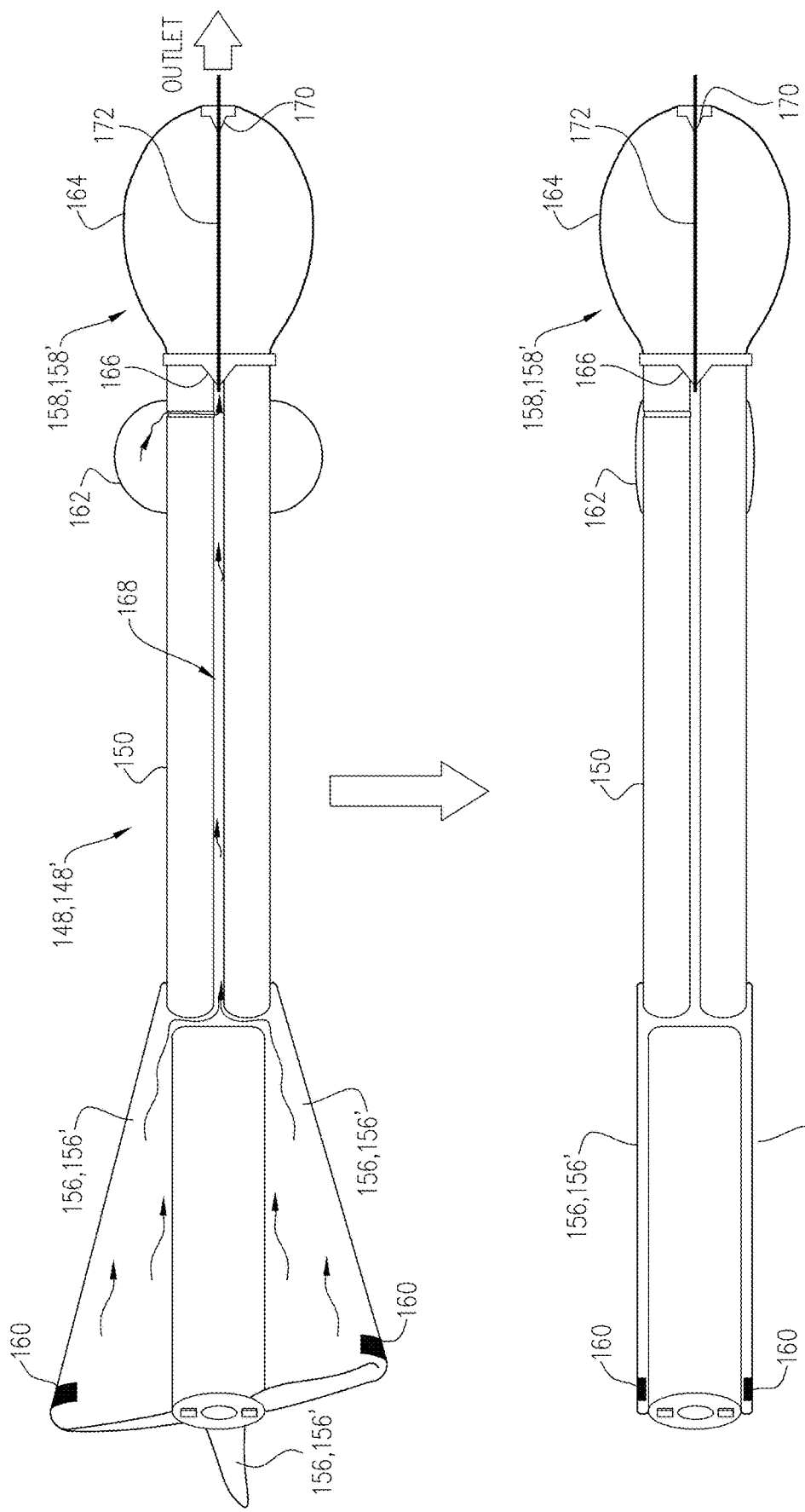

Reference is now made to FIGS. 12A-B and 13, which are schematic illustrations of a nasal SPG stimulating device 148, in accordance with some applications of the present invention. Nasal SPG stimulating device 148 includes a flexible tube 150 configured for placement within nose 28 of patient 24 and having a proximal end portion 152 and a distal end portion 154. Distal end portion 154 has at least one inflatable electrode mount 156, and proximal end portion 152 includes an inflation actuator 158 via which at least one inflatable electrode mount 156 is inflatable. At least one electrode 160, e.g., a plurality of electrodes 160, is coupled to inflatable electrode mount 156 (typically, to an external surface of inflatable electrode mount 156) such that when SPG stimulating device 148 is placed within nose 28 and inflatable electrode mount 156 is inflated, electrode 160 is positioned to stimulate SPG 22. For some applications, each electrode 160 comprises a specific area of inflatable electrode mount 156 made of a conductive polymer. Typically, SPG stimulating device 148 further includes an inflatable nasal stabilizer 162 disposed around flexible tube 150 and configured to stabilize flexible tube 150 with respect to nostril 60 of nose 28 when flexible tube 150 is disposed within nose 28 and inflatable nasal stabilizer 162 is inflated using inflation actuator 158. Similarly to SPG stimulating device 20, SPG stimulating device 148 also includes camera 90, e.g., a micro camera, or a fiber-optic camera, to facilitate navigation of the device toward SPG 22, and one or more light sources 94, e.g., LED light sources, in order to provide illumination for camera 90.

Reference is now made specifically to FIGS. 12A-B, which depict a particular variation SPG stimulating device 148', which is an implementation of SPG stimulating device 148, in accordance with some applications of the present invention. For some applications, SPG stimulating device 148' includes a plurality of inflatable electrode mounts 156', e.g., exactly three inflatable electrode mounts 156', positioned circumferentially around distal end portion 154 of flexible tube 150. A respective at least one electrode 160 is coupled to each of the respective inflatable electrode mounts 156'.

Inflation actuator 158' of SPG stimulating device 148' is in the form of a hand bulb pump. A hollow pumpable bulb 164 is disposed proximal end portion 152 of flexible tube 150. A first duckbill valve 166 allows air from within bulb 164 to enter an air-channel 168 that extends through flexible tube 150 when bulb 164 is squeezed. Air-channel 168 includes ports that allow air from within air-channel 168 to enter each inflatable electrode mount 156' and inflatable nasal stabilizer 162. As the squeezing of bulb 164 is released, a second duckbill valve 170 allows air from outside the device to enter bulb 164 in order to re-inflate bulb 164. Bulb 164 may thus be pumped one or more times in order to inflate inflatable electrode mounts 156' and inflatable nasal stabilizer 162. FIG. 12A shows the transition from (a) SPG stimulating device 148' prior to inflation (i.e., the form in which SPG stimulating device 148' is inserted into nose 28 of patient 24) to (b) SPG stimulating device 148' after inflation of inflatable electrode mounts 156' and inflatable nasal stabilizer 162. FIG. 12B illustrates the deflation of inflatable electrode mounts 156' and inflatable nasal stabilizer 162 prior to removal of SPG stimulating device 148' from nose 28. A narrow hollow rod 172, e.g., a needle, is inserted through the opening of both duckbill valve 177 and duckbill valve 166 in order to provide fluid communication between air-channel 168 and the environment, thus allowing inflatable electrode mounts 156' and inflatable nasal stabilizer 162 to deflate.

Reference is now made specifically to FIG. 13, which depicts SPG stimulating device 148''', which is an implementation of SPG stimulating device 148, in accordance with some applications of the present invention. For some applications, the at least one inflatable electrode mount 156 is an inflatable electrode balloon 156'' with a plurality of electrodes 160 positioned circumferentially around inflatable balloon 156'' such that when SPG stimulating device 148'' is placed within nose 28 of patient 24 and inflatable electrode balloon 156'' is inflated, at least one of the plurality of electrodes 160 is positioned to stimulate SPG 22. Typically, inflatable electrode balloon 156'' is circular or elliptical in cross-section perpendicular to an axis of flexible tube 150.

Inflation actuator 158'' of SPG stimulating device 148'' may be a Luer lock valve to which a Luer syringe 174 may be coupled. When Luer syringe 174 is coupled to the Luer lock valve, the valve is opened and gas or liquid may be injected into flexible tube 150 in order to inflate inflatable electrode balloon 156'' and inflatable nasal stabilizer 162. When Luer syringe 174 is disconnected from the Luer lock valve, the valve self-seals. In order to deflate inflatable electrode balloon 156'' and inflatable nasal stabilizer 162, Luer syringe 174 is re-coupled to the Luer lock valve and the injected gas or liquid escapes or is drawn out. For some applications, inflatable electrode balloon 156'' and inflatable nasal stabilizer 162 may be inflated with an injection of contrast fluid. This may aid visualization of the positioning of SPG stimulating device 148'' within nose 28 under fluoroscopy.

Reference is now made to FIGS. 14A-C, which are schematic illustrations of SPG stimulating device 148'', which is an implementation of SPG stimulating device 148, in accordance with some applications of the present invention. SPG stimulating device 148' is an implantable unit connected (via a quick-connector 176 further described hereinbelow) to a flexible catheter 178, e.g., a steerable catheter. For some applications, a diameter D4 of flexible catheter may be at least 3 mm and/or less than 8 mm. For some applications, a length L of the implantable unit may be at least 40 mm and/or less than 80 mm. An actuation handle 180 is disposed at a proximal end of flexible catheter 178. Similarly to SPG stimulating device 148'', SPG stimulating device 148''' has inflatable electrode balloon 156''' and inflatable nasal stabilizer 162. Typically, inflatable electrode balloon 156'' is circular or elliptical in cross-section perpendicular to an axis of flexible tube 150. A plurality of channels extend from a proximal end 187 of actuation handle 180 through flexible catheter 178 to SPG stimulating device 148'. The channels may include, for example, any combination of one or more of the following:

an irrigation channel 182 (e.g., that ends at a distal tip 186 of SPG stimulating device 148''), the actuation of irrigation through irrigation channel 182 controlled by irrigation control 183 on actuator handle 180, and a proximal end 187 of actuator handle 180 including an irrigation connector 191 to connect handle 180 to a source of irrigation liquid;

a suction channel 188 (e.g., that ends at distal tip 186), the actuation of suction through suction channel 188 controlled by suction control 189 on actuator handle 180, and proximal end 187 of actuator handle 180 including a suction port 190 for connecting handle 180 to a source of vacuum;

an endoscope channel 192 that starts from proximal end 187 of handle and extends through to distal tip 186, through which an endoscope can be inserted to aid in navigation of SPG stimulating device 148''' toward SPG 22 of patient 24, actuator handle 180 including an endoscope control 206;

an electrode balloon inflation channel 194 that extends to inflatable electrode balloon 156'' and includes an electrode balloon two-way port 195 that enables fluid communication between electrode balloon inflation channel 194 and inflatable electrode balloon 156'' for inflation and deflation of inflatable electrode balloon 156'' (illustrated by cross-section A-A in FIG. 14B), the inflation and deflation of inflatable electrode balloon 156''' controlled by electrode balloon control 197 on actuator handle 180, and proximal end 187 of actuator handle 180 including an air-port 199 connecting handle 180 to a source of air for inflation; and a nasal stabilizer inflation channel 196 that extends to inflatable nasal stabilizer 162 and includes a nasal stabilizer two-way port 198 that enables fluid communication between nasal stabilizer inflation channel 196 and inflatable nasal stabilizer 162 for inflation and deflation of inflatable nasal stabilizer 162 (illustrated by cross-section B-B in FIG. 14B), the inflation and deflation of inflatable nasal stabilizer 162 controlled by nasal stabilizer control 204 on actuator handle 180, and proximal end 187 of actuator handle 180 including air-port 199 connecting handle 180 to a source of air for inflation.

An electrode-lead channel 200 for electrode leads 98 extends from inflatable electrode balloon 156'' to a lead-exit hole 202 on a lateral side of SPG stimulating device 148'. FIG. 14C illustrates connector 176 between SPG stimulating device 148'' and flexible catheter 178. For some applications, connector 176 is a face-seal connector, i.e., it connects two components face-to-face with no overlap between the components. A pneumatic seal is activated between SPG stimulating device 148' and flexible catheter 178 via a plurality of suction micro-channels 208 at connector 176. An alignment facilitator 210 allows the medical practitioner to align SPG stimulating device 148' and flexible catheter 178 correctly with respect to each other so that the respective channels line up correctly, and subsequently suction is applied through micro-channels 208 in order to seal the connection between SPG stimulating device 148' and flexible catheter 178. Once SPG stimulating device 148'' has been positioned correctly within nose 28 (and the endoscope removed in cases where an endoscope is fed through endoscope channel 192), the suction through micro-channels 208 may be terminated in order to disconnect flexible catheter 178 from SPG stimulating device 148". Suction through micro-channels 208 is controlled by connector control 209 on actuator handle 180. It is noted that the pneumatic face-seal connector described herein is just one example of a connector between SPG stimulating device 148' and flexible catheter 178, and is not intended to be limiting. Any type of connector that maintains connection between SPG stimulating device 148' and flexible catheter 178 during positioning of SPG stimulating device 148' and can then subsequently be disconnected may be used.

Figure 15:
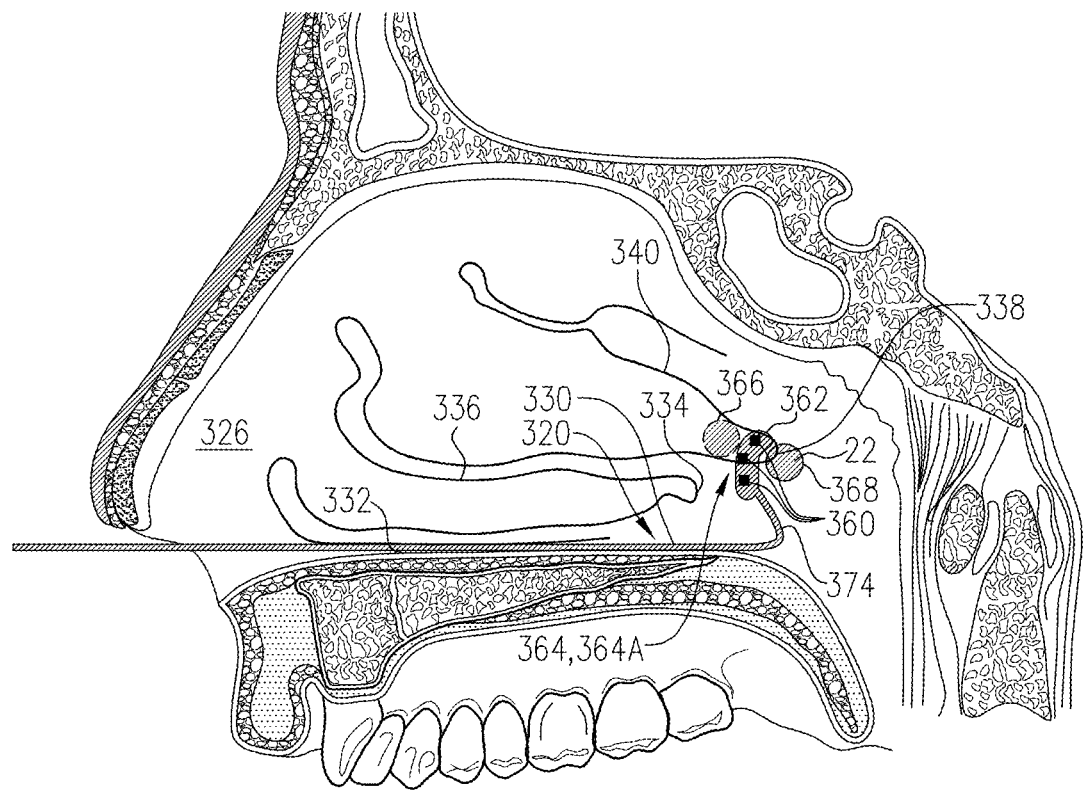
FIG. 15 is a schematic illustration of an SPG stimulating device for stimulating an SPG of a patient from within a nasal cavity, in accordance with some applications of the present invention.

Reference is now made to FIG. 15, which is a schematic illustration of an SPG stimulating device 320 for stimulating SPG 22 of patient 24 from within a nasal cavity 326, in accordance with some applications of the present invention. FIG. 15 provides a highly schematic illustration of SPG stimulating device 320, while other figures described herein provide more detailed views of several configurations of the device. FIG. 15 shows a medial cross-sectional view of the anatomy.

In some applications of the present invention, SPG stimulating device 320 comprises:
- a tube 330, which is dimensioned to be insertable along a floor 332 of nasal cavity 326 to near a posterior end 334 of an inferior turbinate 336; typically, tube 330 is flexible (and, optionally steerable, as described hereinbelow); and
- an electrode mount 362, which comprises one or more electrodes 360.

Typically, SPG stimulating device 320 is configured to deploy the one or more electrodes 360 superiorly away from tube 330 while tube 330 is disposed along floor 332 of nasal cavity 326, so as to position the one or more electrodes 360 against a wall 364 of nasal cavity 326 for stimulating SPG 22. The word "superiorly" is used in the anatomical sense of in a superior, i.e., upward, direction with respect to the body.

For some applications, wall 364 is a lateral wall 364A of nasal cavity 326, and SPG stimulating device 320 is configured to deploy the one or more electrodes 360 superiorly and laterally away from tube 330, so as to position the one or more electrodes 360 against lateral wall 364A of nasal cavity 326 for stimulating SPG 22.

For some applications, SPG stimulating device 320 is configured to deploy the one or more electrodes 360 superiorly and laterally away from tube 330 to an area of a middle meatus 366, near posterior end 334 of inferior turbinate 336 and a posterior end 338 of a middle turbinate 340 and an area of a sphenopalatine foramen 368, while tube 330 is disposed along floor 332 of nasal cavity 326, so as to position the one or more electrodes 360 against wall 364 of nasal cavity 326 for stimulating SPG 22. As mentioned above, for some applications, wall 364 is lateral wall 364A of nasal cavity 326; for some of these applications, SPG stimulating device 320 is configured to deploy the one or more electrodes 360 superiorly and laterally away from tube 330 to the area of middle meatus 366 and sphenopalatine foramen 368, so as to position the one or more electrodes 360 against lateral wall 364A of nasal cavity 326 for stimulating SPG 22.

For some applications, electrode mount 362 is configured to secure the one or more electrodes 360 in place after deployment. For example, electrode mount 362 may contact sufficient points within nasal cavity 326 to prevent unwanted motion of the one or more electrodes 360.

Alternatively or additionally, for some applications, the one or more electrodes are coated with an adhesive material.

Figure 16A:
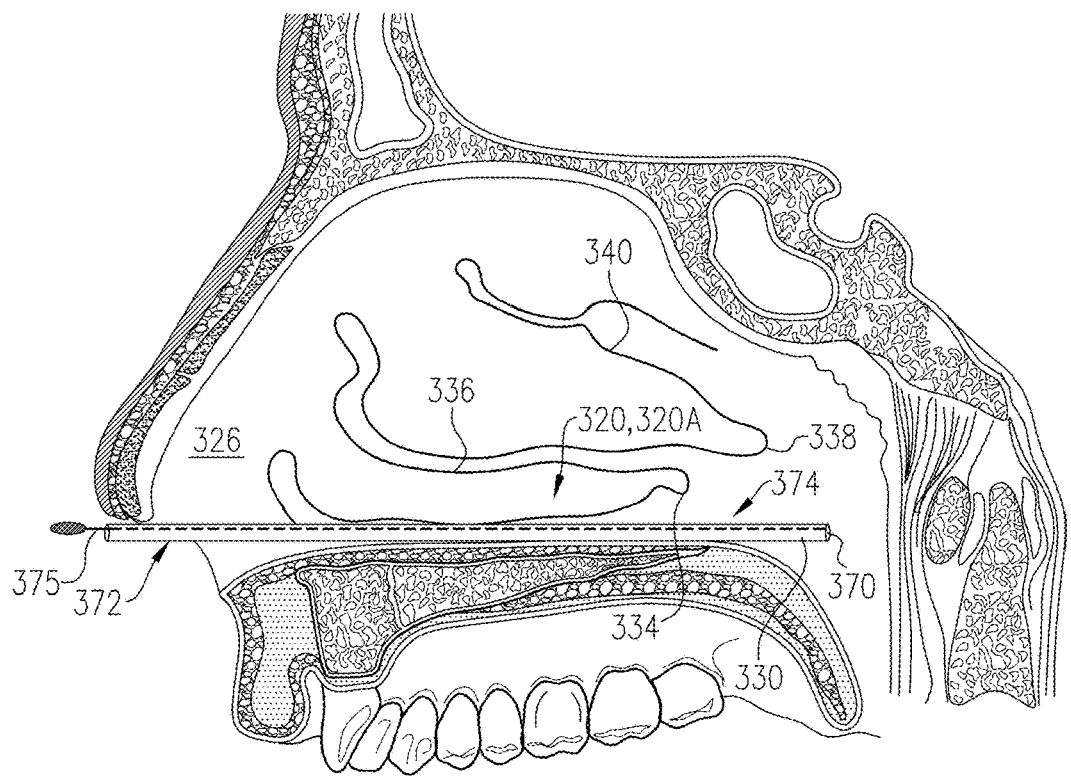
FIGS. 16A-C are schematic illustrations of an SPG stimulating device and a method for stimulating the SPG from within the nasal cavity using the SPG stimulating device, in accordance with respective applications of the present invention.
Figure 16B:
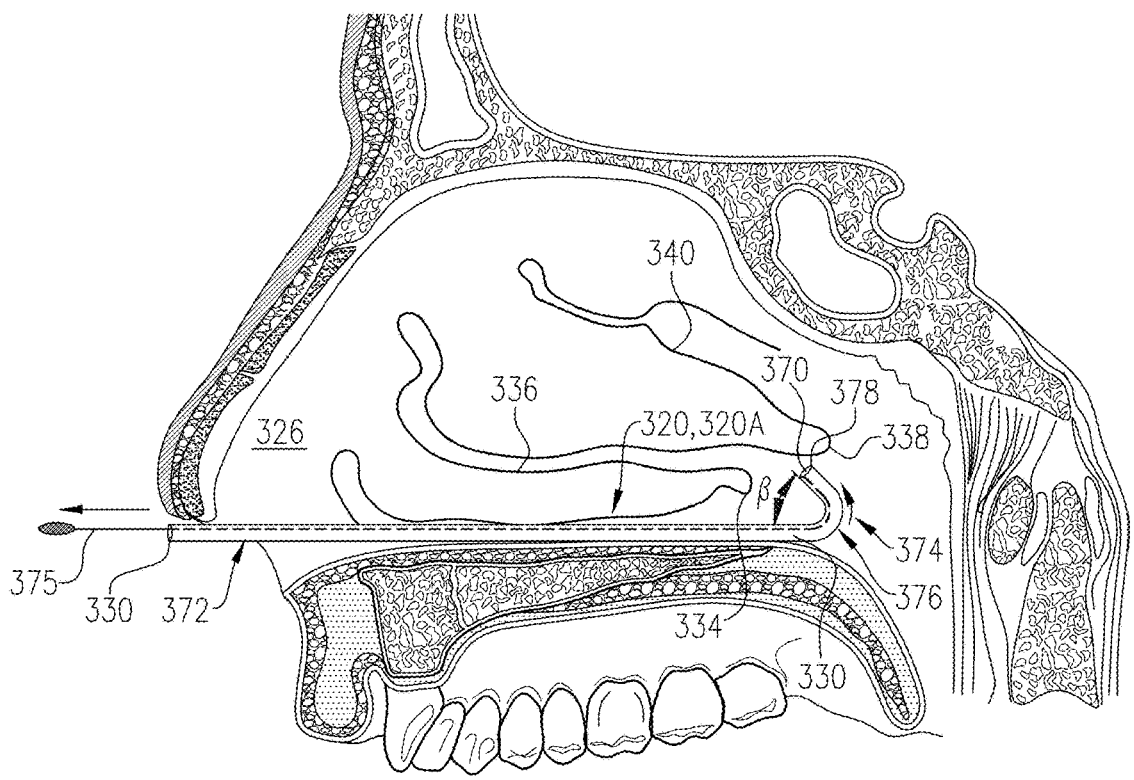
Figure 16C:
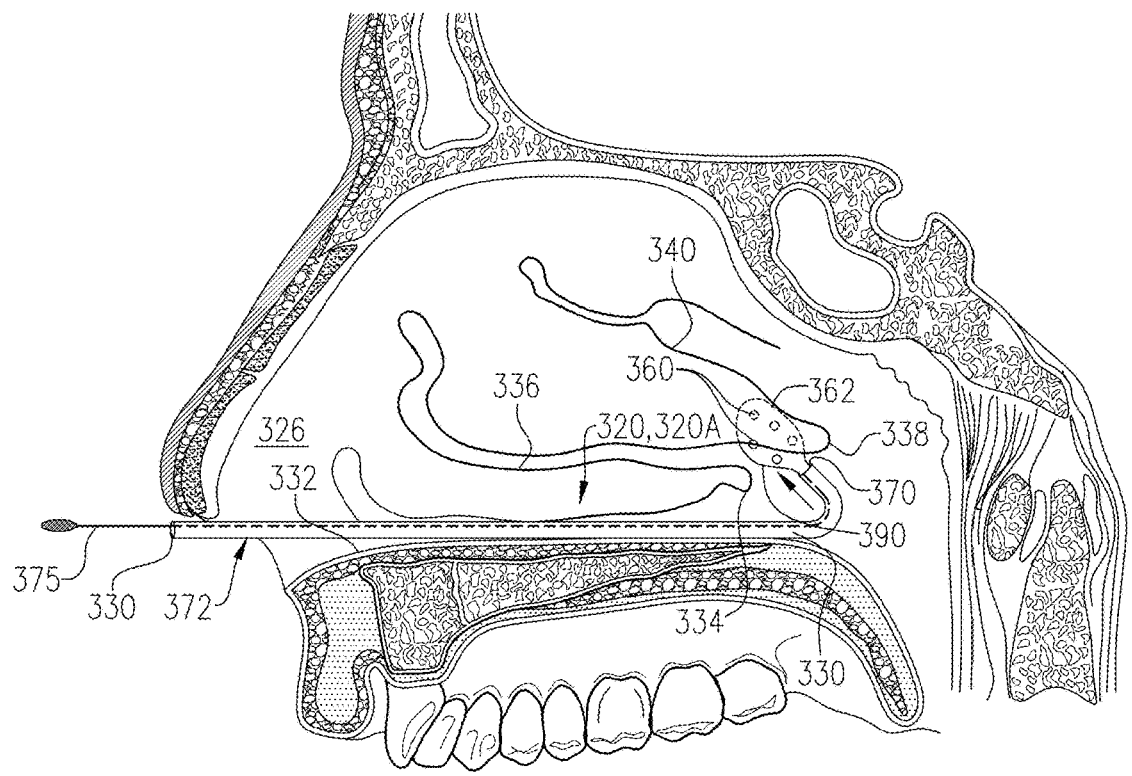

Reference is now made to FIGS. 16A-C, which are schematic illustrations of an SPG stimulating device 320A and a method for stimulating SPG 22 of patient 24 from within nasal cavity 326 using SPG stimulating device 320A, in accordance with respective applications of the present invention. FIG. 16A-C show medial cross-sectional views of the anatomy.

Reference is further made FIGS. 17A-D, which are schematic illustrations of SPG stimulating device 320A and the method of using the device, in accordance with respective applications of the present invention. FIGS. 17A-D show posterior cross-sectional views of the anatomy. A nasal septum 322 is labeled in FIG. 17A.

SPG stimulating device 320A is one implementation of SPG stimulating device 320 described hereinabove with reference to FIG. 15, and may implement any of the techniques described hereinabove with reference to FIG. 15, mutatis *mutandis*.

Figure 17A:
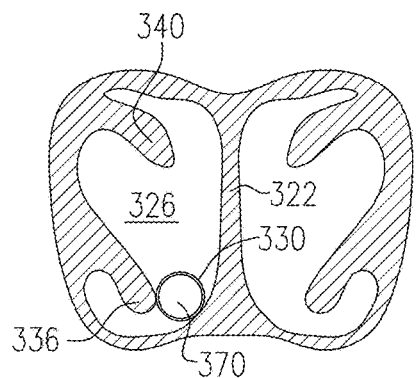
FIGS. 17A-D are schematic illustrations of the SPG stimulating device of FIGS. 16A-C and the method of using the device, in accordance with respective applications of the present invention.
Figure 17B:
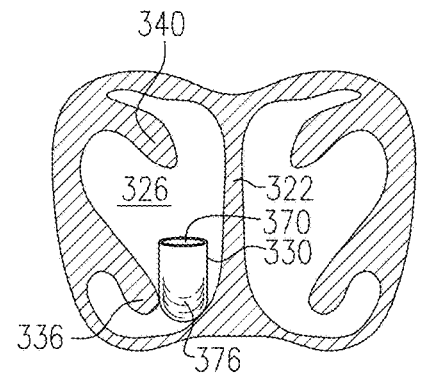
Figure 17C:
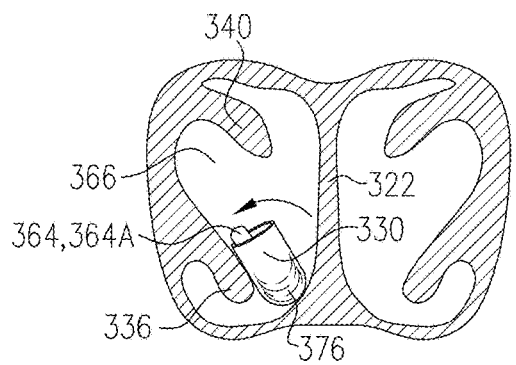
Figure 17D:
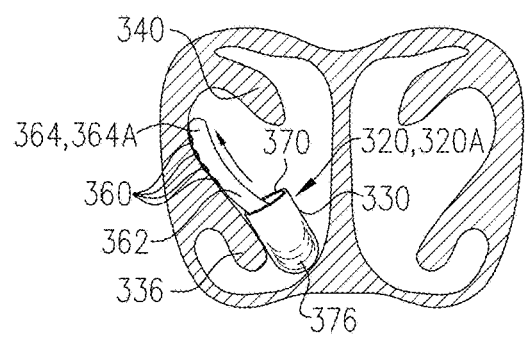

For some applications, tube 330 is shaped so as to define a distal end opening 370, and the one or more electrodes 360 are deployable from tube 330 via distal end opening 370, such as shown in FIGS. 16C and 17C-D. In these applications, the one or more electrodes 360 are typically deployed by deploying electrode mount 362 from tube 330 via distal end opening 370, such as shown.

For some applications, tube 330 is steerable, and comprises a deflecting mechanism 372 configured to bend a distal end portion 374 of tube 330 in at least one direction (e.g., exactly one direction) with respect to an axis of tube 330, in order to facilitate superior deployment of the one or more electrodes 360 away from tube 330. For example, deflecting mechanism 372 may comprise one or more steering wires 375, such as exactly one steering wire 375, and, optionally, one or more anchor rings; application of tension to one or more of the one or more steering wires deflects distal end portion 374 of tube 330.

For some applications, deflecting mechanism 372 is configured to bend distal end portion 374 of tube 330 in at least one direction (e.g., exactly one direction) by an angle β (beta) of 45-150 degrees with respect to an axis of tube 330, as labeled in FIG. 16B. (Deflecting mechanism 372 may be configured to retro-bend distal end portion 374 of tube 330 such that angle β (beta) is less than 90 degrees, such as shown in FIG. 16B, 90 degrees, or greater than 90 degrees, such as shown for steerable elongate guide member 418 in FIG. 39A).

For some applications, such as shown in FIGS. 16A-C and 17A-D, tube 330 is unidirectionally steerable. Optionally, SPG stimulating device 320 comprises a user control handle that comprises exactly one button configured to cause the unidirectional steering.

For some applications, such as labeled in FIGS. 16B and 17B-D, tube 330 is deflectable at a deflection region 376 of tube 330 that is:
- 0.5-2.5 cm from a distal end 378 of tube 330; typically, the portion of tube 330 proximal to deflection region 376 is fairly rigid;
- less than 6 cm from a proximal end of tube 330; and/or
- 4-6 cm from a location on tube 330 disposed at a nostril.

For some applications:
- an outer diameter of tube 330 is 2-6 mm,
- a length of tube 330 is 5-8.5 cm, and/or
- a length of a portion of tube 330 that is configured to be placed within nasal cavity 326 is no more than 8 cm, such as no more than 6 cm.

In the configuration shown in FIG. 16C, electrode mount 362 is shaped as a paddle 390.

As described hereinabove with reference to FIG. 15, for some applications SPG stimulating device 320 is configured to deploy the one or more electrodes 360 superiorly and laterally away from tube 330 to an area of a middle meatus 366. For some of these applications, the superior deployment is performed by deflecting distal end portion 374, such as shown in FIGS. 16B and 17B, and the lateral deployment is performed by rotating tube 330, such as shown in FIG. 17C.

Figure 18A:
FIGS. 18A-C are schematic illustrations of another SPG stimulating device and a method for stimulating the SPG from within the nasal cavity using the SPG stimulating device, in accordance with respective applications of the present invention.
Figure 18B:
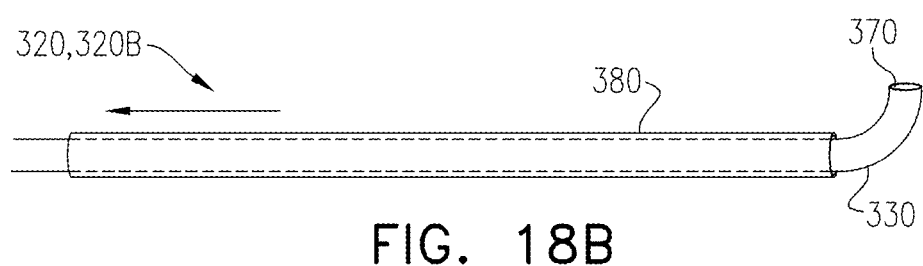
Figure 18C:
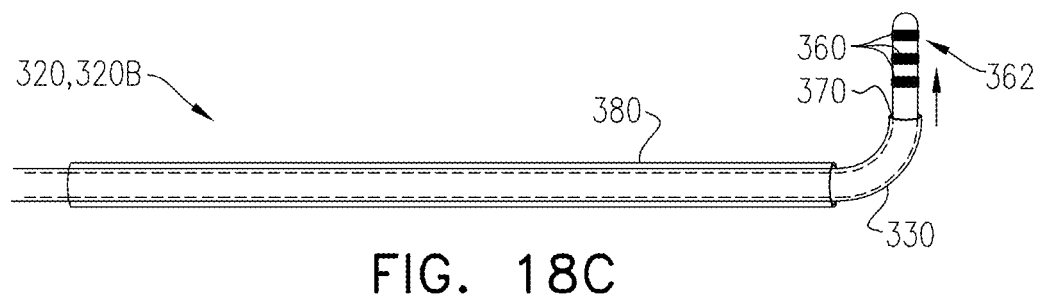

Reference is now made to FIGS. 18A-C, which are schematic illustrations of an SPG stimulating device 320B for stimulating SPG 22 of patient 24 from within nasal cavity 326, in accordance with an application of the present invention. SPG stimulating device 320B is one implementation of SPG stimulating device 320 described hereinabove with reference to FIG. 15, and may implement any of the techniques described hereinabove with reference to FIG. 15, 16A-C, and/or 17A-D, mutatis *mutandis*.

For some applications, distal end portion 374 of tube 330 is configured to be curved when in an unconstrained resting state, such as shown in FIGS. 18B-C, in order to facilitate superior deployment of the one or more electrodes 360 away from tube 330 from distal end opening 370, such as shown in FIG. 18C.

For some applications, SPG stimulating device 320 further comprises a deployment sheath 380, in which at least distal end portion 374 is removably disposed so as to constrain distal end portion 374 of tube 330 in a straightened state, such as shown in FIG. 18A.

Figure 19:
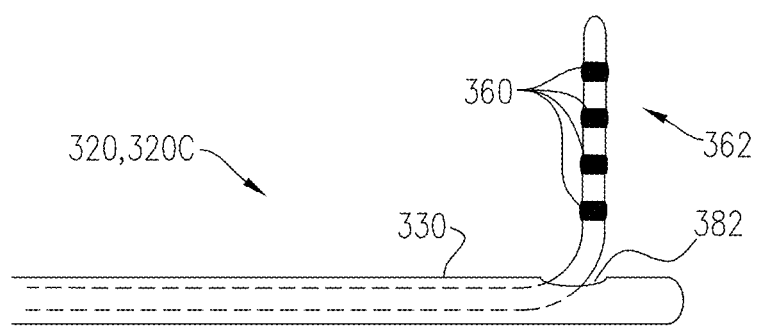
FIG. 19 is a schematic illustration of yet another SPG stimulating device and a method for stimulating the SPG from within the nasal cavity using the SPG stimulating device, in accordance with respective applications of the present invention.

Reference is now made to FIG. 19, which is schematic illustration of an SPG stimulating device 320C for stimulating SPG 22 of patient 24 from within nasal cavity 326, in accordance with an application of the present invention.

Figure 20A:
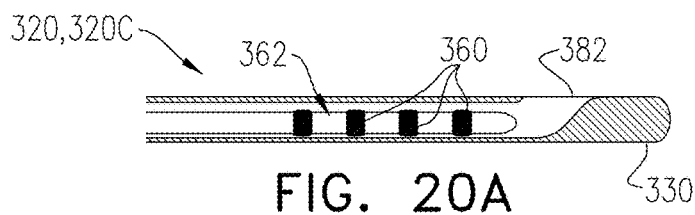
FIGS. 20A-C are schematic cross-sectional illustrations of the SPG stimulating device of FIG. 19, in accordance with an application of the present invention.
Figure 20B:
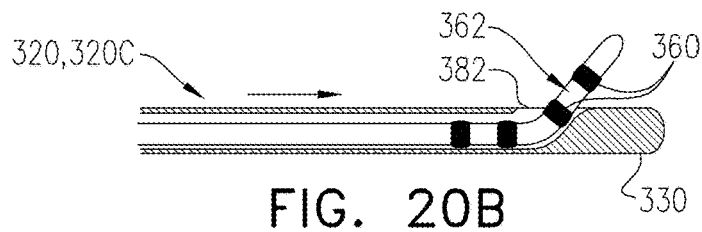
Figure 20C:
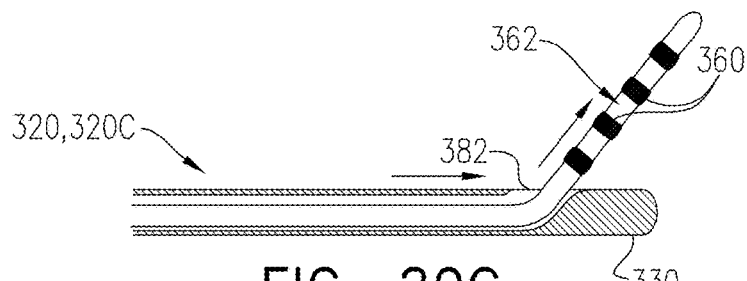

Reference is further made FIGS. 20A-C, which are schematic cross-sectional illustrations of SPG stimulating device 320C, in accordance with an application of the present invention.

SPG stimulating device 320C is one implementation of SPG stimulating device 320 described hereinabove with reference to FIG. 15, and may implement any of the techniques described hereinabove with reference to FIG. 15, 16A-C, and/or 17A-D, mutatis *mutandis*.

For some applications, tube 330 is shaped so as to define a side opening 382, and the one or more electrodes 360 are deployable from tube 330 via side opening 382. In these applications, the one or more electrodes 360 are typically deployed by deploying electrode mount 362 away from tube 330 via side opening 382, such as shown.

Optionally, such as shown in FIGS. 20A-C, a portion of a channel within tube 330 near side opening 382 may be shaped so control the angle at which the one or more electrodes 360 (and electrode mount 362, if provided) exit side opening 382.

Figure 21A:
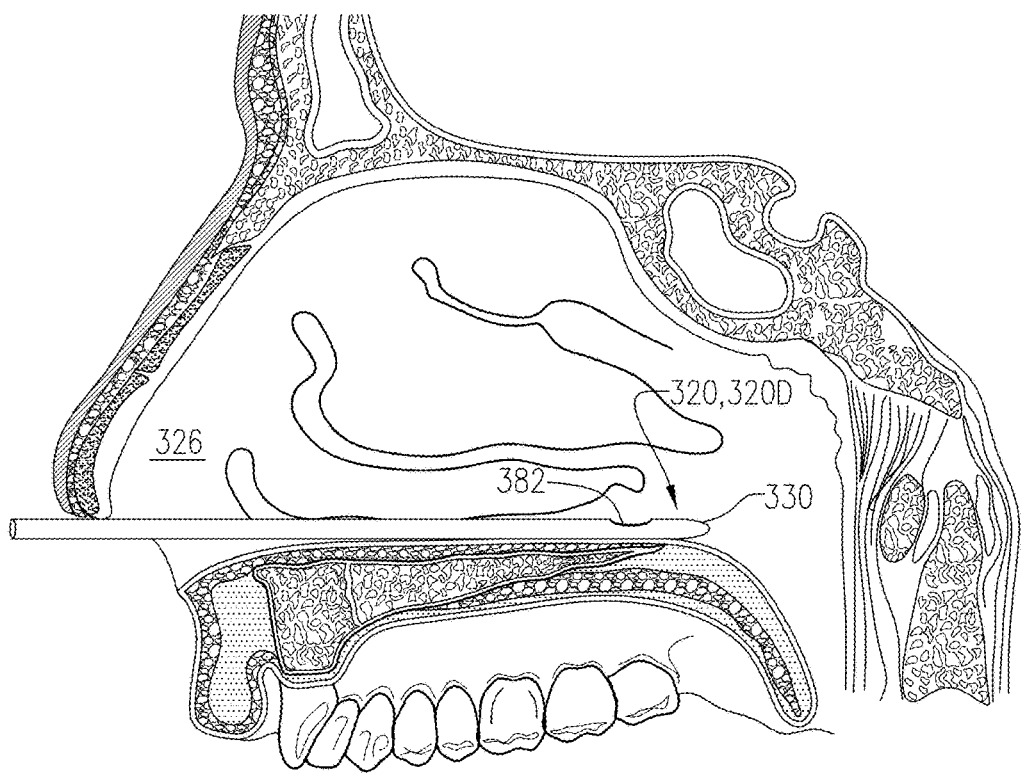
FIGS. 21A-C are schematic illustrations of still another SPG stimulating device and a method for stimulating the SPG from within the nasal cavity using the SPG stimulating device, in accordance with respective applications of the present invention.
Figure 21B:
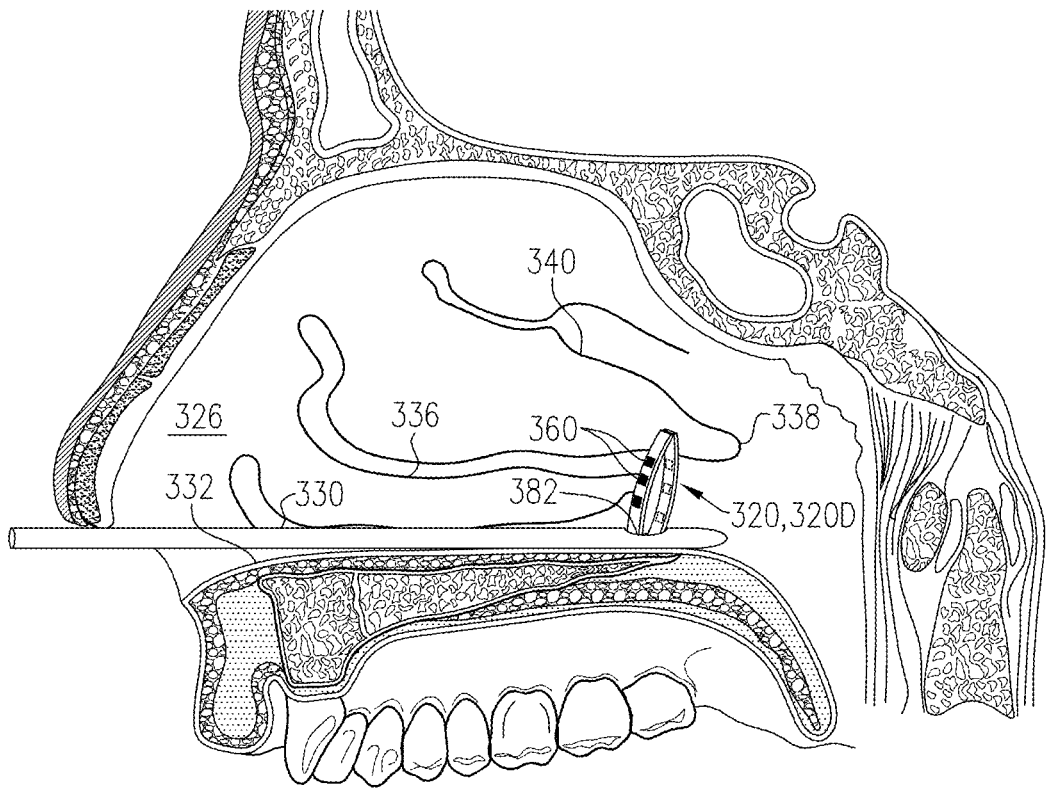
Figure 21C:
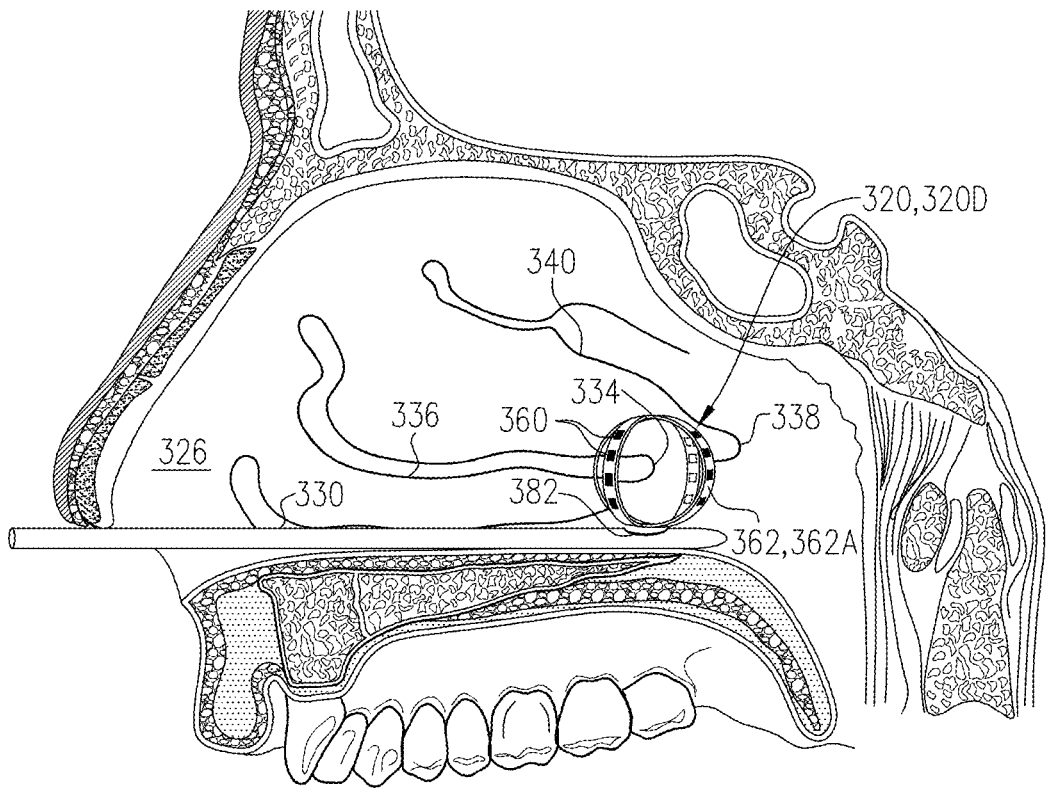

Reference is now made to FIGS. 21A-C, which are schematic illustrations of an SPG stimulating device 320D and a method for stimulating SPG 22 of patient 24 from within nasal cavity 326 using SPG stimulating device 320D, in accordance with respective applications of the present invention. SPG stimulating device 320D is one implementation of SPG stimulating device 320 described hereinabove with reference to FIG. 15, and may implement any of the techniques described hereinabove with reference to FIG. 15, 16A-C, 17A-D, 19, and/or 20A-C, mutatis *mutandis*.

As described above, for some applications, tube 330 is shaped so as to define side opening 382, and the one or more electrodes 360 are deployable away from tube 330 via side opening 382.

For some applications, electrode mount 362 comprises an electrode mount 362A, which comprises one or more rings 384 to which the one or more electrodes 360 are coupled. For some applications, electrode mount 362A is shaped as a basket. Typically, electrode mount 362A is either spring-loaded, or opens by the application of force through, for example, a pull wire. The one or more electrodes 360 may be arranged in a two-dimensional or three-dimensional configuration. Optionally, electrode mount 362A implements some or all of the techniques of electrode mount 462, described hereinbelow with reference to FIGS. 45A and 45B, mutatis *mutandis*. For example, a greatest dimension of electrode mount 362A (which may correspond to a diameter, for example) may be 0.8-3.8 mm.

Figure 22:
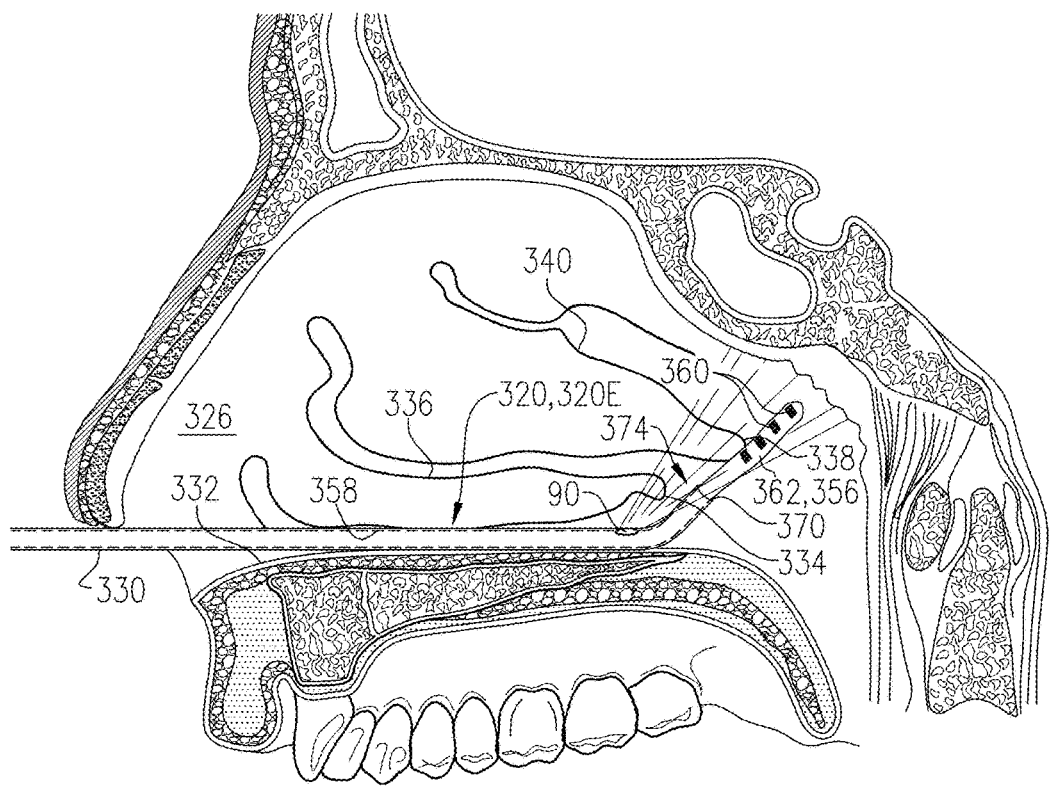
FIG. 22 is a schematic illustration of yet another SPG stimulating device and a method for stimulating the SPG from within the nasal cavity using the SPG stimulating device, in accordance with an application of the present invention.
Figure 23A:
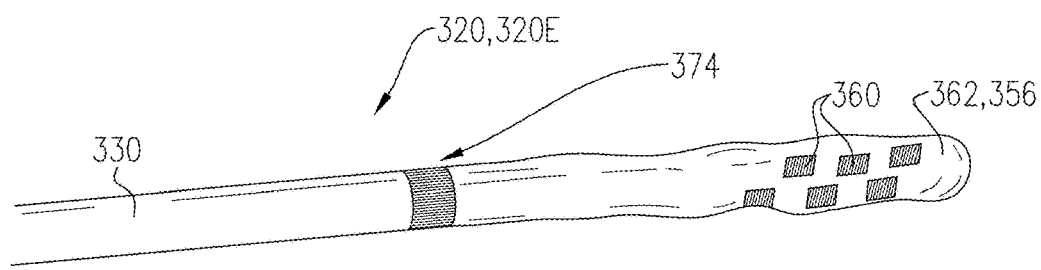
FIGS. 23A-B are schematic illustrations of the SPG stimulating device of FIG. 22, in accordance with an application of the present invention.
Figure 23B:
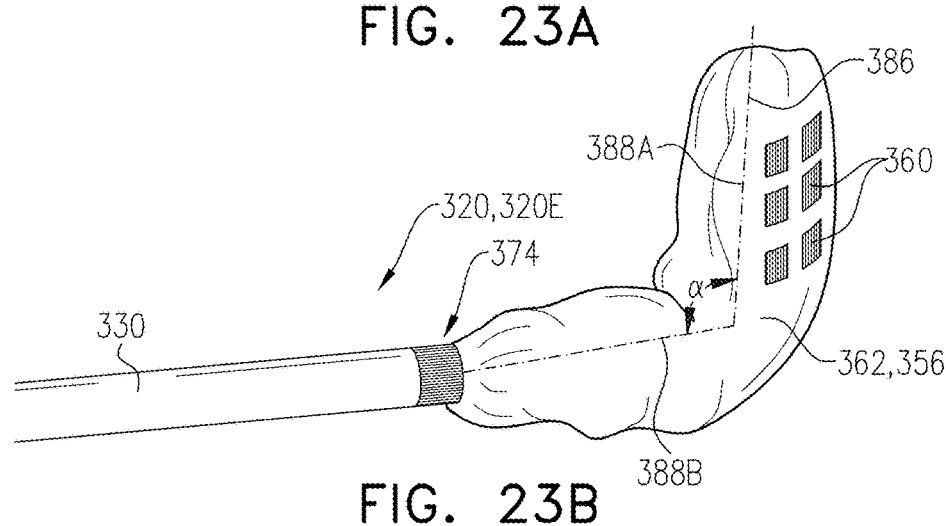

Reference is now made to FIGS. 22 and 23A-B, which are schematic illustrations of an SPG stimulating device 320E for stimulating SPG 22 of patient 24 from within nasal cavity 326, in accordance with an application of the present invention FIG. 22 also shows a method for stimulating SPG 22 using SPG stimulating device 320E, in accordance with an application of the present invention.

Figure 24A:
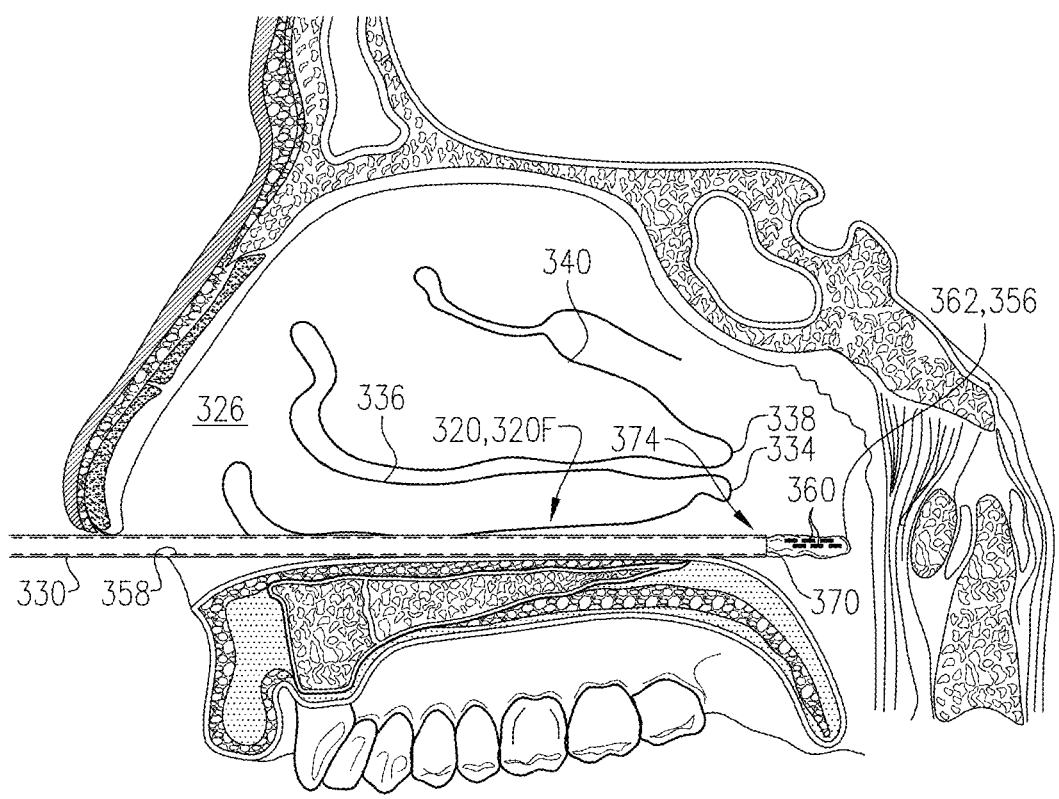
FIGS. 24A-C are schematic illustrations of another SPG stimulating device and a method for stimulating the SPG from within the nasal cavity using the SPG stimulating device, in accordance with respective applications of the present invention.
Figure 24B:
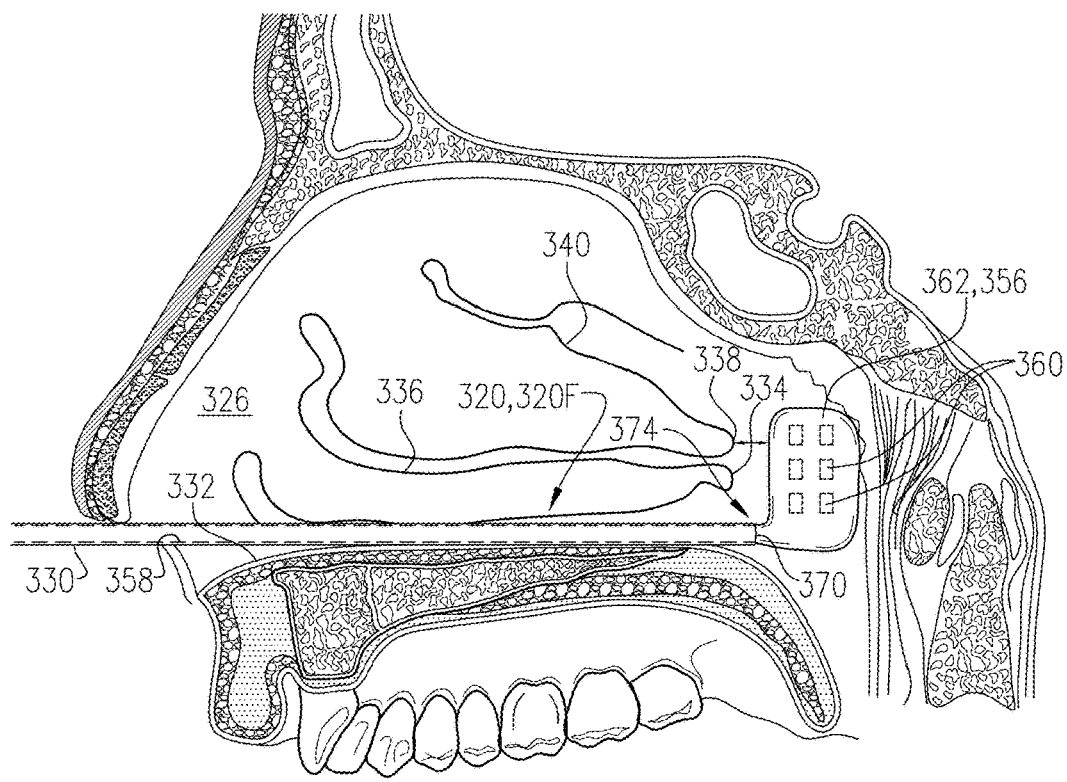
Figure 24C:
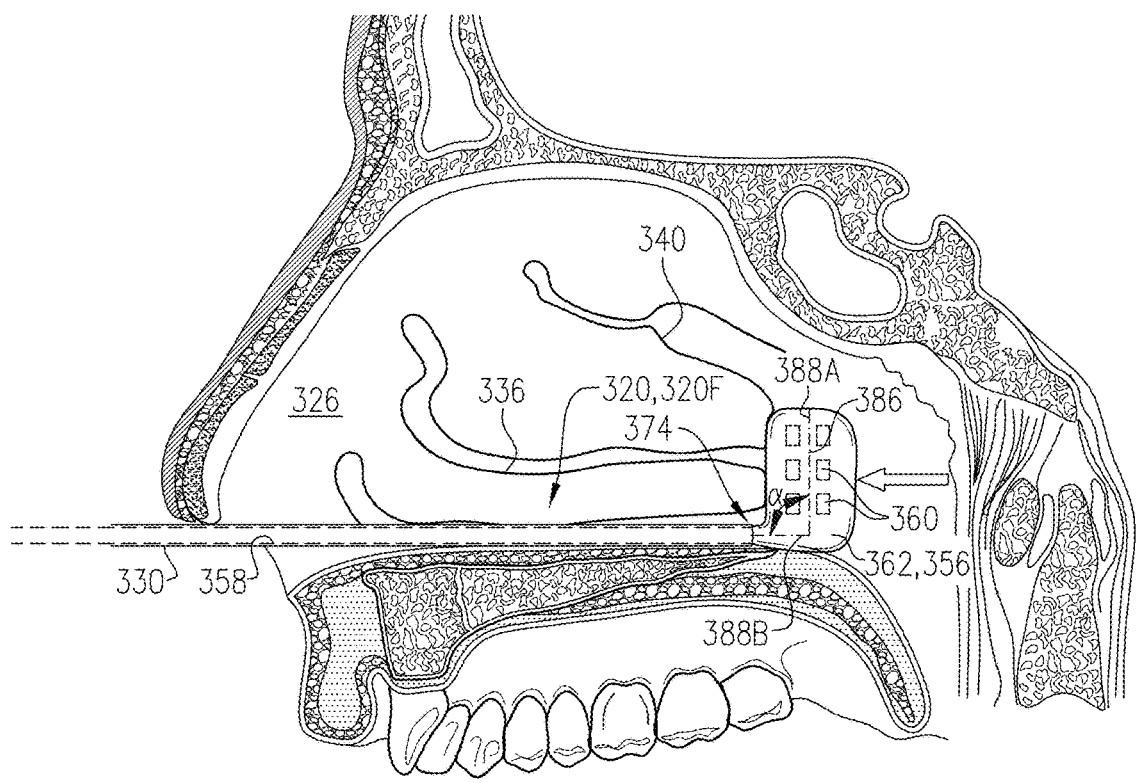

Reference is also made to FIGS. 24A-C, which are schematic illustrations of an SPG stimulating device 320F and a method for stimulating SPG 22 of patient 24 from within nasal cavity 326 using SPG stimulating device 320F, in accordance with respective applications of the present invention.

SPG stimulating devices 320E and 320F are implementations of SPG stimulating device 320 described hereinabove with reference to FIG. 15, and may implement any of the techniques described hereinabove with reference to FIG. 15, 16A-C, 17A-D, 18A-C, 19, and/or 20A-C, mutatis *mutandis*.

Electrode mount 362 of SPG stimulating device 320E comprises an inflatable electrode mount 356, and the one or more electrodes 360 are coupled to an external surface of inflatable electrode mount 356. For example, the one or more electrodes 360 may be conductively printed or sputtered onto inflatable electrode mount 356, or adhered to inflatable electrode mount 356 with an adhesive. Electrode mount 362 is configured, upon inflation of inflatable electrode mount 356, to superiorly deploy the one or more electrodes 360 and position the one or more electrodes 360 against wall 364 of nasal cavity 326 for stimulating SPG 22. Optionally, SPG stimulating device 320 comprises inflation actuator 158, described hereinabove with reference to FIGS. 12A-B and 13. Inflatable electrode mount 356 may be either elastic or generally non-elastic. Typically, the one or more electrodes 360 are generally non-elastic.

SPG stimulating devices 320E and 320F may optionally be implementations of nasal SPG stimulating device 148, described hereinabove with reference to FIGS. 12A-B and 13 (SPG stimulating device 148') and FIGS. 14A-C(SPG stimulating device 148"), and may implement any of the features of these stimulating devices, mutatis *mutandis*. Thus, tube 330 may flexible, distal end portion 374 may comprise inflatable electrode mount 356, and/or a proximal end portion of tube 330 may comprise inflation actuator 158 via which inflatable electrode mount 356 is inflatable.

For some applications, such as shown in FIGS. 23B and 24B-C, inflatable electrode mount 356, when inflated and unconstrained, has a long axis 386 that is generally L-shaped (but does not necessarily define a right angle).

For other applications (configuration not shown), inflatable electrode mount 356, when inflated and unconstrained, has a long axis that is arcuate.

Alternatively or additionally, for some applications, such as shown in FIGS. 23B and 24B-C, inflatable electrode mount 356, when inflated and unconstrained, has long axis 386 that has a distal segment 388A and a proximal segment 388B that define an angle α (alpha) of 30-150 degrees therebetween.

For some applications, such as in an unshown position prior to deployment from distal end opening 370 of tube 330, as shown in FIGS. 22 and 24A, inflatable electrode mount 356 is removably disposed in tube 330 while inflatable electrode mount 356 is in an uninflated state. Inflatable electrode mount 356 is configured, upon the deployment from tube 330 and the inflation of inflatable electrode mount 356, to superiorly deploy the one or more electrodes 360 and position the one or more electrodes 360 against wall 364 of nasal cavity 326 for stimulating SPG 22. Typically, in these applications, inflatable electrode mount 356 is coupled to a distal end of a deployment shaft 358, which passes through tube 330 (such that tube 330 functions as a deployment sheath).

For some applications, electrode mount 362 is coupled to distal end portion 374 of tube 330, such as to distal end 378 of tube 330.

For some applications, SPG stimulating device 320 comprises camera 90, described hereinabove with reference to FIGS. 5A-C and 6A-B and/or FIGS. 12A-B and 13, mutatis mutandis.

For some applications, as shown in the transition between FIGS. 24B and 24C, middle turbinate 340 (e.g., posterior end 338 thereof) is used to assist positioning and/or stabilizing electrode mount 362. For example, as shown in FIG. 24B, electrode mount 362 may be initially positioned posteriorly to middle turbinate 340, and then pulled back anteriorly until electrode mount 362 contacts inferior turbinate 336 and/or middle turbinate 340, indicating that electrode mount 362 is positioned correctly for SPG stimulation.

For some applications, during deployment of SPG stimulating device 320, multiple motions may be performed in order to place the device in the correct position such that the one or more electrodes 360, either already exposed, or after a subsequent deployment, are positioned correctly. For example, once electrode mount 362 contacts the posterior wall of the nasopharynx, the device may be pulled anteriorly a distance to align the electrical contacts in the correct location. A feature of the device could also be deployed during these steps to index the device off internal anatomy. For example, once the distal end of electrode mount 362 is past the intended location of stimulation (e.g., contacts the posterior wall of the nasopharynx), a balloon can be deployed such that when the device is retracted slightly, the balloon lodges against other features of the anatomy (e.g., inferior turbinate 336 and/or middle turbinate 340, as described above) and resists further anterior/proximal retraction. At this point, the device is correctly correct positioned.

Figure 25A:
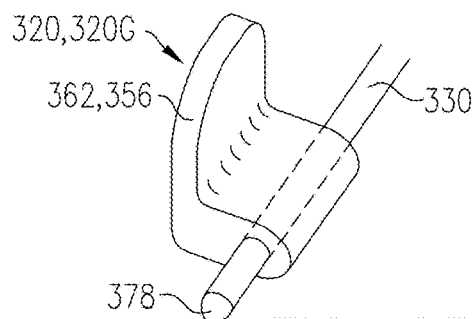
FIGS. 25A-C are schematic illustrations of an SPG stimulating device for stimulating the SPG from within the nasal cavity, in accordance with an application of the present invention.
Figure 25B:
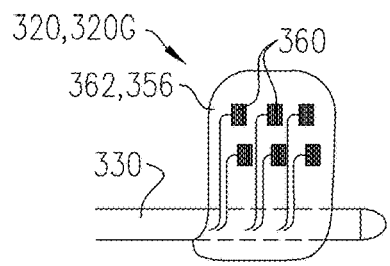
Figure 25C:
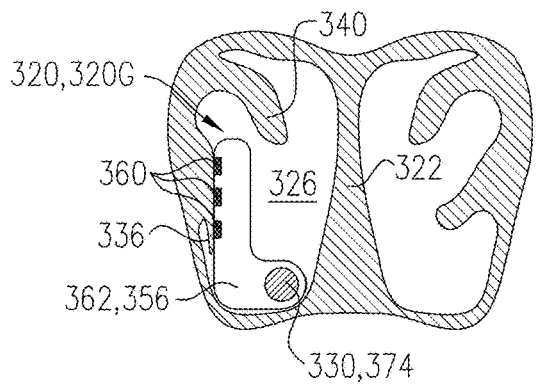

Reference is now made to FIGS. 25A-C, which are schematic illustrations of an SPG stimulating device 320G for stimulating SPG 22 of patient 24 from within nasal cavity 326, in accordance with an application of the present invention. SPG stimulating device 320G is one implementation of SPG stimulating device 320 described hereinabove with reference to FIG. 15, and may implement any of the techniques described hereinabove with reference to FIG. 15, 16A-C, 17A-D, 18A-C, 19, 20A-C, 22, 23A-B, and/or 24A-C, mutatis mutandis. Other than as described below, SPG stimulating device 320G is similar to SPG stimulating device 320E, described hereinabove with reference to FIGS. 22 and 23A-B, and to SPG stimulating device 320F, described hereinabove with reference to FIGS. 24A-C, and may implement any features thereof, mutatis mutandis.

Electrode mount 362 of SPG stimulating device 320G is coupled to distal end portion 374 of tube 330 (but not necessarily to distal end 378 of tube 330), and configured to extend laterally from distal end portion 374 of tube 330 when deployed superiorly away from tube 330. Typically, in this configuration, electrode mount 362 is disposed entirely proximal to distal end 378 of tube 330. For example, electrode mount 362 may comprise:

an inflatable electrode mount 356, or
a flexible material having a shape memory to assume the extended state when unconstrained; for example, the flexible material may comprise a braided or woven structure, e.g., shaped generally as a basket, e.g., comprising Nitinol or polymer strands, or a solid foam.

Inflatable electrode mount 356 of SPG stimulating device 320G may have any of the shape characteristics described hereinabove with reference to FIGS. 23A-B regarding inflatable electrode mount 356 of SPG stimulating device 320E, mutatis mutandis. Typically, only a portion of inflatable electrode mount 356 of SPG stimulating device 320G extends superiorly away from tube 330.

Figure 26A:
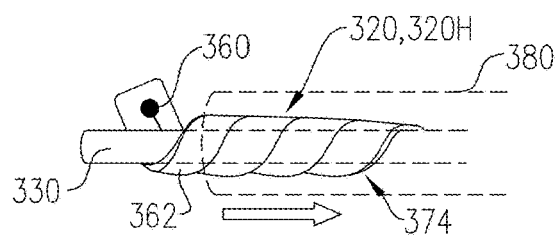
FIGS. 26A-B are schematic illustrations of another SPG stimulating device for stimulating the SPG from within the nasal cavity, in accordance with an application of the present invention.
Figure 26B:
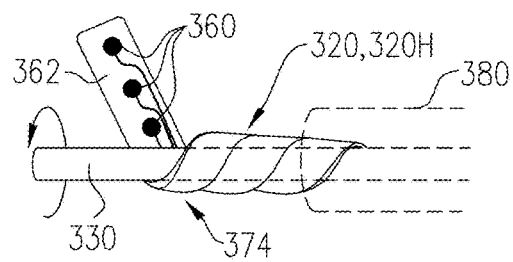

Reference is now made to FIGS. 26A-B, which are schematic illustrations of an SPG stimulating device 320H for stimulating SPG 22 of patient 24 from within nasal cavity 326, in accordance with an application of the present invention. SPG stimulating device 320H is one implementation of SPG stimulating device 320 described hereinabove with reference to FIG. 15, and may implement any of the techniques described hereinabove with reference to FIG. 15, 16A-C, 17A-D, 19, and/or 20A-C, mutatis mutandis.

In this configuration, electrode mount 362 is elongate and is removably constrained coiled around distal end portion 374 of tube 330, such as by deployment sheath 380, such as shown in FIG. 26A. Alternatively, electrode mount 362 is removably constrained coiled around an elongate empty space. Electrode mount 362 is configured, upon being released from being constrained, to at least partially uncoil, such as shown in FIG. 25B, so as to superiorly deploy the one or more electrodes 360 and position the one or more electrodes 360 against wall 364 of nasal cavity 326 for stimulating SPG 22.

Figure 27:
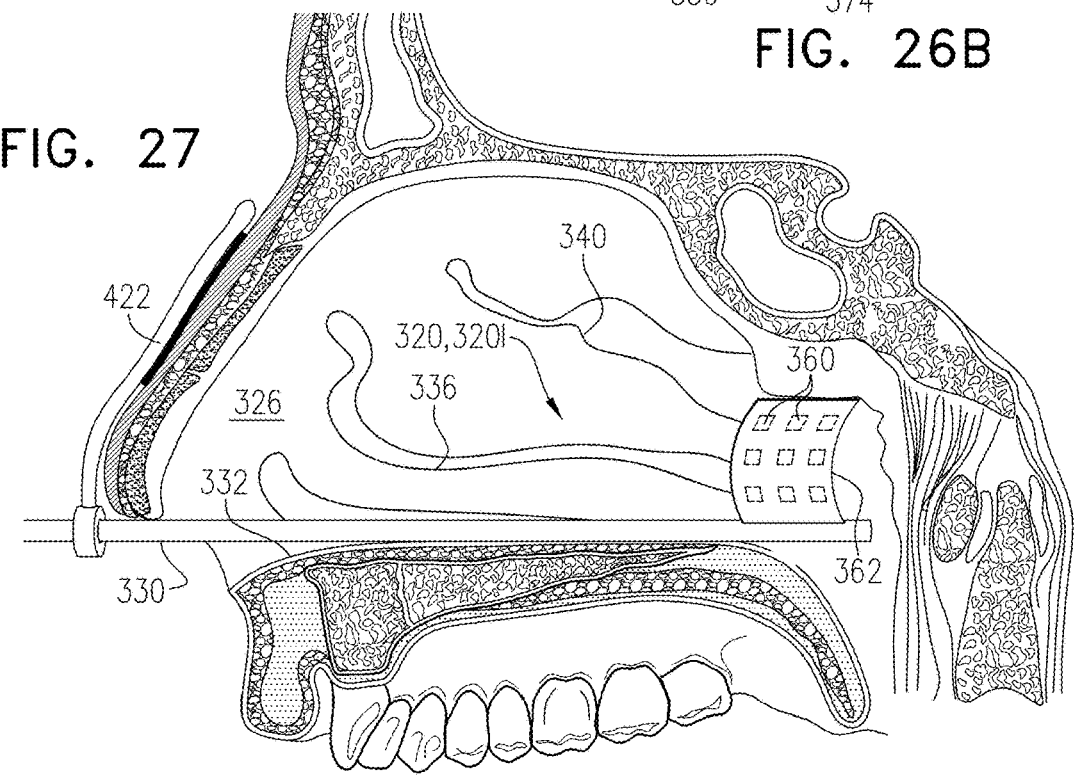
FIG. 27 is a schematic illustration of still another SPG stimulating device for stimulating the SPG from within the nasal cavity, in accordance with an application of the present invention.

Reference is now made to FIG. 27, which is a schematic illustration of an SPG stimulating device 320I for stimulating SPG 22 of patient 24 from within nasal cavity 326, in accordance with an application of the present invention. SPG stimulating device 320I is one implementation of SPG stimulating device 320 described hereinabove with reference to FIG. 15, and may implement any of the techniques described hereinabove with reference to FIG. 15, 16A-C, 17A-D, 19, 20A-C, 22, 23A-B, and/or 24A-C, mutatis mutandis. In this configuration, electrode mount 362 comprises an adhesive and flexible material that complies with the surface of lateral wall 364A of nasal cavity 326.

Figure 28A:
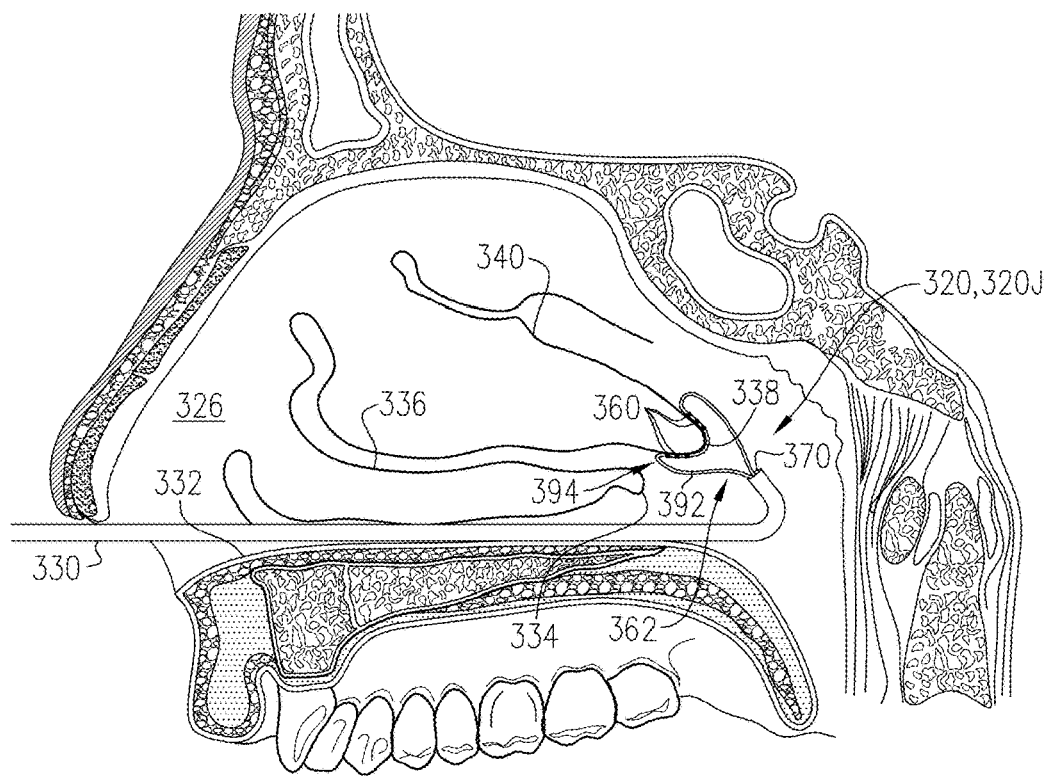
FIGS. 28A-B are schematic illustrations of yet another SPG stimulating device for stimulating the SPG from within the nasal cavity, in accordance with respective applications of the present invention.
Figure 28B:
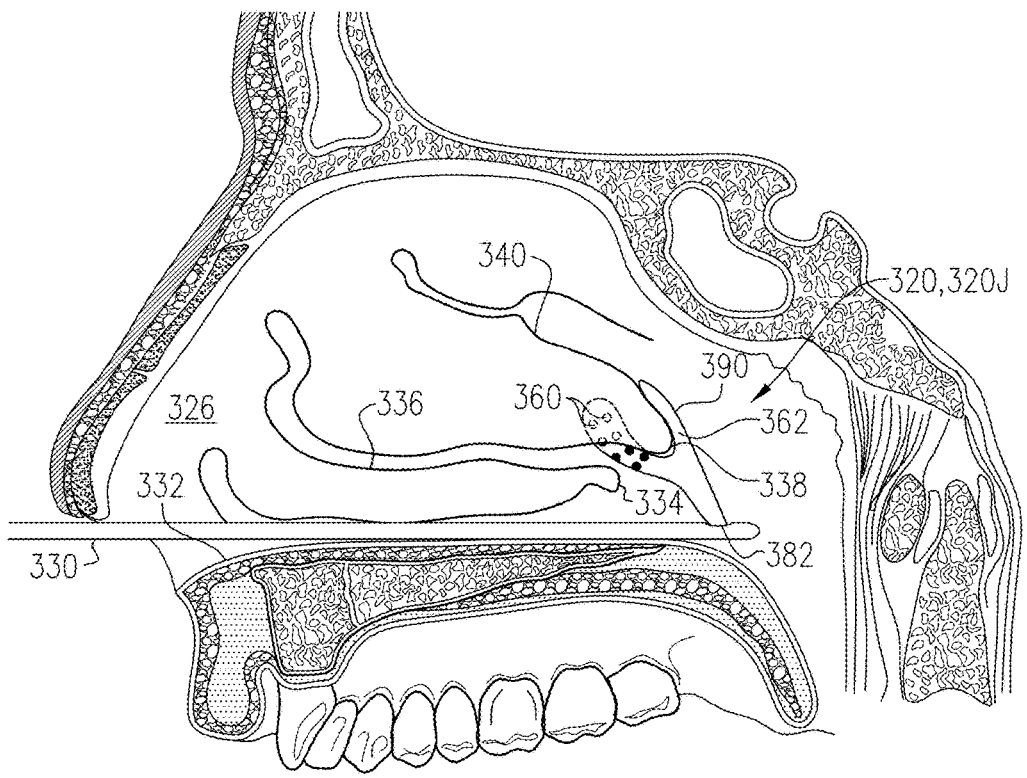

Reference is now made to FIGS. 28A-B, which are schematic illustrations of an SPG stimulating device 320J for stimulating SPG 22 of patient 24 from within nasal cavity 326, in accordance with respective applications of the present invention. SPG stimulating device 320J is one implementation of SPG stimulating device 320 described hereinabove with reference to FIG. 15, and may implement any of the techniques described hereinabove with reference to FIG. 15, 16A-C, 17A-D, 19, 20A-C, 22, 23A-B, and/or 24A-C, mutatis *mutandis*.

Reference is further made FIGS. 29A-B, which are schematic illustrations of SPG stimulating device 320J, in accordance with an application of the present invention. FIGS. 29A-B show posterior cross-sectional views of the anatomy.

In these configurations, electrode mount 362 is shaped so as to hug and catch posterior end 338 of middle turbinate 340 where the middle turbinate attaches to lateral wall 364A of nasal cavity 326. In the configuration shown in FIG. 28A, electrode mount 362 comprises a flexible wire 392, such as described in more detail hereinbelow with reference to FIGS. 30A-C. In the configuration shown in FIG. 28B, electrode mount 362 comprises paddle 390.

In the configurations shown in FIGS. 28A-B, the one or more electrodes 360 are flat, while in the configurations shown in FIGS. 29A-B, the one or more electrodes 360 comprise ring electrodes.

Reference is now made to FIGS. 30A-C, which are schematic illustrations of an SPG stimulating device 320K for stimulating SPG 22 of patient 24 from within nasal cavity 326, in accordance with an application of the present invention. SPG stimulating device 320K is one implementation of SPG stimulating device 320 described hereinabove with reference to FIG. 15, and may implement any of the techniques described hereinabove with reference to FIG. 15, 16A-C, 17A-D, 19, 20A-C, 22, 23A-B, 24A-C, 28A-B, and/or 29A-B, mutatis *mutandis*.

In this configuration, electrode mount 362 comprises flexible wire 392, to which the one or more electrode 360 are fixed. Flexible wire 392 is configured to be shaped as a loop 394 upon deployment, such as shown, for example, in FIG. 28A. For example, flexible wire 392 may be superiorly deployed from tube 330 either via side opening 382 (such as shown in FIGS. 30A-C) or distal end opening 370 (not shown in FIGS. 30A-C, but shown, for example, in FIG. 28A (and FIGS. 16A-C, 17A-D, 18A-C, and 22)).

Figure 31A:
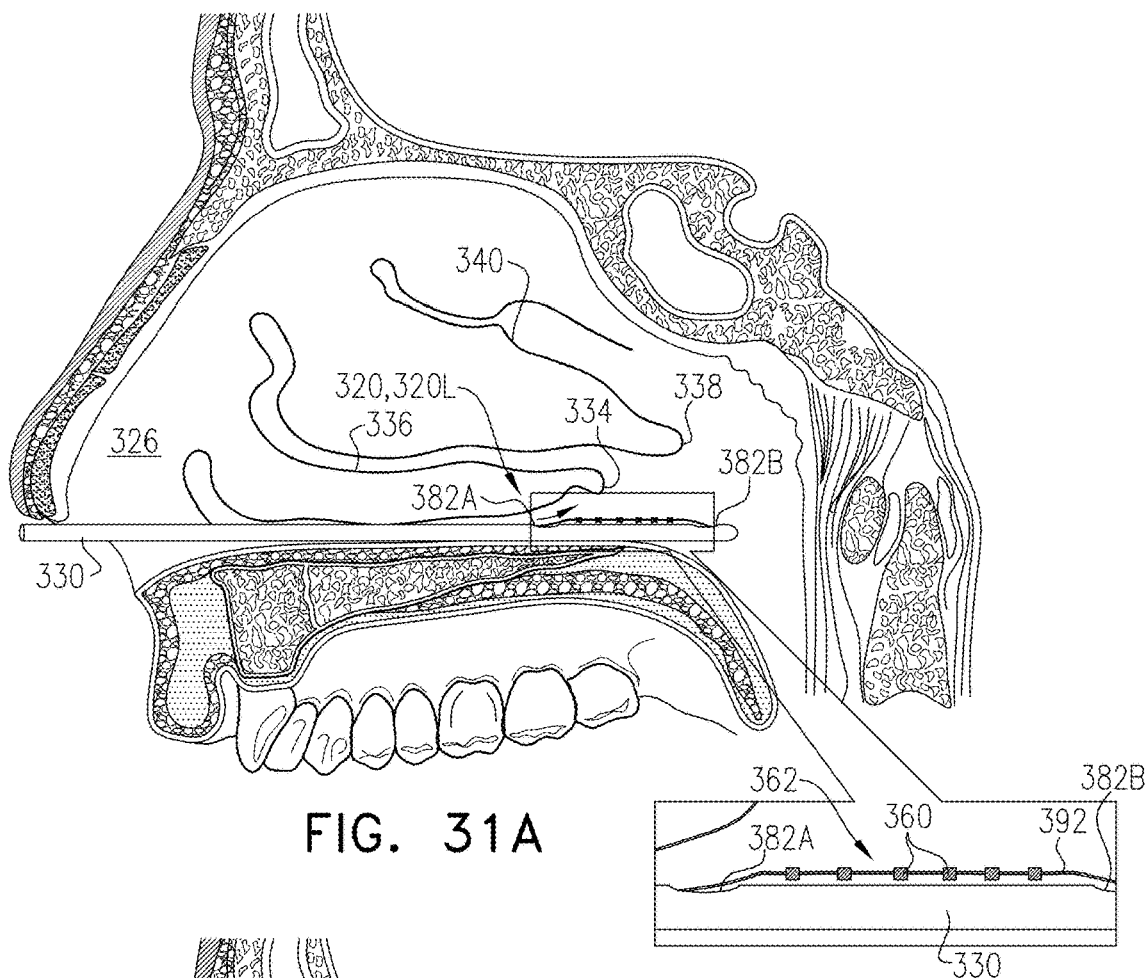
FIGS. 31A-C are schematic illustrations of still another SPG stimulating device and a method for stimulating the SPG from within the nasal cavity using the SPG stimulating device, in accordance with respective applications of the present invention.
Figure 31B:
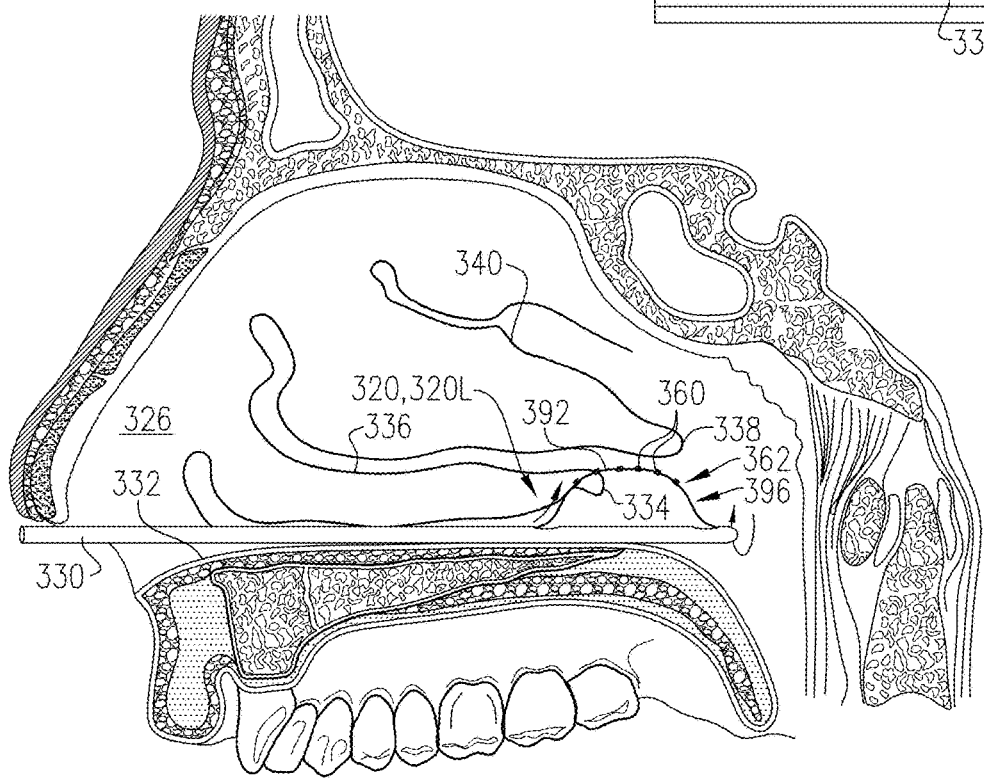
Figure 31C:
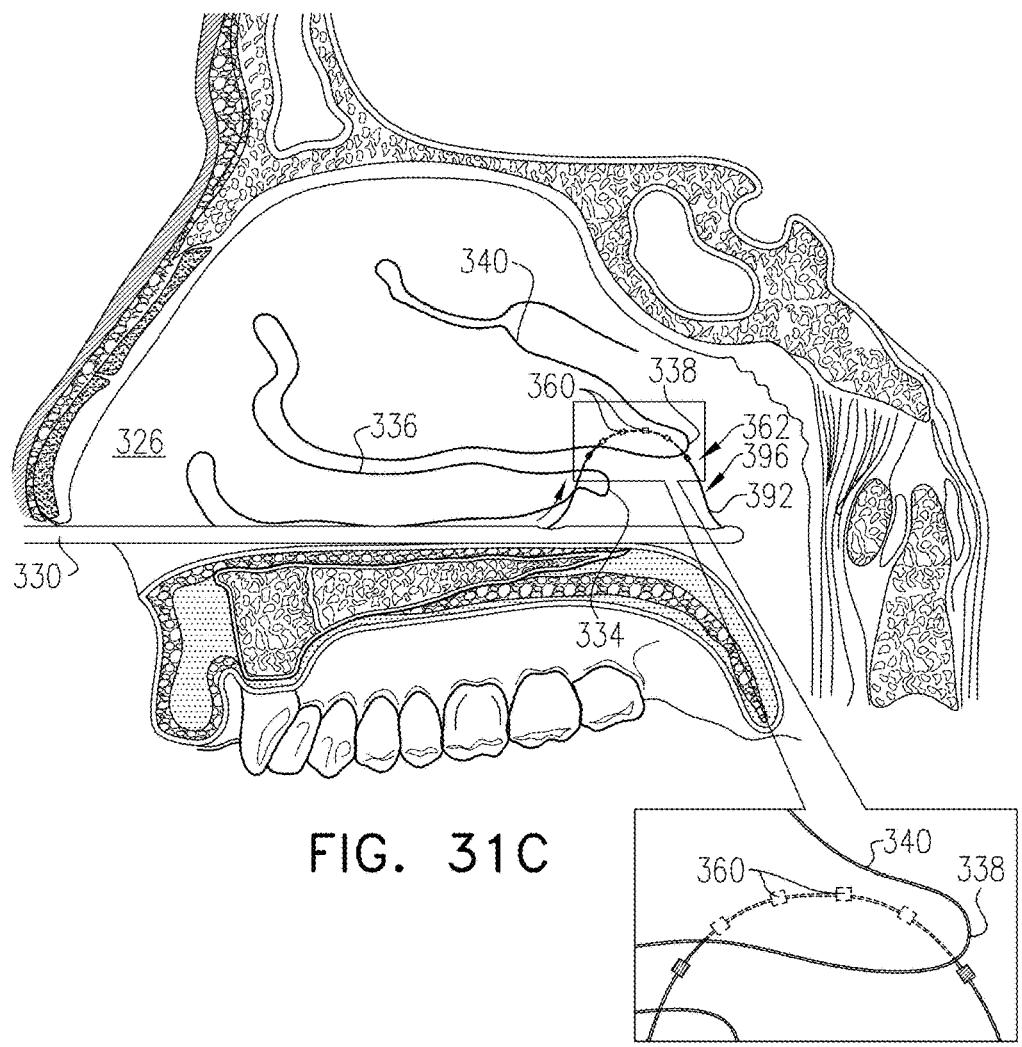

Reference is now made to FIGS. 31A-C, which are schematic illustrations of an SPG stimulating device 320L and a method for stimulating SPG 22 of patient 24 from within nasal cavity 326 using SPG stimulating device 320L, in accordance with respective applications of the present invention. SPG stimulating device 320L is one implementation of SPG stimulating device 320 described hereinabove with reference to FIG. 15, and may implement any of the techniques described hereinabove with reference to FIG. 15, 16A-C, 17A-D, 19, 20A-C, 22, 23A-B, 24A-C, 28A-B, and/or 29A-B, mutatis *mutandis*. SPG stimulating device 320L is similar in some respects to SPG stimulating device 320K, described hereinabove with reference to FIGS. 30A-C.

Figure 32:
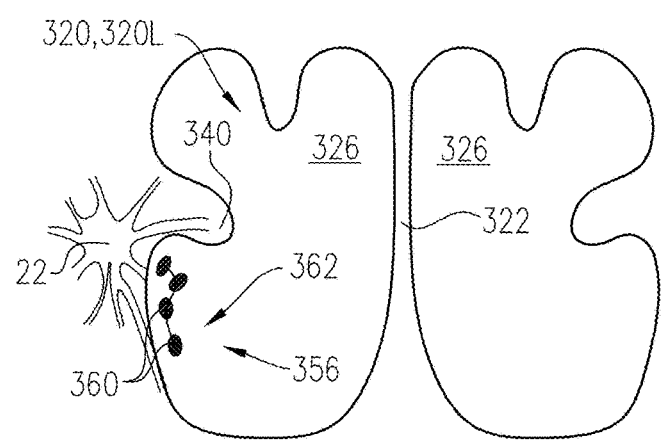
FIG. 32 is a schematic illustration of the SPG stimulating device of FIGS. 31A-C deployed in the nasal cavity for stimulating the SPG within the nasal cavity, in accordance with an application of the present invention.

Reference is further made FIG. 32, which is a schematic illustration of SPG stimulating device 320L deployed in nasal cavity 326 for stimulating SPG 22 of patient 24 from within the nasal cavity, in accordance with an application of the present invention. FIG. 32 shows a cross-sectional view of the anatomy.

In this configuration, electrode mount 362 comprises flexible wire 392, to which the one or more electrode 360 are fixed. Flexible wire 392 is configured to be shaped as a curve 396 upon deployment. For example, flexible wire 392 may be superiorly deployed (such as by pushing) from tube 330 via first and second side openings 382A and 382B defined by tube 330. During deployment of flexible wire 392, as curve 396 rises above inferior turbinate 336, tube 330 can be rotated such that electrode mount 362 turns toward and presses against lateral wall 364A of nasal cavity 326. Further deployment of flexible wire 392 from tube 330 causes the flexible wire to continue to rise underneath middle turbinate 340.

Figure 33A:
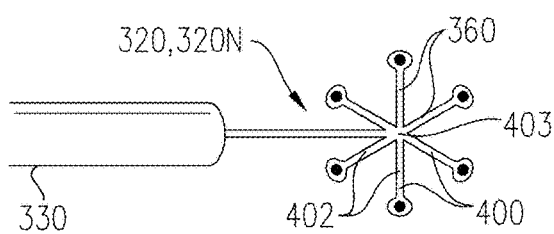
FIGS. 33A-B are schematic illustrations of an SPG stimulating device for stimulating the SPG from within the nasal cavity, in accordance with an application of the present invention.
Figure 33B:
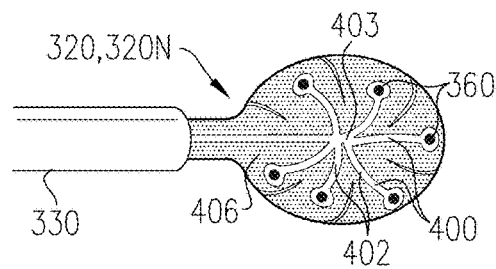

Reference is now made to FIGS. 33A-B, which are schematic illustrations of an SPG stimulating device 320N for stimulating SPG 22 of patient 24 from within nasal cavity 326, in accordance with an application of the present invention. SPG stimulating device 320N is one implementation of SPG stimulating device 320 described hereinabove with reference to FIG. 15, and may implement any of the techniques described herein, mutatis *mutandis*.

Figure 34A:
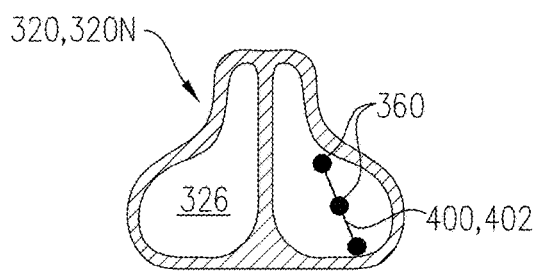
FIGS. 34A-B are schematic illustrations of the SPG stimulating device of FIGS. 33A-B deployed in the nasal cavity for stimulating the SPG from within the nasal cavity, in accordance with an application of the present invention.
Figure 34B:
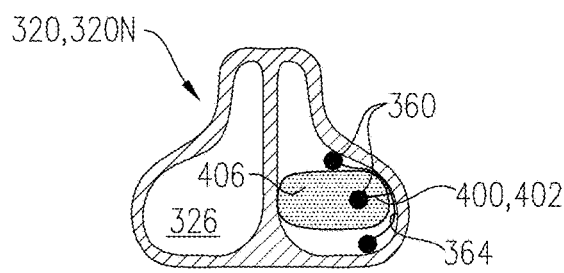

Reference is further made to FIGS. 34A-B, which are schematic illustrations of SPG stimulating device 320N deployed in nasal cavity 326 for stimulating SPG 22 of patient 24 from within the nasal cavity, in accordance with an application of the present invention.

Figure 35A:
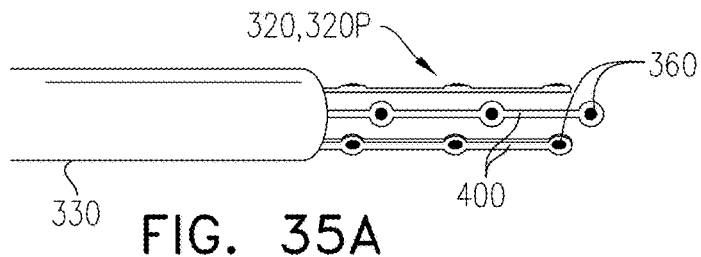
FIGS. 35A-C are schematic illustrations of another SPG stimulating device for stimulating the SPG from within the nasal cavity, in accordance with an application of the present invention.
Figure 35B:
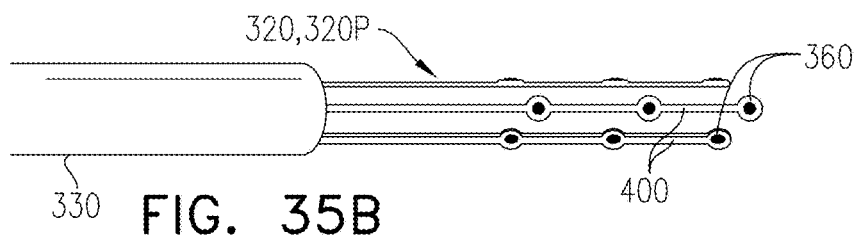
Figure 35C:
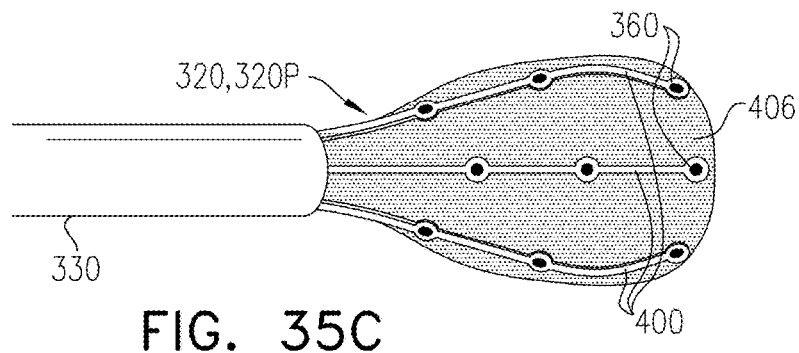

Reference is still further made to FIGS. 35A-C, which are schematic illustrations of an SPG stimulating device 320P for stimulating SPG 22 of patient 24 from within nasal cavity 326, in accordance with an application of the present invention. SPG stimulating device 320P is one implementation of SPG stimulating device 320 described hereinabove with reference to FIG. 15, and may implement any of the techniques described herein, mutatis *mutandis*. SPG stimulating device 320P is similar in some respects to SPG stimulating device 320N, described hereinabove with reference to FIGS. 33A-B and 34A-B.

Figure 36:
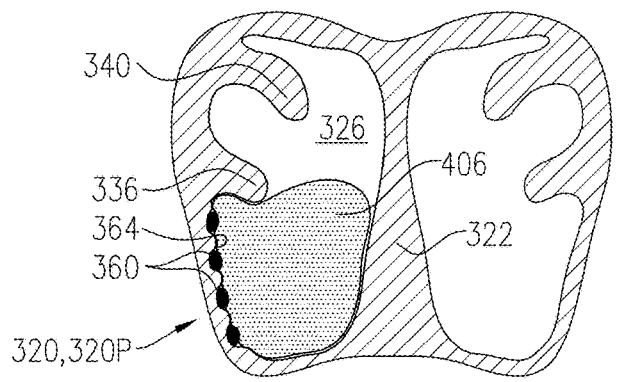
FIG. 36 is a schematic illustration of the SPG stimulating device of FIGS. 35A-C deployed in the nasal cavity for stimulating the SPG from within the nasal cavity, in accordance with an application of the present invention.

Reference is further made to FIG. 36, which is a schematic illustration of SPG stimulating device 320P deployed in nasal cavity 326 for stimulating SPG 22 of patient 24 from within the nasal cavity, in accordance with an application of the present invention.

Figure 37A:
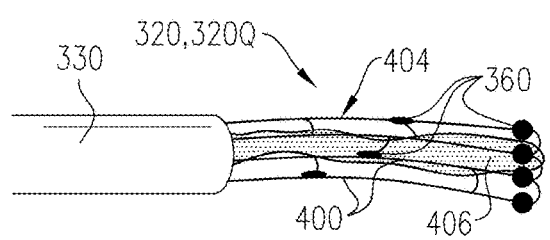
FIGS. 37A-B are schematic illustrations of still another SPG stimulating device for stimulating the SPG from within the nasal cavity, in accordance with an application of the present invention.
Figure 37B:
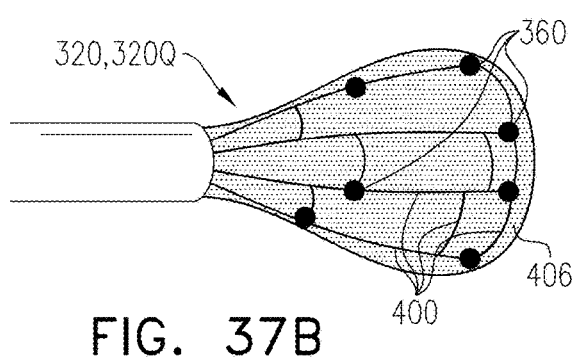

Reference is additionally made to FIGS. 37A-B, which are schematic illustrations of an SPG stimulating device 320Q for stimulating SPG 22 of patient 24 from within nasal cavity 326, in accordance with an application of the present invention. SPG stimulating device 320Q is one implementation of SPG stimulating device 320 described hereinabove with reference to FIG. 15, and may implement any of the techniques described herein, mutatis *mutandis*. SPG stimulating device 320Q is similar in some respects to SPG stimulating device 320N, described hereinabove with reference to FIGS. 33A-B and 34A-B, and to SPG stimulating device 320P, described hereinabove with reference to FIGS. 35A-C and 36.

Electrode mount 362 of SPG stimulating devices 320N, 320P, and 320Q comprises a plurality of struts 400, to which the one or more electrodes 360 are fixed (along and/or at ends of the struts). Struts 400 may comprise electrical conduits (e.g., wires or traces) or such electrical conduits may be separate from struts 400. Struts 400 may, for example, be arranged:
  as spokes 402, e.g., radiating from a hub 403, such as shown in FIGS. 33A-B and 34A-B,
  alongside one another, such as shown in FIGS. 35A-C and 36, or
  as a frame 404, e.g., a partial basket, such as shown in FIGS. 37A-B.

SPG stimulating devices 320N, 320P, and 320Q further comprise a balloon 406, which is typically not fixed to struts 400, which may allow some relative motion between balloon 406 and struts 400. During deployment of SPG stimulating devices 320N, 320P, and 320Q, balloon 406 is inflated in order to press struts 400 into wall 364 of nasal cavity 326, such as shown in FIG. 34B for SPG stimulating device 320N and in FIG. 36 for SPG stimulating device 320P (the deployment of SPG stimulating device 320Q appears similar to the SPG stimulating device 320P shown in FIG. 36). This pressing causes struts 400 to conform to the shape of wall 364.

For some applications, struts 400 are arranged on only one side of balloon 406, i.e., do not surround balloon 406, while for other applications, struts 400 surround balloon 406.

Optionally, struts 400 may comprise a springy and flexible material, such that struts 400 have some structural integrity of their own, but rely in part of balloon 406 to orient and/or hold struts 400 in place against wall 364 of nasal cavity 326. Alternatively, struts 400 may comprise a highly flexible or conformable material, which has little structural integrity and relies substantially entirely on balloon 406 to set and maintain the shape of the struts; for example, the material may comprise a polymeric or flexible wire mesh.

For some applications, struts 400 comprise a plastically deformable material, e.g., a malleable material, that retains the shape that balloon 406 imparts on the struts, similar in some respects to a balloon-deployed malleable stent. The plastically deformable, e.g., malleable, material may allow at least partial deflation of balloon 406 after deployment of the struts. Balloon 406 may be left within nasal cavity 326 during the deployment procedure, or removed from nasal cavity 326 during the deployment procedure.

Optionally, during deployment prior to inflation of balloon 406, a test SPG stimulation is performed and/or a physiological or electrical signal is measured to ascertain whether the one or more electrodes 360 are optimally positioned to stimulate SPG 22 and/or branches extending from SPG 22. Once the correct location of the one or more electrodes 360 for SPG stimulation has been ascertained, balloon 406 is inflated.

Figure 38A:
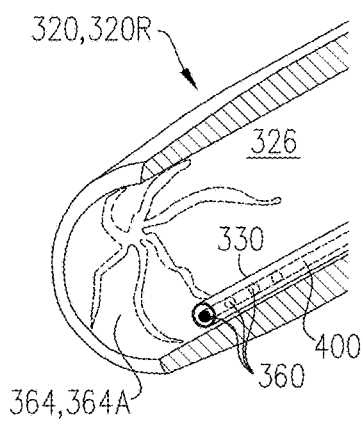
FIGS. 38A-C are schematic illustrations of yet another SPG stimulating device and a method for stimulating the SPG from within the nasal cavity using the SPG stimulating device, in accordance with respective applications of the present invention.
Figure 38B:
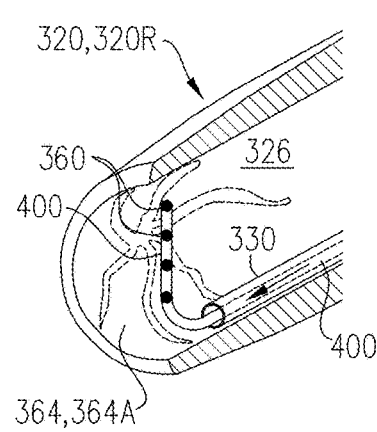
Figure 38C:
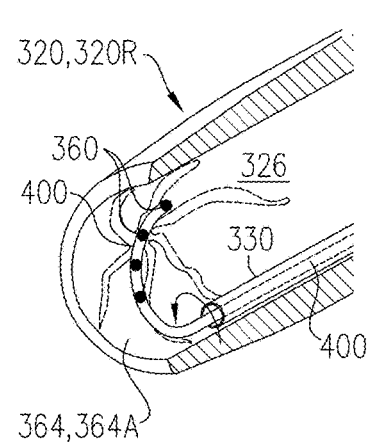

Reference is now made to FIGS. 38A-C, which are schematic illustrations of an SPG stimulating device 320R and a method for stimulating SPG 22 of patient 24 from within nasal cavity 326 using SPG stimulating device 320R, in accordance with respective applications of the present invention. SPG stimulating device 320R is one implementation of SPG stimulating device 320 described hereinabove with reference to FIG. 15, and may implement any of the techniques described herein, mutatis mutandis.

Electrode mount 362 of SPG stimulating device 320R comprises a strut 400, to which the one or more electrodes 360 are fixed (along and/or at ends of the struts). Strut 400 may be flexible or plastically deformable (e.g., malleable), and is configured, when pressed against wall 364 of nasal cavity 326, to conform to the curved shape of wall 364.

Figure 40:
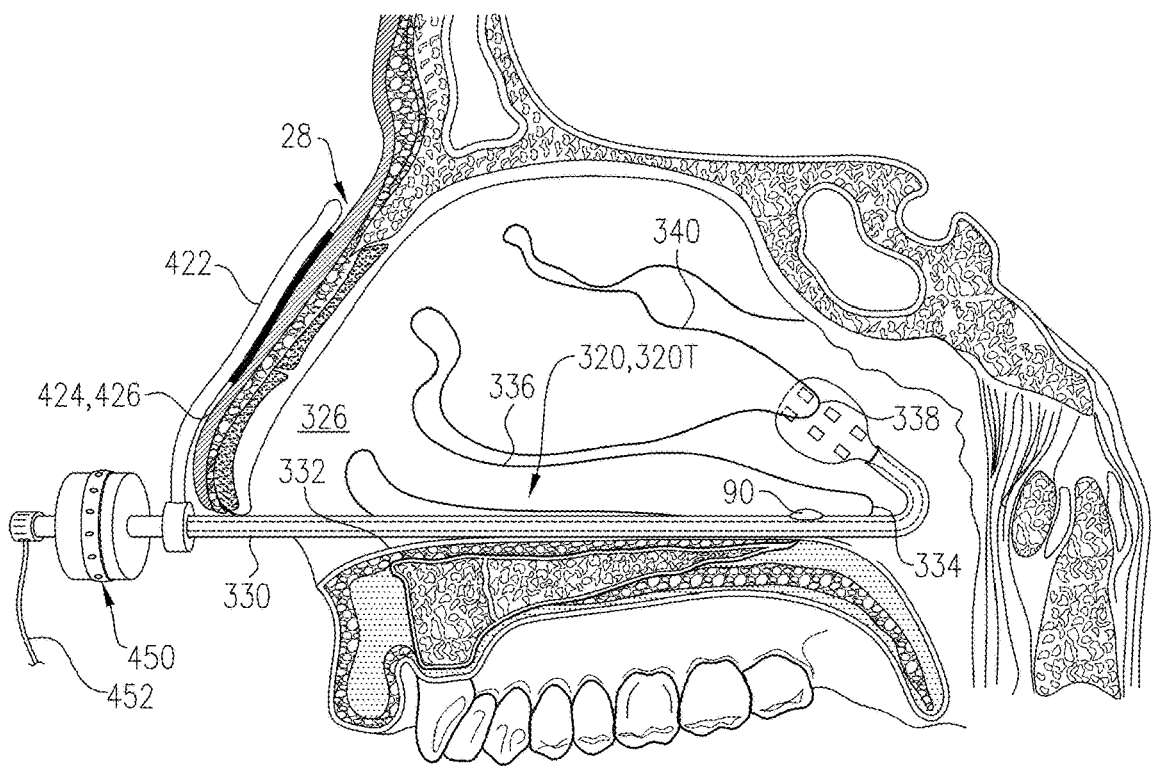
FIG. 40 is a schematic illustration of another SPG stimulating device for stimulating the SPG from within the nasal cavity, in accordance with an application of the present invention.

Reference is made to FIGS. 15, 16A-C, 17A-D, 21A-C, 22, 24A-C, 27, 28A-B, 29A-B, 31A-C, and 34A-B, which are described hereinabove. Reference is further made to FIG. 40, which is described hereinbelow.

Reference is still further made to FIGS. 39A-E, which are schematic illustrations of an SPG stimulating device 320S and a method for stimulating SPG 22 of patient 24 from within nasal cavity 326 using SPG stimulating device 320S, in accordance with respective applications of the present invention. SPG stimulating device 320S is one implementation of SPG stimulating device 320 described hereinabove with reference to FIG. 15, and may implement any of the techniques described hereinabove with reference to FIG. 15 and/or any of the other figures described herein, mutatis mutandis.

In some applications of the present invention, a method is provided for stimulating SPG 22 of the patient. As shown in FIGS. 15, 16A, 17A, 21A, 24A, 31A, 38B, and 39A, tube 330 and electrode mount 362 are inserted into nasal cavity 326 of the patient and tube 330 is advanced along floor 332 of nasal cavity 326 to near posterior end 334 of inferior turbinate 336. For example, the correct depth of insertion may be ascertained by a visual marker on the device, direct visualization via camera 90, a physical stop (for example, a flange against the nostril that prevents further insertion, or by the distal portion of the device contacting the posterior wall of the nasopharynx), and/or or by a specific anatomical landmark.

For some applications, tube 330 is sufficiently rigid (while optionally still somewhat flexible) to be advanced by itself within nasal cavity, such as shown in FIGS. 16A-C, 17A-D, 21A-C, 22, 24A-C, 27, 28A-B, 31A-C, 38A-C, and 40.

For other applications, deployment sheath 380 is used to advance tube 330 within nasal cavity 326. Deployment sheath 380 is advanced along floor 332 of nasal cavity 326 to near posterior end 334 of inferior turbinate 336, and tube 330 is advanced through deployment sheath 380 along floor 332 of nasal cavity 326 to near posterior end 334 of inferior turbinate 336, such as described hereinabove with reference to FIGS. 18A-C. (The configurations shown in FIGS. 16A-C, 17A-D, 21A-C, 22, 24A-C, 27, 28A-B, 31A-C, 38A-C, and 40 may optionally also employ deployment sheath 380.)

Figure 39A:
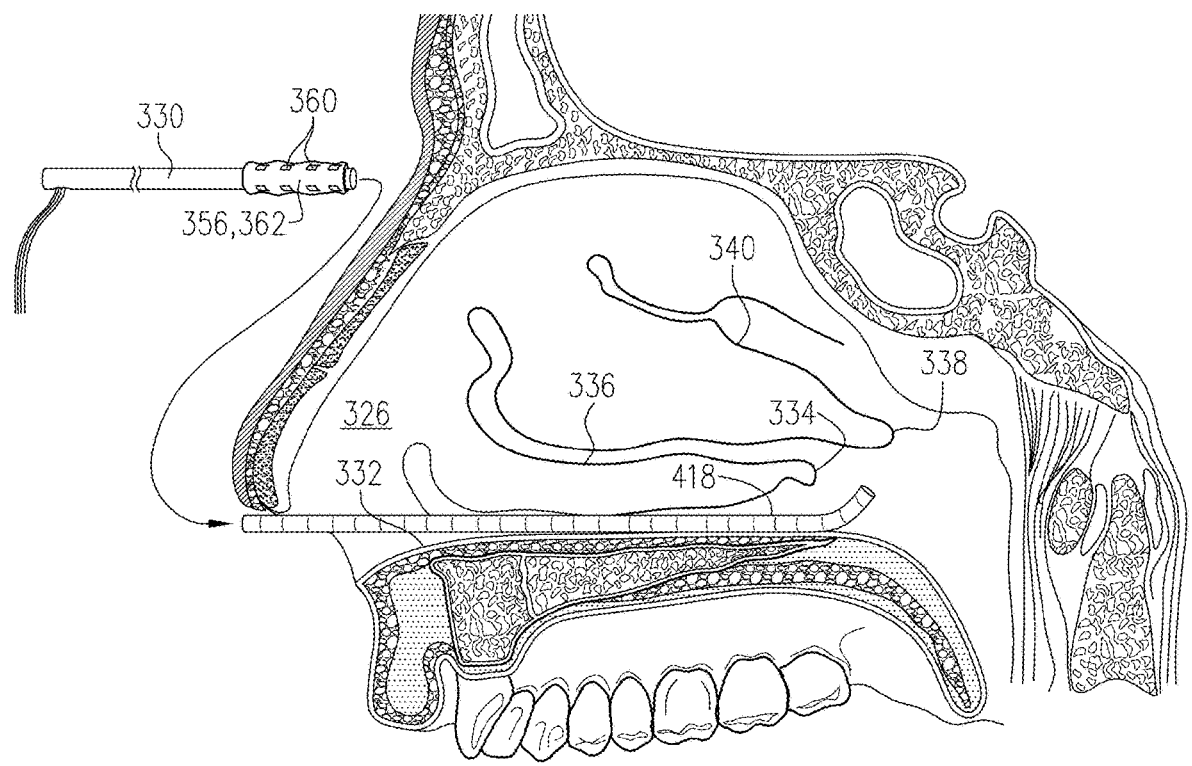
FIGS. 39A-E are schematic illustrations of an SPG stimulating device and a method for stimulating the SPG from within the nasal cavity using the SPG stimulating device, in accordance with respective applications of the present invention.
Figure 39B:
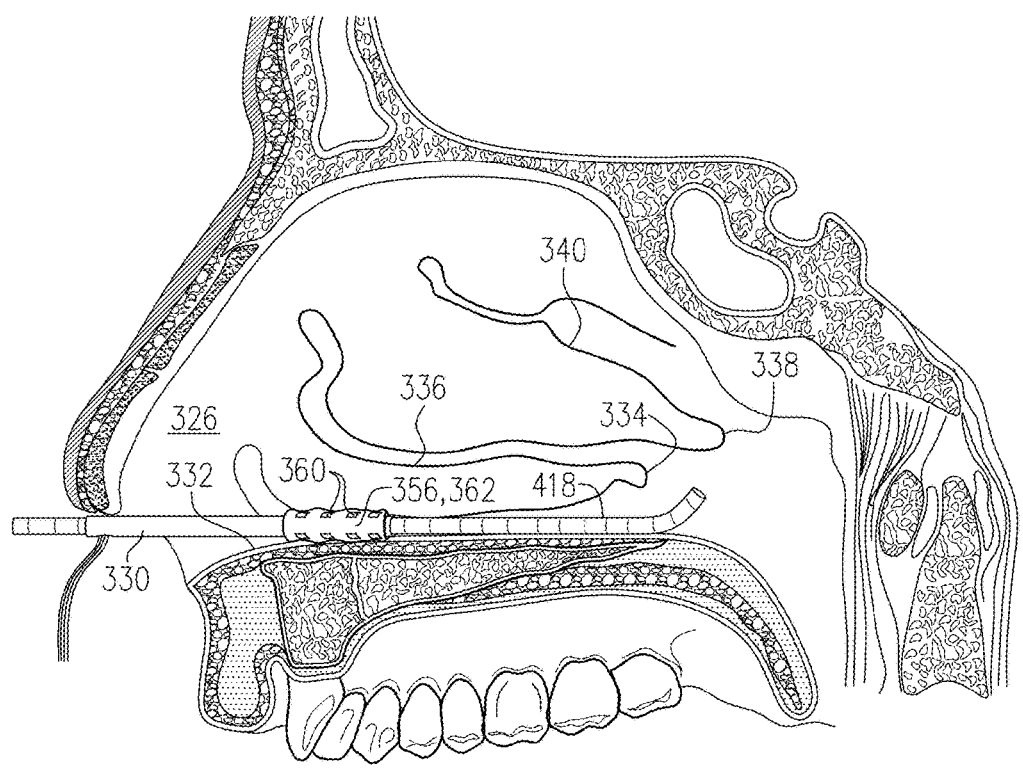
Figure 39C:
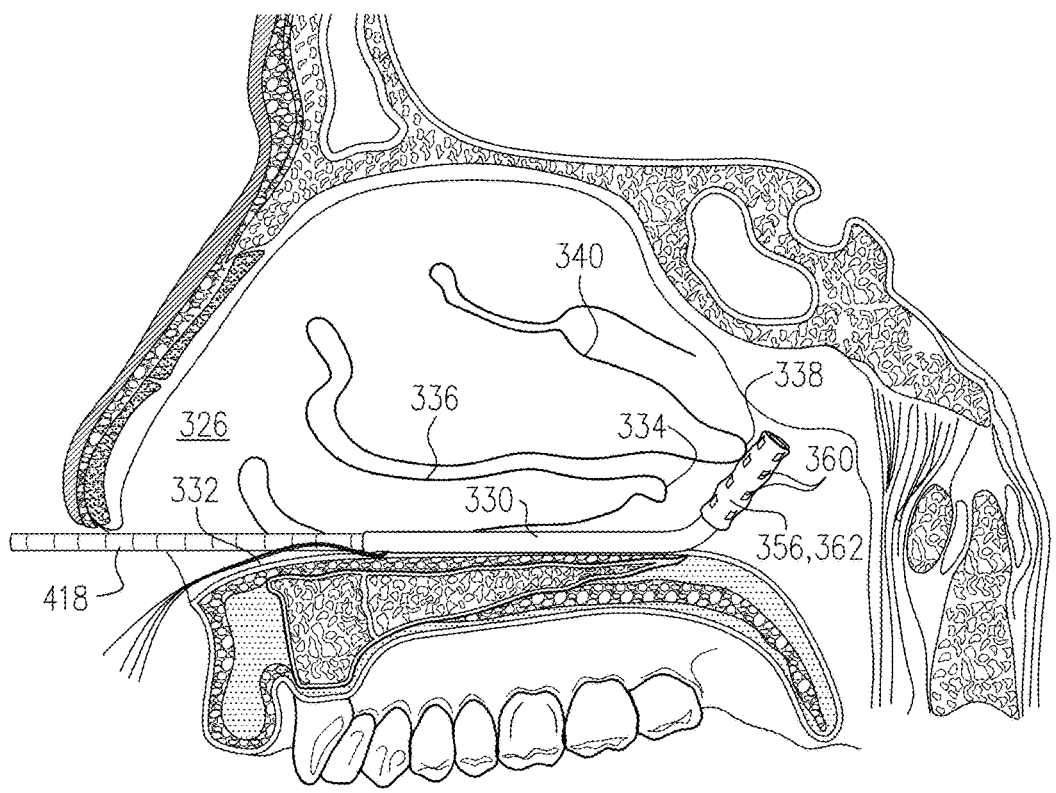
Figure 39D:
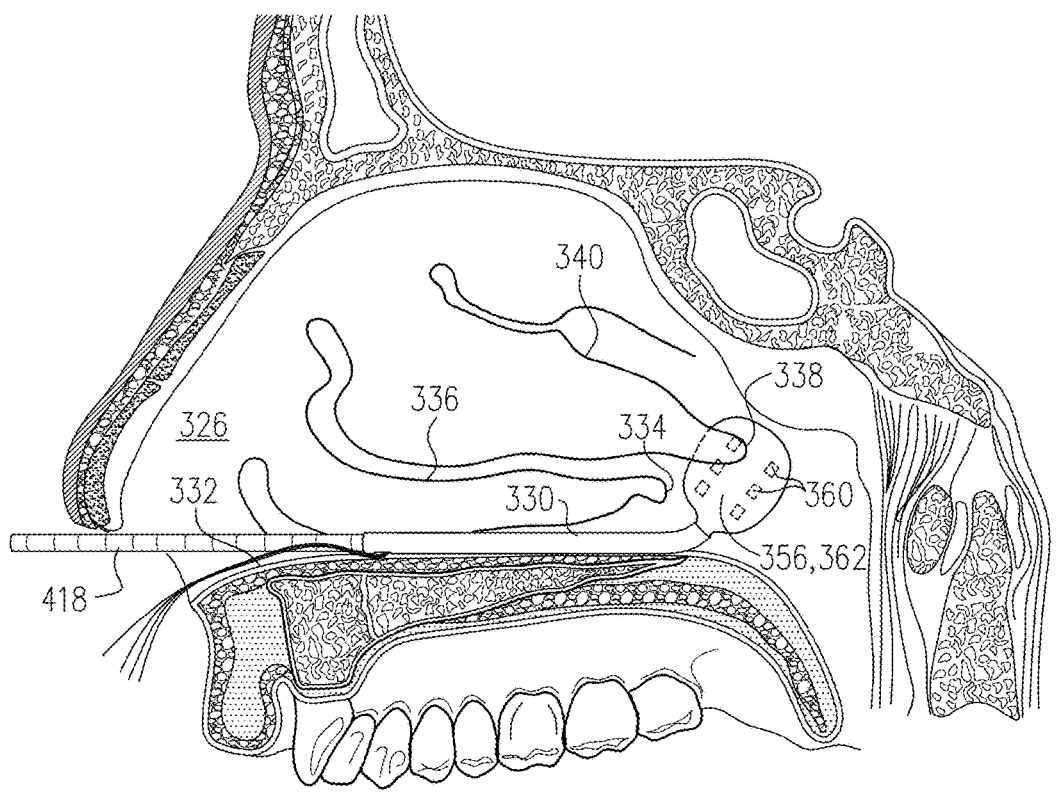
Figure 39E:
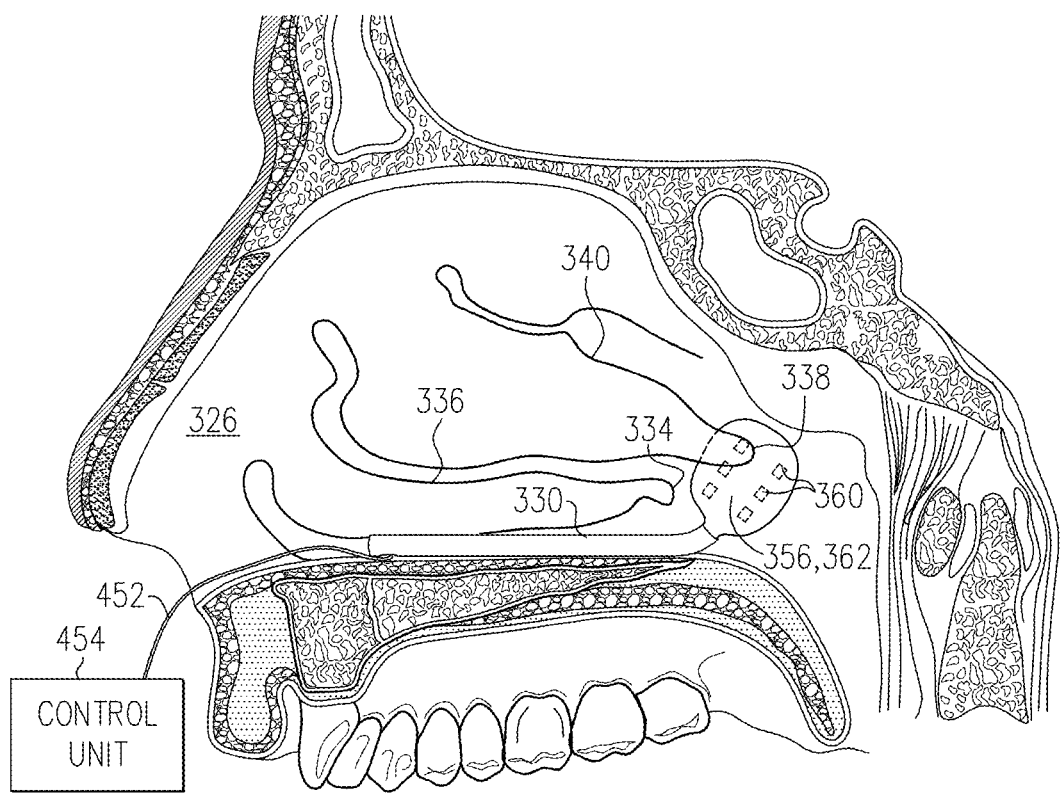

For still other applications, an elongate guide member 418 is used to advance tube 330 within nasal cavity 326. Guide member 418 is advanced along floor 332 of nasal cavity 326 to near posterior end 334 of inferior turbinate 336, such as shown in FIG. 39A. Tube 330 is advanced over guide member 418 along floor 332 of nasal cavity 326 to near posterior end 334 of inferior turbinate 336, such as shown in FIGS. 39B-C. Guide member 418 is withdrawn from tube 330, as shown in the transition between FIGS. 39D and 39E. For example, guide member 418 may comprise a guide rail or guidewire. Optionally, guide member 418 is steerable, e.g., a distal end portion of guide member 418 is deflectable, such as described hereinabove regarding distal end portion 374 of tube 330 with reference to FIGS. 16A-C and 17A-D, mutatis mutandis.

As shown in FIGS. 15, 16B-C, 17B-D, 21B-C, 22, 24B-C, 25C, 27, 28A-B, 29A-B, 31B-C, 32, 34B, 36, 38C, and 39C-E, one or more electrodes 360 of electrode mount 362 are deployed superiorly away from tube 330 while tube 330 is disposed along floor 332 of nasal cavity 326 and electrode mount 362 is disposed within nasal cavity 326, so as to bring at least one of the one or more electrodes 360 into contact with lateral wall 364A of nasal cavity 326 at an area of middle meatus 366, near posterior end 334 of inferior turbinate 336 and posterior end 338 of middle turbinate 340 and an area of sphenopalatine foramen 368. The correct location of the one or more electrodes 360 may be ascertained, for example, by a visual marker on the device, direct visualization via camera 90, a physical stop (for example, if device is pulled back, indication from pressure sensor), and/or by a specific anatomical landmark. The superior deployment of the one or more electrodes 360 may be implemented by deflecting distal end portion 374 of tube 330, such as described hereinabove with reference to FIGS. 16A-C and 17A-D and/or as shown in FIGS. 39A-E and 40, and/or by a change in shape of electrode mount 362, such as described hereinabove with reference to FIGS. 21A-C, 22, 23A-B, 24A-C, 25A-C, 26A-B, 27, 28B, 29A-B, 30A-C, 31A-C, 32, 33A-B, 34A-B, 35A-C, 36, 37A-B, and/or 38A-C.

Optionally, a test SPG stimulation is performed and/or a physiological or electrical signal is measured to ascertain whether the one or more electrodes 360 are optimally positioned to stimulate SPG 22 and/or branches extending from SPG 22.

While the one or more electrodes 360 are in contact with lateral wall 364A of nasal cavity 326, a current configured to stimulate SPG 22 via lateral wall 364A is applied to the one or more electrodes 360.

Reference is made to FIG. 40, which is a schematic illustration of an SPG stimulating device 320T for stimulating SPG 22 of patient 24 from within nasal cavity 326, in accordance with an application of the present invention. SPG stimulating device 320T is one implementation of SPG stimulating device 320 described hereinabove with reference to FIG. 15, and may implement any of the techniques described hereinabove with reference to FIG. 15 and/or any of the other figures described herein, mutatis mutandis.

SPG stimulating device 320T further comprises an external stabilizer 422, which is configured to be coupled to an external surface 424 of the patient, such as skin 426, e.g., skin of an external surface of nose 28, such as shown. For example, external stabilizer 422 may be coupled to skin 426 using an adhesive. External stabilizer 422 is coupled to tube 330, thereby helping secure the one or more electrodes 360 in place upon deployment.

Alternatively, for some applications (configuration not shown), the one or more electrodes 360 are stabilized by an elongate member that is inserted into one of the nostrils, passes behind nasal septum 322, exits the opposite nostril in order to form a loop that is coupled to an element of SPG stimulating device 320, such as tube 330 or electrode mount 362. For example, the elongate member may be similar to or may comprise the AMT Bridle Pro® (Applied Medical Technology, Inc., Brecksville, OH, USA).

Reference is again made to FIG. 40. SPG stimulating device 320 may optionally comprise a steering control 450, for controlling steering of tube 330 or guide member 418, such as described hereinabove. Any of the configurations of SPG stimulating device 320 and SPG stimulating device 420 described herein that implement steering may optionally comprise steering control 450.

Alternatively or additionally, SPG stimulating device 320 may optionally comprise one or more wires 452 for transmitting data and/or power. Any of the configurations of SPG stimulating device 320 420 described herein may optionally comprise the one or more wires 452. Typically, a control unit 454 (schematically shown in FIG. 39E) is provided and configured to drive the one or more electrodes 360 to stimulate SPG 22. Optionally, control unit 454 implements any of the features of control unit 26, described hereinabove with reference to FIGS. 1, 4A-B, 8A-B, 9A-C, and/or 10A-B, mutatis mutandis.

Reference is made to FIGS. 16A-40 and 41A-48D. In some implementations of SPG stimulating device 320 described with reference to FIGS. 16A-40, tube 330 is configured to remain inserted in nasal cavity 326, connected to electrode mount 362, during stimulation of SPG 22. By contrast, in some implementations of an SPG stimulating device 420 described with reference to FIGS. 41A-48D, tube 330 is configured to be disengaged from an electrode mount 462 of SPG stimulating device 420 after deployment of the one or more electrodes 360 in nasal cavity 326. Electrode mount 462 may thus be considered an implant. SPG stimulating device 420 is configured to apply the current to the one or more electrodes 360 to stimulate SPG 22 after tube 330 has been disengaged from electrode mount 462 (and optionally, even before disengagement, such as to perform a test SPG stimulation, such as described hereinabove).

Optionally, electrode mount 462 is configured to enable retrieval of the electrode mount upon completion of the stimulation or for other reasons. For example, electrode mount 462 may be configured to enable deflation of balloon 472 in the configuration described hereinbelow with reference to FIGS. 47A-E.

Figure 41A:
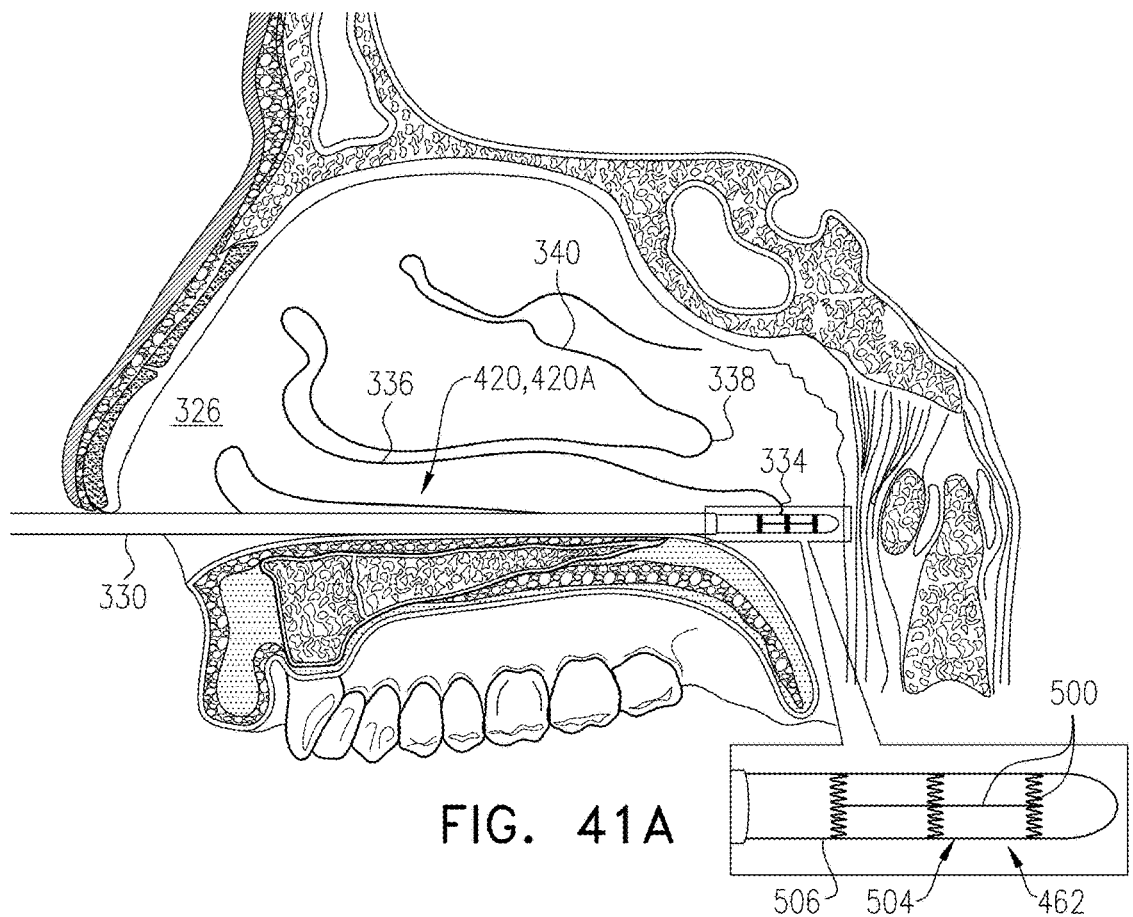
FIGS. 41A-C are schematic illustrations of an SPG stimulating device and a method for stimulating the SPG from within the nasal cavity using the SPG stimulating device, in accordance with respective applications of the present invention.
Figure 41B:
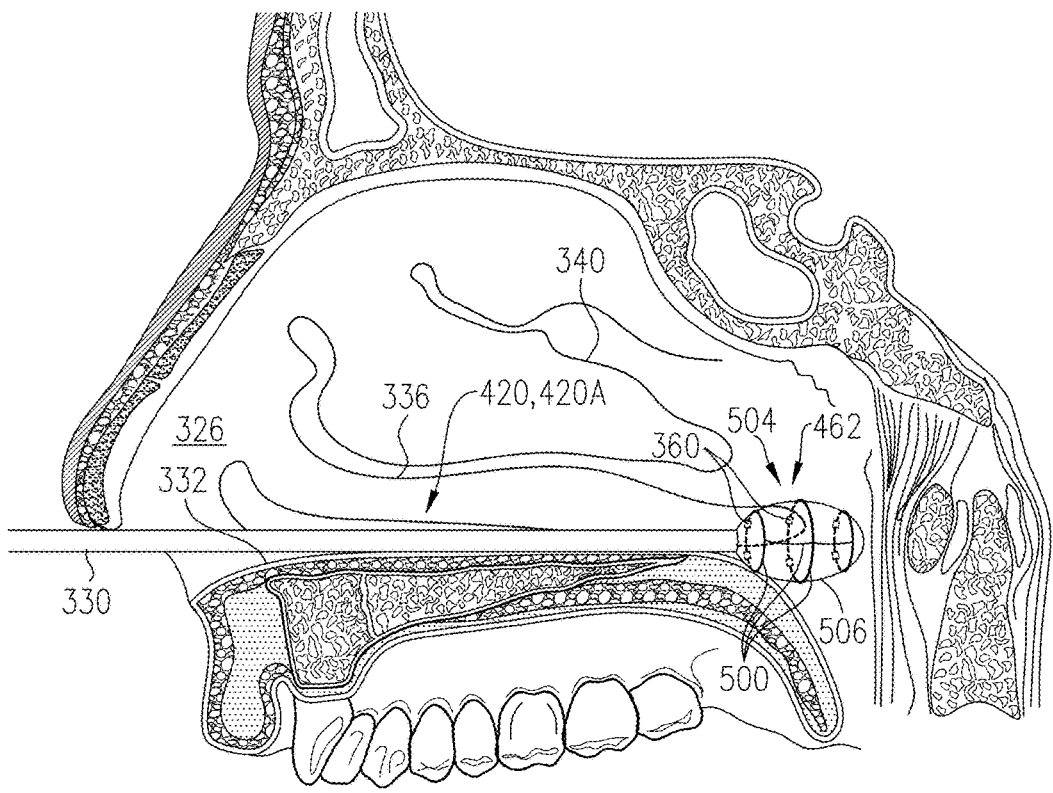
Figure 41C:
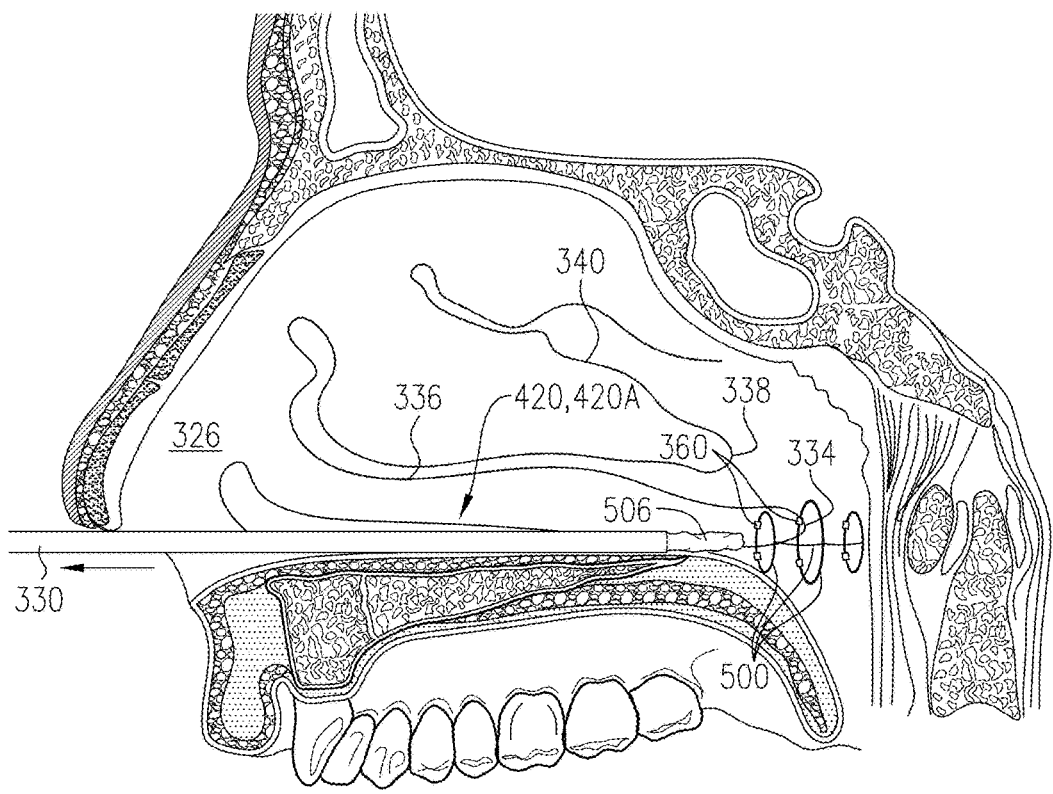

Reference is now made to FIGS. 41A-C, which are schematic illustrations of an SPG stimulating device 420A and a method for stimulating SPG 22 of patient 24 from within nasal cavity 326 using SPG stimulating device 420A, in accordance with respective applications of the present invention.

Reference is further made FIGS. 42A-D, which are schematic illustrations of SPG stimulating device 420A, in accordance with an application of the present invention.

SPG stimulating device 420A is one implementation of SPG stimulating device 420 described hereinabove with reference to FIGS. 41A-48D, and may implement any of the techniques described hereinabove with reference to FIG. 15 and/or the other figures, mutatis mutandis.

For some applications, such as shown in FIGS. 41A-C and 42A-D, electrode mount 462 of SPG stimulating device 420A comprises a plurality of struts 500, to which the one or more electrodes 360 are fixed (along and/or at ends of the struts). Struts 500 may, for example, be arranged as a frame 504, e.g., a basket, such as shown in 41A-C and 42A-D. Struts 500 may alternatively have another arrangement, for example one of the arrangements described hereinabove for struts 400, with respect to FIGS. 33A-B and 34A-B, FIGS. 35A-C and 36, or FIGS. 37A-B. Struts 500 may comprise electrical conduits (e.g., wires or traces), or such electrical conduits may be separate from struts 500; struts 500 are typically electrically insulated at locations other than the one or more electrodes 360.

For some applications, SPG stimulating device 420A comprises a balloon 506 coupled to tube 330. For some applications, struts 500 comprise a plastically deformable material, e.g., a malleable material, that retains the shape that balloon 506 imparts on the struts, similar in some respects to a balloon-deployed malleable stent. Typically, balloon 506 is removed from the struts when tube 330 is disengaged from electrode mount 462.

During a method for stimulating SPG 22 using SPG stimulating device 420A, tube 330 and electrode mount 462 are inserted into nasal cavity 326 of the patient and tube 330 is advanced along floor 332 of nasal cavity 326 to near posterior end 334 of inferior turbinate 336, such as shown in FIG. 41A. Tube 330 is advanced by itself, in deployment sheath 380, or over elongate guide member 418, all as described above, mutatis mutandis.

Figure 42A:
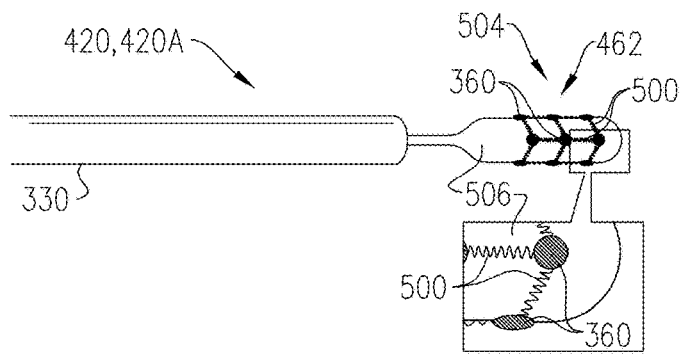
FIGS. 42A-D are schematic illustrations of the SPG stimulating device of FIGS. 41A-C, in accordance with an application of the present invention.
Figure 42B:
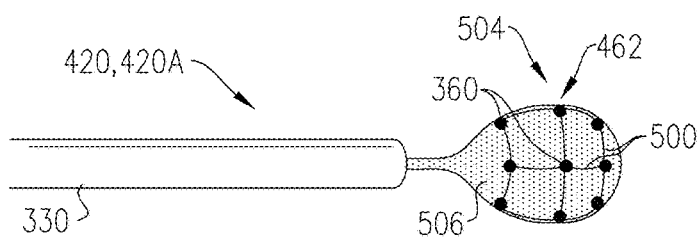

Such as shown in FIGS. 41B and 42A-B, balloon 506 is inflated in order to expand struts 500 of electrode mount 462 and bring the one or more electrodes 360 into contact with lateral wall 364A of nasal cavity 326. Optionally, the one or more electrodes 360 are arranged on only one side of frame 504 (the side facing lateral wall 364A of nasal cavity 326), such as shown; alternatively, the one or more electrodes 360 surround frame 504 (configuration not shown).

Optionally, during deployment prior to inflation of balloon 506, a test SPG stimulation is performed and/or a physiological or electrical signal is measured to ascertain whether the one or more electrodes 360 are optimally positioned to stimulate SPG 22 and/or branches extending from SPG 22. Once the correct location of the one or more electrodes 360 for SPG stimulation has been ascertained, balloon 506 is inflated.

Figure 42C:
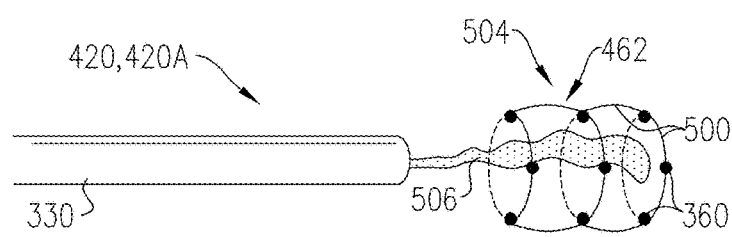
Figure 42D:
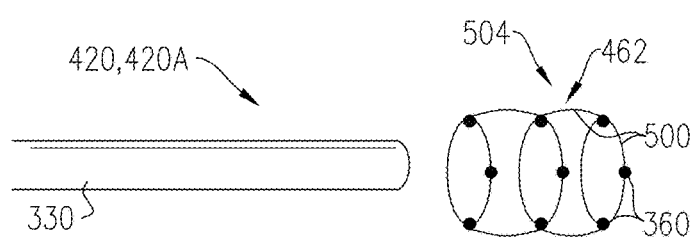

Such as shown in FIGS. 41C and 42C-D, balloon 506 is deflated and removed from electrode mount 462, leaving electrode mount 462 in place. As also shown in FIG. 41C, tube 330 and balloon 506 are removed from nasal cavity 326, leaving electrode mount 462 in place.

While the one or more electrodes 360 are in contact with lateral wall 364A of nasal cavity 326, a current configured to stimulate SPG 22 via lateral wall 364A is applied to the one or more electrodes 360, e.g., by one or more wires or wirelessly, as is known in the implantable electrode stimulation art.

Figure 43:
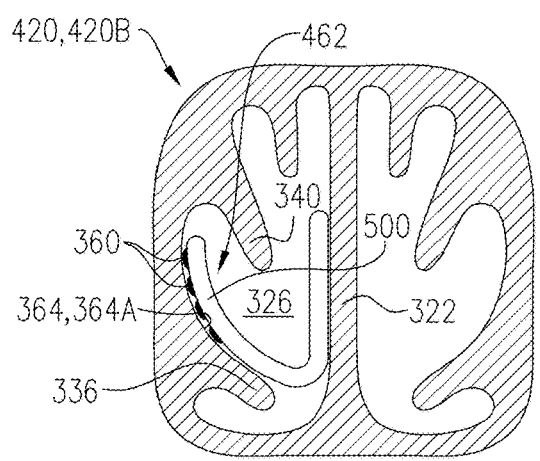
FIG. 43 is a schematic illustration of still another SPG stimulating device for stimulating the SPG from within the nasal cavity, in accordance with an application of the present invention.

Reference is now made to FIG. 43, which is a schematic illustration of an SPG stimulating device 420B for stimulating SPG 22 of patient 24 from within nasal cavity 326, in accordance with an application of the present invention. SPG stimulating device 420B is one implementation of SPG stimulating device 420 described hereinabove with reference to FIGS. 41A-48D, and may implement any of the techniques described hereinabove with reference to FIG. 15 and/or the other figures, mutatis mutandis. In this configuration, electrode mount 462 comprises a springy strut 500, which is configured to be lodged between lateral wall 364A of nasal cavity 326 and nasal septum 322.

Figure 44:
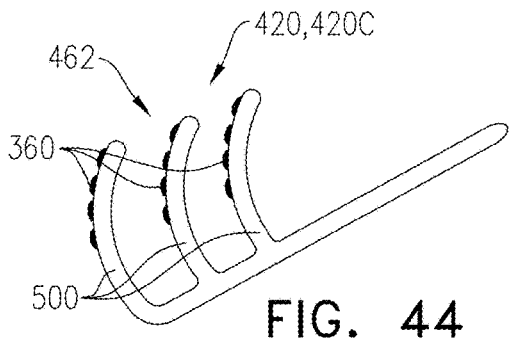
FIG. 44 is a schematic illustration of yet another SPG stimulating device for stimulating the SPG from within the nasal cavity, in accordance with an application of the present invention.

Reference is now made to FIG. 44, which is a schematic illustration of an SPG stimulating device 420C for stimulating SPG 22 of patient 24 from within nasal cavity 326, in accordance with an application of the present invention. SPG stimulating device 420C is one implementation of SPG stimulating device 420 described hereinabove with reference to FIGS. 41A-48D, and may implement any of the techniques described hereinabove with reference to FIG. 15 and/or the other figures, mutatis mutandis. In this configuration, electrode mount 462 comprises one or more curved springy struts 500, which are configured to bring the one or more electrodes into good contact with lateral wall 364A of nasal cavity 326. For example, electrode mount 462 may comprise a plurality of springy struts 500, such as three or four springy struts 500, and one or more of the electrodes are coupled to each of the struts.

Reference is now made to FIGS. 45A and 45B, which are schematic illustrations of another configuration of electrode mount 462, in accordance with an application of the present invention. In this configuration, struts 500 of the electrode mount 462 are arranged as a frame 468, which laterally expands and axially contract to become more spherical, by application of a proximally-directed force via a member, such as a pull wire 470, as shown in the transition between FIG. 45A and FIG. 45B. Electrode mount 462 may be implemented in some of the configurations of SPG stimulating device 320 described herein or in some of the configurations of SPG stimulating device 420 described herein, mutatis mutandis.

Reference is now made to FIG. 46, which is a schematic illustration of an SPG stimulating device 420D for stimulating SPG 22 of patient 24 from within nasal cavity 326, in accordance with an application of the present invention. SPG stimulating device 420D is one implementation of SPG stimulating device 420 described hereinabove with reference to FIGS. 41A-48D, and may implement any of the techniques described hereinabove with reference to FIG. 15 and/or the other figures, mutatis mutandis.

Reference is further made to FIGS. 47A-E, which are schematic illustrations of a method for stimulating SPG 22 using SPG stimulating device 420D, in accordance with an application of the present invention.

In this configuration, electrode mount 462 comprises a plurality of struts 500, which may be flat, e.g., paddle-shaped. One or more struts 500 (e.g., all of struts 500) comprise one or more of electrodes 360. Optionally, only struts 500 on one side of electrode mount 462 comprise electrodes 360. Electrode mount 462 further comprises a balloon 472, to which the struts are coupled. Electrode mount 462 is releasably coupled to tube 330 by a releasable coupling 474. SPG stimulating device 420D further comprises one or more wires 452 for transmitting data and/or power.

Figure 47A:
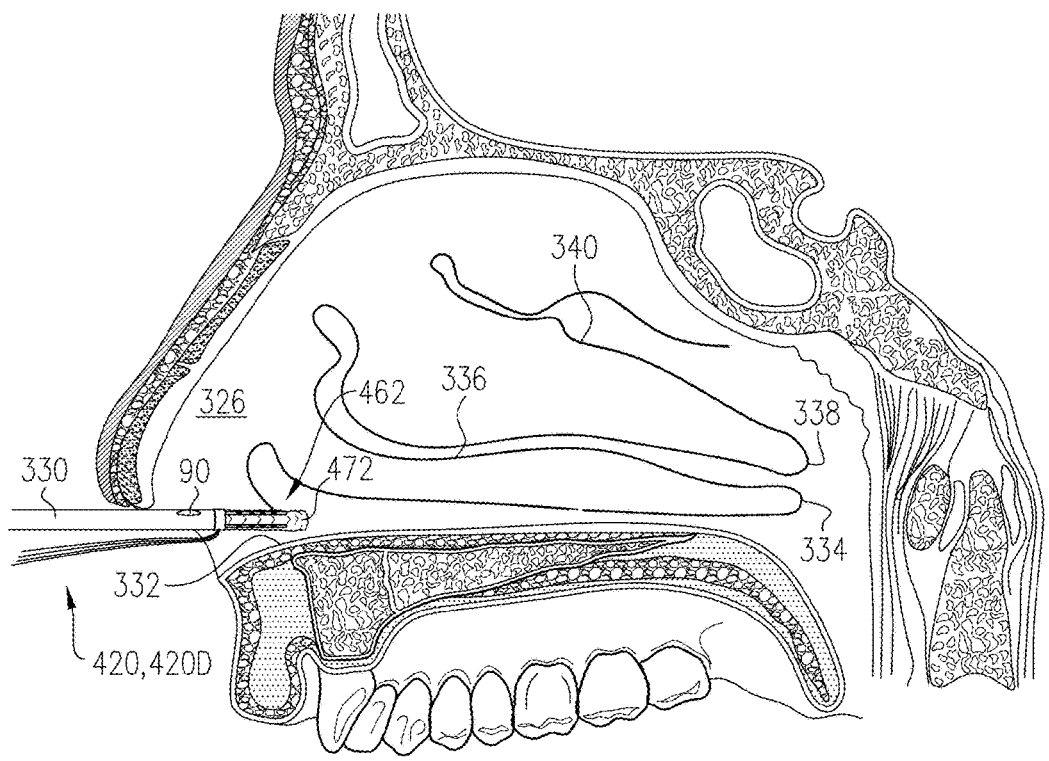
FIGS. 47A-E are schematic illustrations of a method for stimulating the SPG using the SPG stimulating device of FIG. 46, in accordance with an application of the present invention.
Figure 47B:
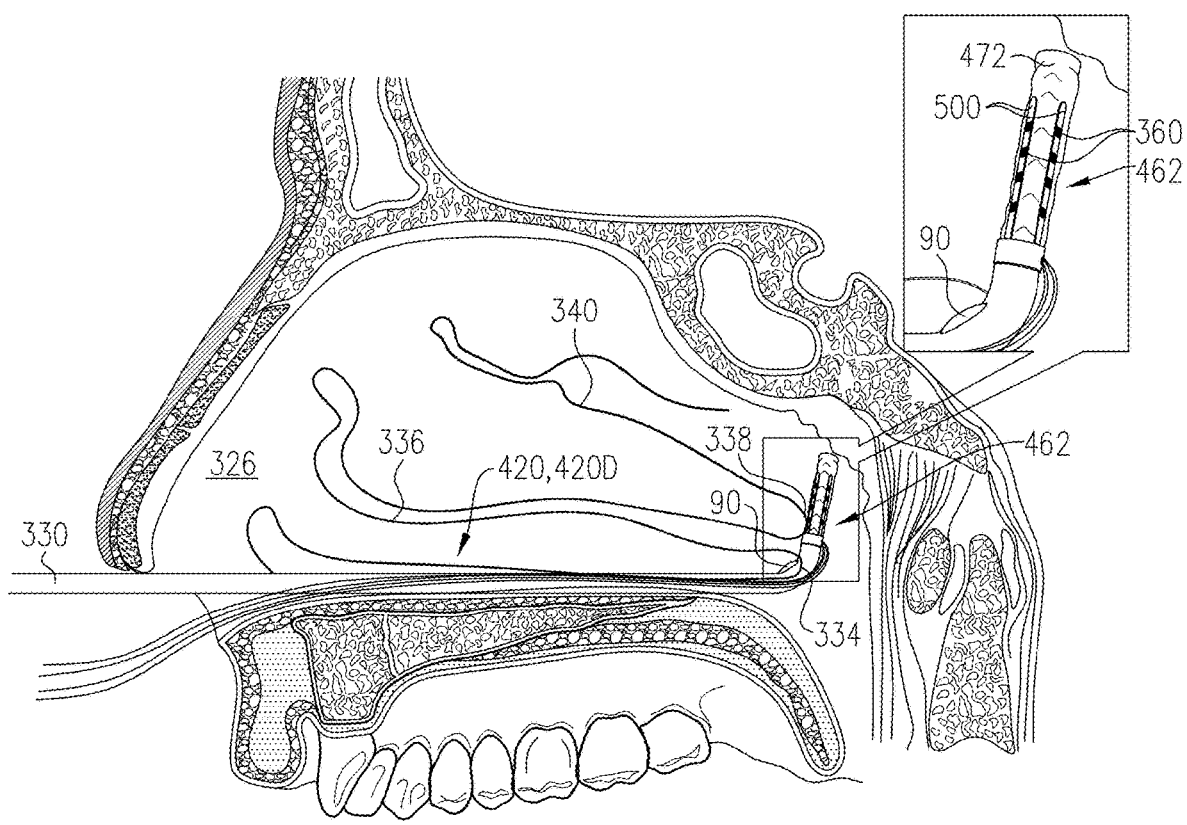

After electrode mount 362 is disposed within nasal cavity 326, such as shown in FIG. 47A, electrode mount 362 is deployed superiorly away from tube 330 while tube 330 is disposed along floor 332 of nasal cavity 326, such as shown in FIG. 47B.

Figure 47C:
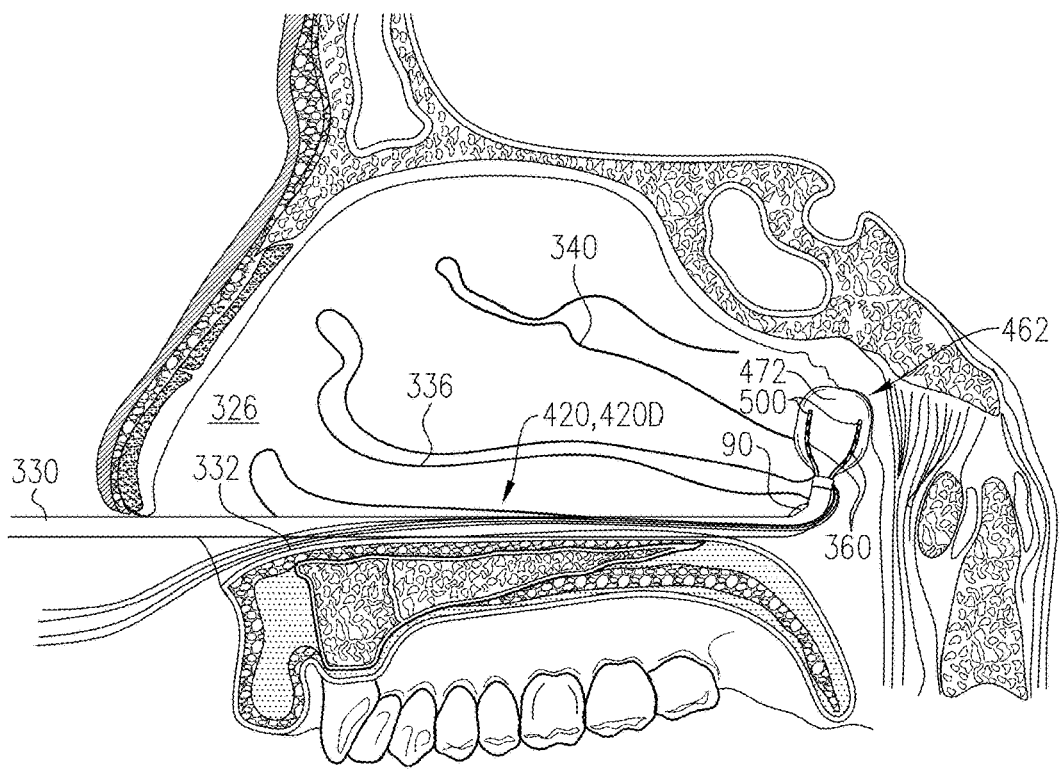

As shown in FIG. 47C, balloon 472 is inflated, thereby changing the shape of struts 500 (either elastically or plastically) so as to bring at least one of the one or more electrodes 360 into contact with lateral wall 364A of nasal cavity 326 at an area of middle meatus 366, near posterior end 334 of inferior turbinate 336 and posterior end 338 of middle turbinate 340 and an area of sphenopalatine foramen 368.

Figure 47D:
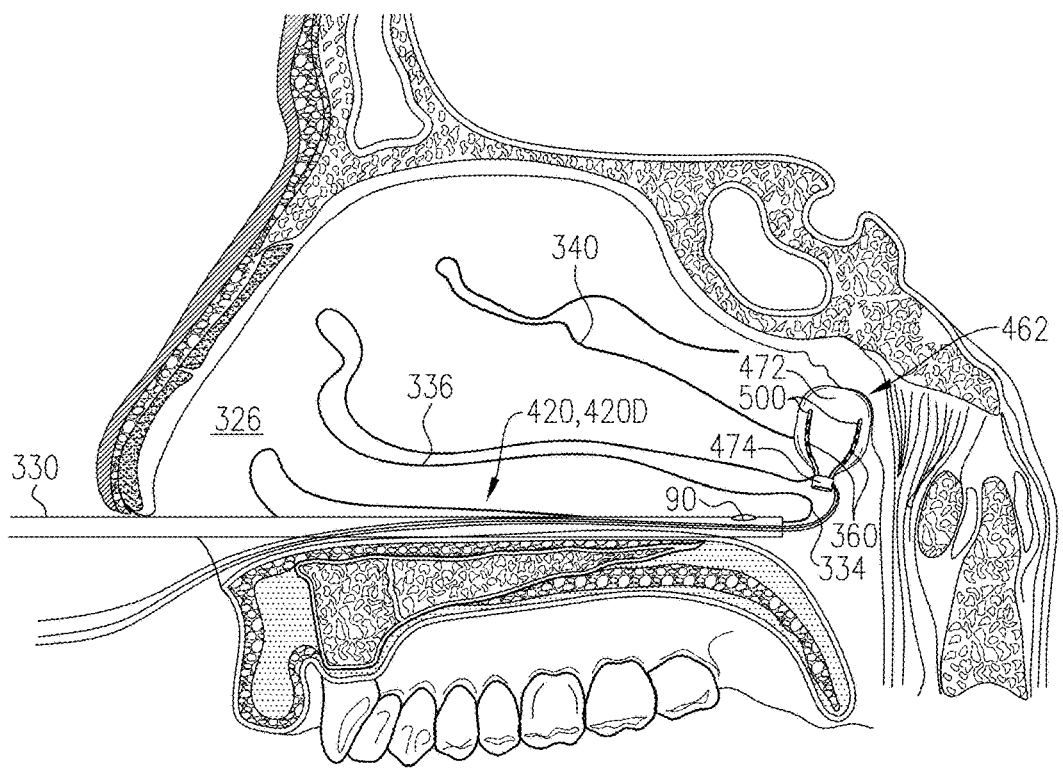
Figure 47E:
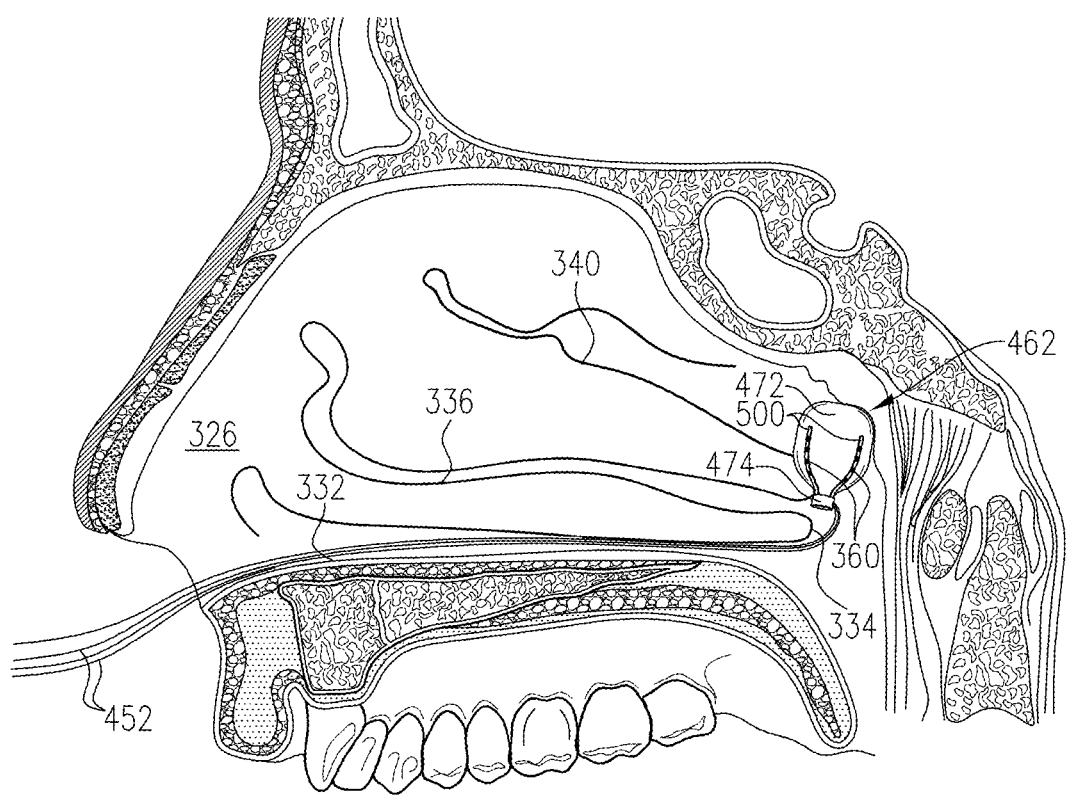

Electrode mount 462 is released from tube 330, as shown in FIG. 47D, and tube 330 is retracted, as shown in FIG. 47E, leaving electrode mount 462 (including the one or more electrodes, struts 500, and balloon 472) implanted in nasal cavity 326 for subsequent application of SPG stimulation using the one or more electrodes 360.

Reference is now made to FIGS. 48A-D, which are schematic illustrations of an SPG stimulating device 420E and a method for stimulating SPG 22 of patient 24 from within nasal cavity 326 using SPG stimulating device 420E, in accordance with respective applications of the present invention. SPG stimulating device 420E is one implementation of SPG stimulating device 420 described hereinabove with reference to FIGS. 41A-48D, and may implement any of the techniques described hereinabove with reference to FIG. 15 and/or the other figures, mutatis mutandis.

In this configuration, electrode mount 462 comprises a spring 480, to which the one or more electrodes 360 are coupled. Optionally, only the undulations on one side of electrode mount 462 comprise electrodes 360. For example, spring 480 may be shaped so as to define undulations having proximal and distal peaks, and optionally surrounding an axis, or may be shaped as a crown spring.

Figure 48A:
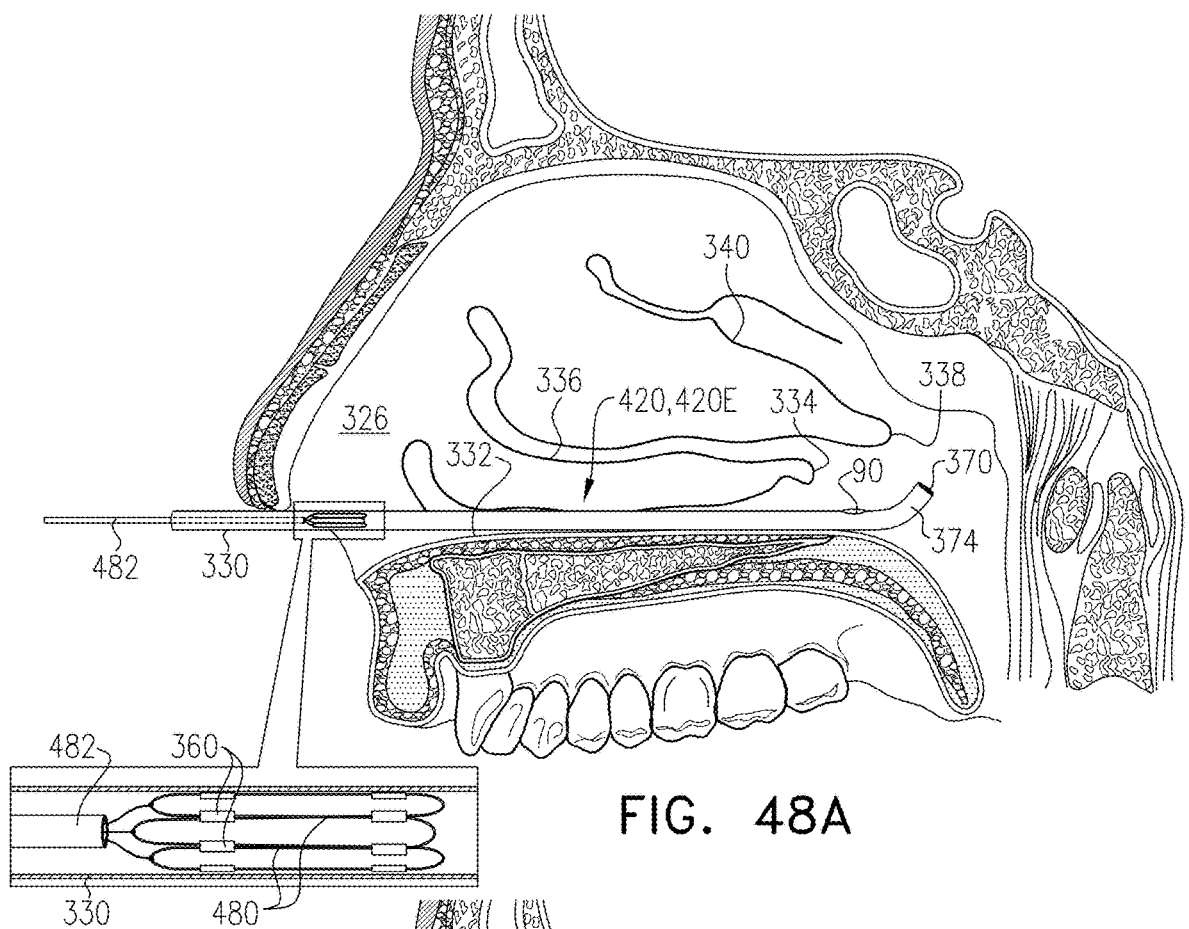
FIGS. 48A-D are schematic illustrations of another SPG stimulating device and a method for stimulating the SPG from within the nasal cavity using the SPG stimulating device, in accordance with respective applications of the present invention.

Electrode mount 462, including spring 480, is initially compressed within tube 330, as shown in FIG. 48A. As also shown in FIG. 48A, tube 330 and electrode mount 462 are inserted into nasal cavity 326 of the patient and tube 330 is advanced along floor 332 of nasal cavity 326 to near posterior end 334 of inferior turbinate 336. As further shown in FIG. 48A, distal end portion 374 of tube 330 is deflected, such as using steering techniques described hereinabove.

Figure 48B:
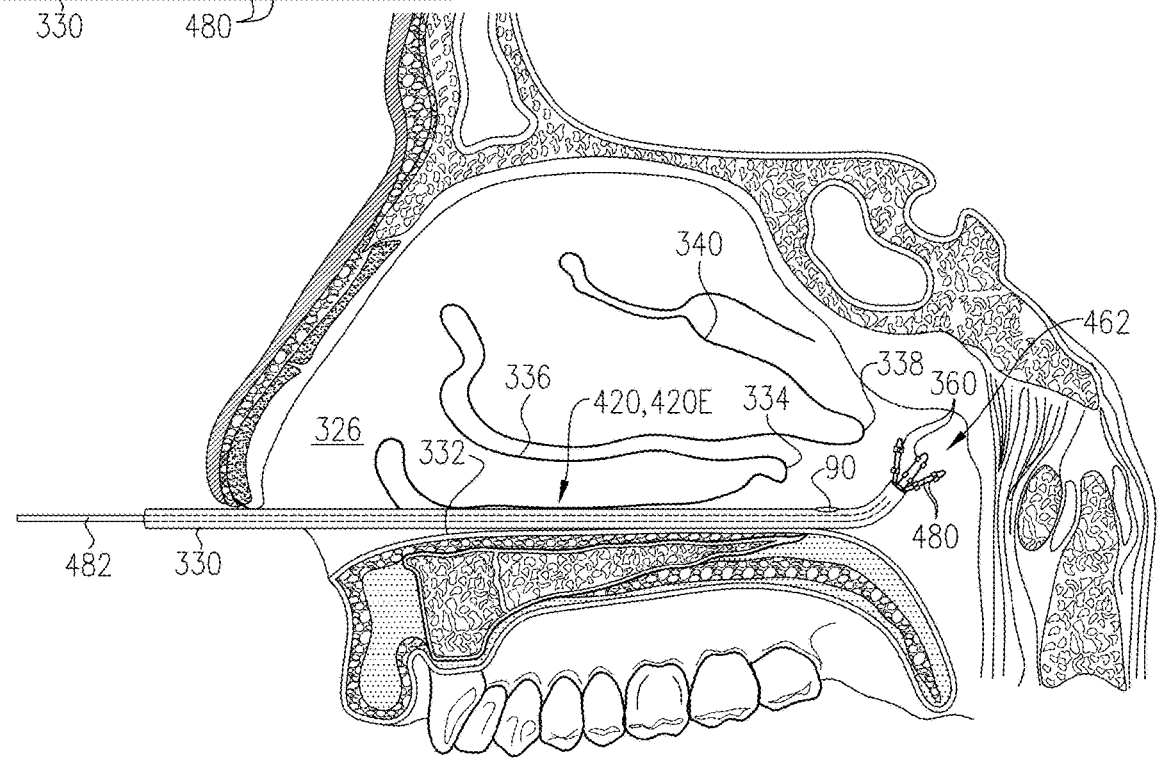

As shown in FIG. 48B, electrode mount 462, including spring 480, is typically deployed from tube 330 out of distal end opening 370 of the tube 330. For example, a pusher rod 482 may be used to distally push electrode mount 462.

Figure 48C:
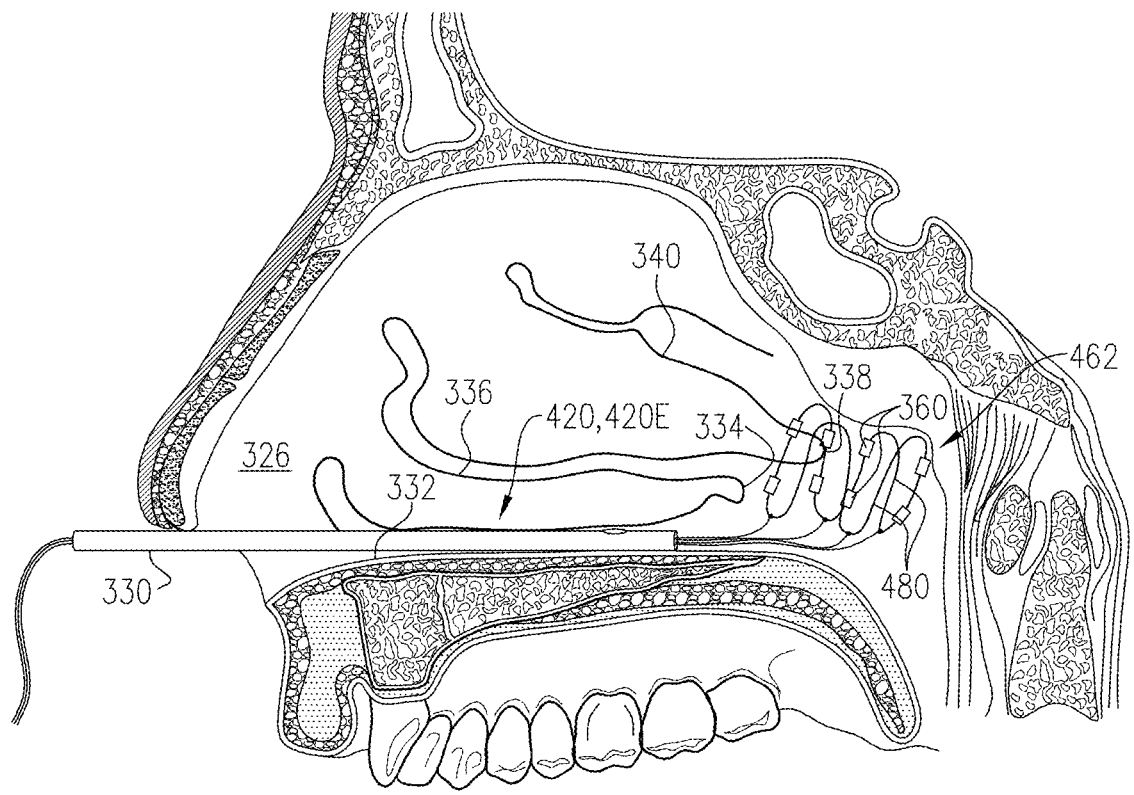
Figure 48D:
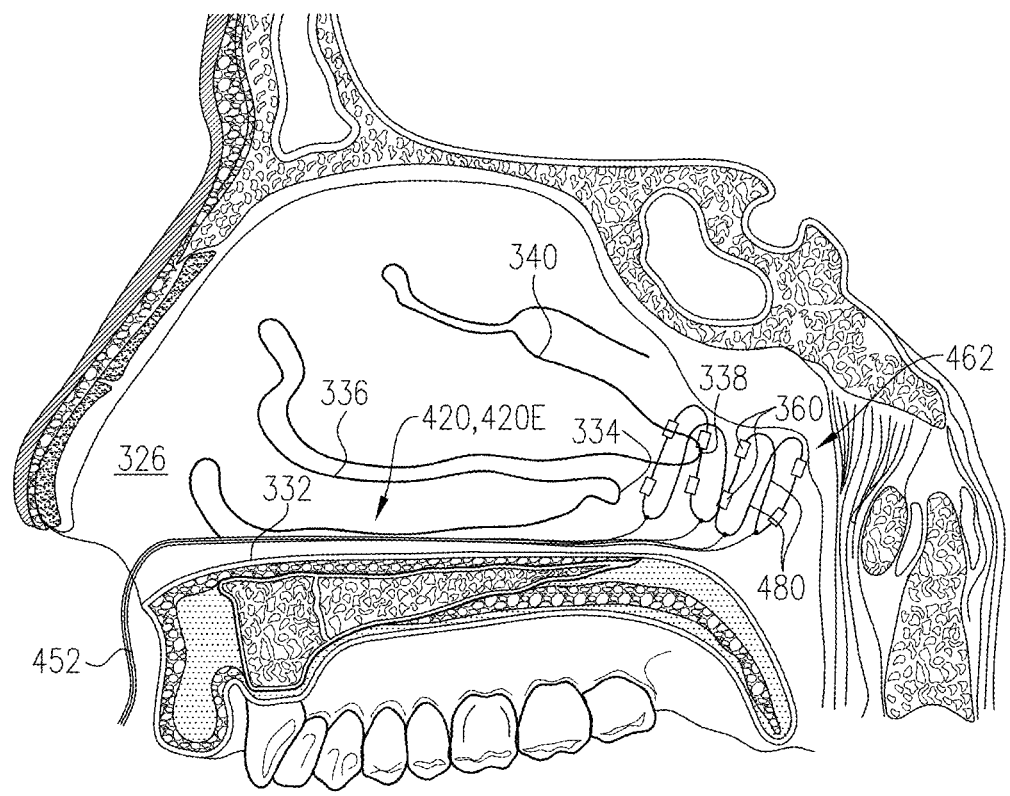

As shown in FIG. 48C, upon the release of electrode mount 462 from tube 330, spring 480 expands, typically self-expands, so as to bring at least one of the one or more electrodes 360 into contact with lateral wall 364A of nasal cavity 326 at an area of middle meatus 366, near posterior end 334 of inferior turbinate 336 and posterior end 338 of middle turbinate 340 and an area of sphenopalatine foramen 368.

Electrode mount 462 is released from tube 330, as shown in FIG. 48C, and tube 330 is retracted, as shown in FIG.

47D, leaving electrode mount 462 implanted in nasal cavity 326 for subsequent application of SPG stimulation using the one or more electrodes 360.

Reference is made to FIGS. 16A-48D. For some applications, electrode mount 362 is removably disposed within tube 330, and is configured, upon deployment from tube 330, to superiorly deploy the one or more electrodes 360 and position the one or more electrodes 360 against wall 364 of nasal cavity 326 for stimulating SPG 22.

For some of these applications, electrode mount 362 is removably constrained within tube 330 in a constrained state, and is configured to expand to an expanded state after the deployment from tube 330, so as to superiorly deploy the one or more electrodes 360 and position the one or more electrodes 360 against wall 364 of nasal cavity 326 for stimulating SPG 22.

Reference is made to FIGS. 16A-48D. Optionally, SPG stimulating devices 320 and 420 are implemented with at least one electrode outside nasal cavity 326, in addition to the one or more electrodes 360 within the nasal cavity. For example, the external electrode may be placed such as described hereinabove for SPG stimulating device 20 with reference to FIGS. 8A-B, FIGS. 9A-C, and/or FIGS. 10A-B, mutatis *mutandis*.

Reference is made to FIGS. 1-48D. Typically, control unit 26 or 454 is configured to drive the one or more electrodes to stimulate the SPG by applying alternating current to the one or more electrodes. Typically, the circuitry is configured to apply the current so as to excite tissue of the SPG, without ablating the tissue and/or blocking nerve signals.

For some applications, the circuitry of the control unit is configured to drive the alternating current in pulses having a pulse width typically of at least 50 microseconds, such as at least 100 microseconds (e.g., at least 200 microseconds), no more than 5,000 microseconds, such as no more than 600 microseconds (e.g., no more than 400 microseconds), and/or 50-5,000 microseconds, e.g., 100-600 microseconds, such as 200-400 microseconds and/or a frequency of typically at least 10 Hz, no more than 100 Hz (e.g., no more than 40 Hz), and/or 10-100 Hz, such as 10-60 Hz, e.g., 10-40 Hz.

For any of the applications described herein, the circuitry may be configured to drive the alternating current at a strength that is insufficient to induce a significant increase in permeability of a blood-brain barrier (BBB) of the subject.

In an embodiment, techniques and apparatus described in one or more of the following patent applications, which are incorporated herein by reference, are combined with techniques and apparatus described herein:

U.S. application Ser. No. 18/351,247, filed Jul. 12, 2023, which published as US Patent Application Publication 2025/0018187 to Gross et al.

U.S. application Ser. No. 18/229,379, filed Aug. 2, 2023, which published as US Patent Application Publication 2025/0018193 to Gross et al., now abandoned U.S. application Ser. No. 18/640,726, filed Apr. 19, 2024, now U.S. Pat. No. 12,208,267.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for stimulating a sphenopalatine ganglion (SPG) of a patient, the method comprising:
    inserting a tube and an electrode mount into a nasal cavity of the patient and advancing the tube along a floor of the nasal cavity to near a posterior end of an inferior turbinate;
    deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and
    applying, to the one or more electrodes, a current configured to stimulate the SPG via the wall,
    wherein deploying the one or more electrodes comprises deploying the one or more electrodes superiorly and laterally away from the tube to an area of a middle meatus and an area of a sphenopalatine foramen while the tube is disposed along the floor of the nasal cavity.

2. The method according to claim 1, wherein the wall is a lateral wall of the nasal cavity, and wherein deploying the one or more electrodes comprises deploying the one or more electrodes superiorly and laterally away from the tube to the area of the middle meatus and the sphenopalatine foramen, so as to position the one or more electrodes against the lateral wall of the nasal cavity.

3. The method according to claim 1, wherein the tube is shaped so as to define a side opening, and wherein deploying the one or more electrodes away from the tube comprises deploying the one or more electrodes away from the tube via the side opening.

4. A method for stimulating a sphenopalatine ganglion (SPG) of a patient, the method comprising:
    inserting a tube and an electrode mount into a nasal cavity of the patient and advancing the tube along a floor of the nasal cavity to near a posterior end of an inferior turbinate;
    deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and
    applying, to the one or more electrodes, a current configured to stimulate the SPG via the wall,
    wherein deploying the one or more electrodes comprises, after deploying the one or more electrodes superiorly away from the tube, disengaging the tube from the electrode mount.

5. The method according to claim 4, wherein deploying the one or more electrodes comprises deploying the one or more electrodes superiorly and laterally away from the tube to an area of a middle meatus and an area of a sphenopalatine foramen while the tube is disposed along the floor of the nasal cavity.

6. A method for stimulating a sphenopalatine ganglion (SPG) of a patient, the method comprising:
    inserting a tube and an electrode mount into a nasal cavity of the patient and advancing the tube along a floor of the nasal cavity to near a posterior end of an inferior turbinate;
    deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and
    applying, to the one or more electrodes, a current configured to stimulate the SPG via the wall, wherein the tube is steerable, and wherein deploying the one or more electrodes superiorly away from the tube while the tube is disposed along the floor of the nasal cavity comprises activating a deflecting mechanism to bend a distal end portion of the tube in at least one direction with respect to an axis of the tube, in order to facilitate superior deployment of the one or more electrodes away from the tube.

7. The method according to claim 1, wherein a distal end portion of the tube is configured to be curved when in an unconstrained resting state, in order to facilitate superior deployment of the one or more electrodes away from the tube.

8. A method for stimulating a sphenopalatine ganglion (SPG) of a patient, the method comprising:
inserting a tube and an electrode mount into a nasal cavity of the patient and advancing the tube along a floor of the nasal cavity to near a posterior end of an inferior turbinate;
deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and
applying, to the one or more electrodes, a current configured to stimulate the SPG via the wall,
wherein the electrode mount is removably disposed within the tube, and is configured, upon deployment from the tube, to superiorly deploy the one or more electrodes and position the one or more electrodes against a wall of the nasal cavity for stimulating the SPG, and
wherein the electrode mount is removably constrained within the tube in a constrained state, and is configured to expand to an expanded state after the deployment from the tube, so as to superiorly deploy the one or more electrodes and position the one or more electrodes against a wall of the nasal cavity for stimulating the SPG.

9. A method for stimulating a sphenopalatine ganglion (SPG) of a patient, the method comprising:
inserting a tube and an electrode mount into a nasal cavity of the patient and advancing the tube along a floor of the nasal cavity to near a posterior end of an inferior turbinate;
deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and
applying, to the one or more electrodes, a current configured to stimulate the SPG via the wall,
wherein the electrode mount comprises an inflatable electrode mount,
wherein the one or more electrodes are coupled to an external surface of the inflatable electrode mount, and
wherein deploying the one or more electrodes comprises inflating the inflatable electrode mount, to superiorly deploy the one or more electrodes and position the one or more electrodes against the wall of the nasal cavity.

10. The method according to claim 9, wherein the wall is a lateral wall of the nasal cavity, and wherein deploying the one or more electrodes comprises deploying the one or more electrodes superiorly and laterally away from the tube while the tube is disposed along the floor of the nasal cavity, so as to bring the least one of the one or more electrodes into the contact with the lateral wall of the nasal cavity.

11. A method for stimulating a sphenopalatine ganglion (SPG) of a patient, the method comprising:
inserting a tube and an electrode mount into a nasal cavity of the patient and advancing the tube along a floor of the nasal cavity to near a posterior end of an inferior turbinate;
deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and
applying, to the one or more electrodes, a current configured to stimulate the SPG via the wall,
wherein the electrode mount comprises a flexible wire, to which the one or more electrodes are fixed.

12. The method according to claim 11, wherein deploying the one or more electrodes comprises shaping the flexible wire as a loop.

13. The method according to claim 11, wherein deploying the one or more electrodes comprises shaping the flexible wire as a curve.

14. A method for stimulating a sphenopalatine ganglion (SPG) of a patient, the method comprising:
inserting a tube and an electrode mount into a nasal cavity of the patient and advancing the tube along a floor of the nasal cavity to near a posterior end of an inferior turbinate;
deploying one or more electrodes of the electrode mount superiorly away from the tube while the tube is disposed along the floor of the nasal cavity and the electrode mount is disposed within the nasal cavity, so as to bring at least one of the one or more electrodes into contact with a wall of the nasal cavity; and
applying, to the one or more electrodes, a current configured to stimulate the SPG via the wall,
wherein the electrode mount comprises one or more struts, to which the one or more electrodes are fixed.

15. The method according to claim 14, wherein the one or more struts comprise a plurality of struts arranged as spokes radiating from a hub.

16. The method according to claim 14, wherein the one or more struts comprise a plurality of struts arranged as a frame.

17. The method according to claim 14, wherein deploying the one or more electrodes comprises inflating a balloon, which is not fixed to the one or more struts, so as to press the one or more struts into the wall of the nasal cavity.

18. The method according to claim 17, wherein the one or more struts comprise a plurality of struts arranged on only one side of the balloon.

19. The method according to claim 17, wherein the one or more struts comprise a malleable material.

20. The method according to claim 17, wherein deploying the one or more electrodes comprises, after deploying the one or more electrodes superiorly away from the tube, disengaging the tube and the balloon from the electrode mount.

21. The method according to claim 17, wherein the electrode mount comprises the balloon.

22. The method according to claim 21, wherein deploying the one or more electrodes comprises, after deploying the one or more electrodes superiorly away from the tube, disengaging the tube from the electrode mount, including from the balloon.

* * * * *